(12) United States Patent
Hinman

(10) Patent No.: US 11,638,590 B2
(45) Date of Patent: *May 2, 2023

(54) ARTICULATING MECHANISMS AND LINK SYSTEMS WITH TORQUE TRANSMISSION IN REMOTE MANIPULATION OF INSTRUMENTS AND TOOLS

(71) Applicant: INTUITIVE SURGICAL OPERATIONS, INC., Sunnyvale, CA (US)

(72) Inventor: Cameron D. Hinman, Woodside, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 16/411,481

(22) Filed: May 14, 2019

(65) Prior Publication Data

US 2019/0290309 A1 Sep. 26, 2019

Related U.S. Application Data

(60) Division of application No. 11/122,598, filed on May 4, 2005, now Pat. No. 10,321,927, which is a
(Continued)

(51) Int. Cl.
*A61B 17/00* (2006.01)
*A61B 17/29* (2006.01)
(Continued)

(52) U.S. Cl.
CPC .............. *A61B 17/29* (2013.01); *A61B 17/00* (2013.01); *A61B 17/07207* (2013.01);
(Continued)

(58) Field of Classification Search
CPC ......... A61B 17/00; A61B 34/00; A61B 34/30; A61B 34/70
(Continued)

(56) References Cited

U.S. PATENT DOCUMENTS 1,820,463 A 8/1931 Klein
2,526,105 A 10/1950 Adams
(Continued)

FOREIGN PATENT DOCUMENTS

EP 0165718 A2 12/1985
EP 0598618 A2 5/1994
(Continued)

OTHER PUBLICATIONS

Cox J.L., "The Minimally Invasive Maze-III Procedure," Operative Techniques in Thoracic and Cardiovascular Surgery, W.B. Saunders Company, 2000, vol. 5 (1), pp. 79-92.
(Continued)

*Primary Examiner* — Lynsey C Eiseman
(74) *Attorney, Agent, or Firm* — Haynes and Boone, LLP

(57) ABSTRACT

An articulating mechanism capable of transmitting torque for remote manipulation of a surgical or diagnostic tool comprises at least two adjacent links. A first adjacent link of the adjacent links has a ball and a second adjacent link of the adjacent links has a socket for receiving the ball to form a ball and socket joint. The ball and socket joint includes at least one engaging pin and reciprocal slot that provides for torque transmission between the adjacent links while also allowing for pivoting movement of the first adjacent link relative to the second adjacent link. The articulating mechanism also comprises at least one set of cables connecting the first adjacent link and the second adjacent link to one another such that movement of the first adjacent link causes corresponding relative movement of the second adjacent link.

20 Claims, 39 Drawing Sheets

Related U.S. Application Data continuation-in-part of application No. 10/997,372, filed on Nov. 23, 2004, now Pat. No. 9,700,334.

(51) Int. Cl.
  *A61B 34/30* (2016.01)
  *A61B 17/072* (2006.01)
  *A61B 17/28* (2006.01)
  *A61B 17/32* (2006.01)
  *A61B 90/50* (2016.01)
  *A61B 1/005* (2006.01)
  *A61B 17/3207* (2006.01)

(52) U.S. Cl.
  CPC .............. *A61B 17/28* (2013.01); *A61B 17/32* (2013.01); *A61B 34/30* (2016.02); *A61B 1/0055* (2013.01); *A61B 17/320758* (2013.01); *A61B 90/50* (2016.02); *A61B 2017/003* (2013.01); *A61B 2017/00323* (2013.01); *A61B 2017/2905* (2013.01); *A61B 2017/2927* (2013.01); *A61B 2017/320032* (2013.01)

(58) Field of Classification Search
  USPC .............................................................. 606/1
  See application file for complete search history.

(56) References Cited

U.S. PATENT DOCUMENTS

| | | | |
|---|---|---|---|
| 3,060,972 | A | 10/1962 | Sheldon |
| 3,071,161 | A | 1/1963 | Ulrich |
| 3,190,286 | A | 6/1965 | Stokes |
| 3,557,780 | A | 1/1971 | Sato |
| 3,605,725 | A | 9/1971 | Bentov |
| 3,609,994 | A * | 10/1971 | Colletti ................. F16D 3/2052 464/122 |
| 3,691,788 | A | 9/1972 | Mazziotti |
| 3,799,151 | A | 3/1974 | Fukaumi et al. |
| 4,466,649 | A | 8/1984 | Ozawa |
| 4,489,826 | A | 12/1984 | Dubson |
| 4,580,551 | A | 4/1986 | Siegmund et al. |
| 4,636,180 | A | 1/1987 | Runkle |
| 4,700,693 | A | 10/1987 | Lia et al. |
| 4,763,669 | A | 8/1988 | Jaeger |
| 4,790,294 | A | 12/1988 | Allred, III et al. |
| 4,834,761 | A | 5/1989 | Walters |
| 4,854,626 | A | 8/1989 | Duke |
| 4,880,015 | A | 11/1989 | Nierman |
| 4,984,942 | A | 1/1991 | Holtz |
| 4,984,951 | A | 1/1991 | Jameson |
| 4,988,349 | A | 1/1991 | Pennig |
| 5,069,569 | A | 12/1991 | Lieser |
| 5,174,276 | A | 12/1992 | Crockard |
| 5,257,618 | A | 11/1993 | Kondo |
| 5,271,381 | A | 12/1993 | Ailinger et al. |
| 5,273,026 | A | 12/1993 | Wilk |
| 5,286,228 | A | 2/1994 | Lee et al. |
| 5,297,443 | A | 3/1994 | Wentz |
| 5,314,424 | A | 5/1994 | Nicholas |
| 5,322,064 | A | 6/1994 | Lundquist |
| 5,325,845 | A | 7/1994 | Adair |
| 5,330,502 | A | 7/1994 | Hassler et al. |
| 5,354,162 | A | 10/1994 | Burdea et al. |
| 5,381,782 | A | 1/1995 | Delarama et al. |
| 5,383,738 | A | 1/1995 | Herbermann |
| 5,403,342 | A | 4/1995 | Tovey et al. |
| 5,405,344 | A | 4/1995 | Williamson et al. |
| 5,425,743 | A | 6/1995 | Nicholas |
| 5,441,494 | A | 8/1995 | Ortiz |
| 5,449,206 | A * | 9/1995 | Lockwood .............. F16L 11/18 138/120 |
| 5,454,827 | A | 10/1995 | Aust et al. |
| 5,476,479 | A | 12/1995 | Green et al. |
| 5,486,154 | A | 1/1996 | Kelleher |
| 5,490,819 | A | 2/1996 | Nicholas et al. |
| 5,498,256 | A | 3/1996 | Furnish |
| 5,513,827 | A | 5/1996 | Michelson |
| 5,520,678 | A | 5/1996 | Heckele et al. |
| 5,522,788 | A | 6/1996 | Kuzmak |
| 5,549,636 | A | 8/1996 | Li |
| 5,562,699 | A | 10/1996 | Heimberger et al. |
| 5,570,919 | A | 11/1996 | Eusebe |
| 5,599,151 | A | 2/1997 | Daum et al. |
| 5,609,601 | A | 3/1997 | Kolesa et al. |
| 5,620,415 | A | 4/1997 | Lucey et al. |
| 5,624,398 | A | 4/1997 | Smith et al. |
| 5,626,608 | A | 5/1997 | Cuny et al. |
| 5,632,432 | A | 5/1997 | Schulze et al. |
| 5,643,294 | A | 7/1997 | Tovey et al. |
| 5,647,743 | A | 7/1997 | Schmitt |
| 5,702,408 | A | 12/1997 | Wales et al. |
| 5,704,534 | A | 1/1998 | Huitema et al. |
| 5,707,370 | A | 1/1998 | Berki et al. |
| 5,709,681 | A | 1/1998 | Pennig |
| 5,713,505 | A | 2/1998 | Huitema |
| 5,716,352 | A | 2/1998 | Viola et al. |
| 5,759,151 | A | 6/1998 | Sturges |
| 5,792,164 | A | 8/1998 | Lakatos et al. |
| 5,807,376 | A | 9/1998 | Viola et al. |
| 5,813,813 | A | 9/1998 | Daum et al. |
| 5,823,066 | A | 10/1998 | Huitema et al. |
| 5,827,323 | A | 10/1998 | Klieman et al. |
| 5,836,960 | A | 11/1998 | Kolesa et al. |
| 5,845,540 | A | 12/1998 | Rosheim |
| 5,846,183 | A | 12/1998 | Chilcoat |
| 5,873,817 | A | 2/1999 | Kokish et al. |
| 5,899,425 | A | 5/1999 | Corey, Jr. et al. |
| 5,916,146 | A | 6/1999 | Allotta et al. |
| 5,916,147 | A | 6/1999 | Boury |
| 5,921,956 | A | 7/1999 | Grinberg et al. |
| 5,938,678 | A | 8/1999 | Zirps et al. |
| 5,947,984 | A | 9/1999 | Whipple |
| 5,961,532 | A | 10/1999 | Finley et al. |
| 5,980,569 | A | 11/1999 | Scirica |
| 6,019,722 | A | 2/2000 | Spence et al. |
| 6,050,996 | A | 4/2000 | Schmaltz et al. |
| 6,161,543 | A | 12/2000 | Cox et al. |
| 6,233,474 | B1 | 5/2001 | Lemelson |
| 6,250,532 | B1 | 6/2001 | Green et al. |
| 6,270,453 | B1 | 8/2001 | Sakai |
| 6,338,738 | B1 | 1/2002 | Bellotti et al. |
| 6,446,850 | B2 | 9/2002 | Ming-Shun |
| 6,464,704 | B2 | 10/2002 | Schmaltz et al. |
| 6,471,641 | B2 | 10/2002 | Sakamoto |
| 6,471,696 | B1 | 10/2002 | Berube et al. |
| 6,482,149 | B1 | 11/2002 | Torii |
| 6,491,626 | B1 | 12/2002 | Stone et al. |
| 6,571,042 | B1 | 5/2003 | Kordahi |
| 6,626,824 | B2 | 9/2003 | Ruegg et al. |
| 6,635,071 | B2 | 10/2003 | Boche |
| 6,638,213 | B2 | 10/2003 | Ogura et al. |
| 6,638,287 | B2 | 10/2003 | Danitz et al. |
| RE38,335 | E | 11/2003 | Aust et al. |
| 6,641,528 | B2 | 11/2003 | Torii |
| 6,644,532 | B2 | 11/2003 | Green et al. |
| 6,666,854 | B1 | 12/2003 | Lange |
| 6,669,254 | B2 | 12/2003 | Thom et al. |
| 6,676,676 | B2 | 1/2004 | Danitz et al. |
| 6,682,541 | B1 | 1/2004 | Gifford, III et al. |
| 6,743,239 | B1 | 6/2004 | Kuehn et al. |
| 6,746,443 | B1 | 6/2004 | Morley et al. |
| 6,749,560 | B1 | 6/2004 | Konstorum et al. |
| 6,752,823 | B2 | 6/2004 | Prestel |
| 6,764,445 | B2 | 7/2004 | Ramans et al. |
| 6,773,327 | B1 | 8/2004 | Felice et al. |
| 6,817,972 | B2 | 11/2004 | Snow |
| 6,824,548 | B2 | 11/2004 | Smith et al. |
| 6,843,794 | B2 | 1/2005 | Sixto, Jr. et al. |
| 6,858,005 | B2 | 2/2005 | Ohline et al. |
| 6,902,560 | B1 | 6/2005 | Morley et al. |
| 6,942,613 | B2 | 9/2005 | Ewers et al. |
| 6,945,979 | B2 | 9/2005 | Kortenbach et al. |
| 6,960,162 | B2 | 11/2005 | Saadat et al. |

(56) References Cited

U.S. PATENT DOCUMENTS

| | | | |
|---|---|---|---|
| 6,960,163 | B2 | 11/2005 | Ewers et al. |
| 6,976,969 | B2 | 12/2005 | Messerly |
| 6,994,700 | B2 | 2/2006 | Elkins et al. |
| 7,090,637 | B2 | 8/2006 | Danitz et al. |
| 7,138,976 | B1 | 11/2006 | Bouzit et al. |
| 7,480,600 | B2 | 1/2009 | Massie et al. |
| 7,553,275 | B2 | 6/2009 | Padget et al. |
| 7,678,117 | B2 | 3/2010 | Hinman et al. |
| 7,828,808 | B2 | 11/2010 | Hinman et al. |
| 9,700,334 | B2 | 7/2017 | Hinman et al. |
| 10,321,927 | B2 | 6/2019 | Hinman |
| 2001/0023313 | A1 | 9/2001 | Ide |
| 2002/0096177 | A1 | 7/2002 | Toti et al. |
| 2002/0111604 | A1 | 8/2002 | Doyle et al. |
| 2002/0156497 | A1 | 10/2002 | Nagase et al. |
| 2002/0161281 | A1 | 10/2002 | Jaffe et al. |
| 2002/0177750 | A1 | 11/2002 | Pilvisto et al. |
| 2003/0036748 | A1 | 2/2003 | Cooper et al. |
| 2003/0050649 | A1 | 3/2003 | Brock et al. |
| 2003/0078644 | A1 | 4/2003 | Phan |
| 2003/0109898 | A1 | 6/2003 | Schwarz et al. |
| 2003/0114838 | A1 | 6/2003 | Oneill et al. |
| 2003/0135204 | A1 | 7/2003 | Lee et al. |
| 2003/0149338 | A1 | 8/2003 | Francois et al. |
| 2003/0153902 | A1 | 8/2003 | Doyle et al. |
| 2003/0158463 | A1 | 8/2003 | Julian et al. |
| 2003/0229271 | A1 | 12/2003 | Briscoe et al. |
| 2003/0233026 | A1 | 12/2003 | Saadat et al. |
| 2004/0054322 | A1 | 3/2004 | Vargas |
| 2004/0138529 | A1 | 7/2004 | Wiltshire et al. |
| 2004/0138700 | A1 | 7/2004 | Cooper et al. |
| 2004/0142300 | A1 | 7/2004 | Aravena |
| 2005/0038443 | A1 | 2/2005 | Hedley et al. |
| 2005/0090809 | A1 | 4/2005 | Cooper et al. |
| 2005/0096694 | A1 | 5/2005 | Lee |
| 2005/0107667 | A1 | 5/2005 | Danitz et al. |
| 2005/0119527 | A1 | 6/2005 | Banik et al. |
| 2005/0159732 | A1 | 7/2005 | Rosheim |
| 2005/0251112 | A1 | 11/2005 | Danitz et al. |
| 2006/0009759 | A1 | 1/2006 | Chrisitian et al. |
| 2006/0020287 | A1 | 1/2006 | Lee et al. |
| 2006/0036255 | A1 | 2/2006 | Pond, Jr. et al. |
| 2006/0058582 | A1 | 3/2006 | Maahs et al. |
| 2006/0094931 | A1 | 5/2006 | Danitz et al. |
| 2006/0111209 | A1 | 5/2006 | Hinman et al. |
| 2006/0111615 | A1 | 5/2006 | Danitz et al. |
| 2006/0111616 | A1 | 5/2006 | Danitz |
| 2006/0199999 | A1 | 9/2006 | Ikeda et al. |

FOREIGN PATENT DOCUMENTS

| | | | |
|---|---|---|---|
| EP | 0836833 | A2 | 4/1998 |
| EP | 1132041 | A2 | 9/2001 |
| EP | 0836833 | A3 | 9/2002 |
| EP | 1395398 | B1 | 1/2006 |
| JP | S6376918 | A | 4/1988 |
| JP | H06262549 | A | 9/1994 |
| JP | 2001299768 | A | 10/2001 |
| JP | 2002503131 | A | 1/2002 |
| JP | 2004154164 | A | 6/2004 |
| WO | WO-199849961 | A1 | 11/1998 |
| WO | WO-9856297 | A1 | 12/1998 |
| WO | WO-199915070 | A1 | 4/1999 |
| WO | WO-200110292 | A1 | 2/2001 |
| WO | WO-0189440 | A2 | 11/2001 |
| WO | WO-200213682 | A1 | 2/2002 |
| WO | WO-2004019769 | A1 | 3/2004 |
| WO | WO-2004105578 | A2 | 12/2004 |
| WO | WO-2004105578 | A9 | 4/2005 |
| WO | WO-2005067785 | A1 | 7/2005 |
| WO | WO-2005120326 | A2 | 12/2005 |
| WO | WO-2005120327 | A2 | 12/2005 |
| WO | WO-2006057699 | A1 | 6/2006 |
| WO | WO-2006057700 | A1 | 6/2006 |
| WO | WO-2006057702 | A2 | 6/2006 |
| WO | WO-2006073581 | A2 | 7/2006 |
| WO | WO-2007117076 | A1 | 10/2007 |

OTHER PUBLICATIONS

Danitz, David J.; U.S. Appl. No. 12/766,820 entitled "Articulating mechanism with bifurcating control," filed Apr. 23, 2010.

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Danitz, David J., U.S. Appl. No. 11/344,465, filed Jan. 30, 2006, 28 pages.

Danitz et al.; U.S. Appl. No. 12/109,333 entitled "Articulating instrument," filed Apr. 24, 2008.

Danitz et al.; U.S. Appl. No. 12/766,818 entitled "Articulating instruments with joystick control," filed Apr. 23, 2010.

Extended European Search Report for Application No. EP08009895, dated Jul. 11, 2008, 6 pages.

Hegeman et al; U.S. Appl. No. 11/787,543 entitled "Tool with articulation lock," filed Apr. 16, 2007.

Hegeman et al; U.S. Appl. No. 11/787,608 entitled "Articulating tool with improved tension member system" filed Apr. 16, 2007.

Hinman, Cameron; U.S. Appl. No. 12/508,478 entitled "Articulating mechanism," filed Jul. 23, 2009.

Hinman, Cameron; U.S. Appl. No. 11/787,605 entitled "Tool with multi-state ratcheted end effector," filed Apr. 16, 2007.

Hinman, Cameron; U.S. Appl. No. 11/787,607 entitled "Tool with rotation lock," filed Apr. 16, 2007.

Hinman et al; U.S. Appl. No. 11/787,599 entitled "Tool with end effector force limiter," filed Apr. 16, 2007.

Hinman et al.; U.S. Appl. No. 12/725,377 entitled "Articulating mechanism with flex-hinged links," filed Mar. 16, 2010.

Hinman et al.; U.S. Appl. No. 12/816,359 entitled "Link systems and articulation mechanisms for remote manipulation of surgical or diagnostic tools," filed Jun. 15, 2010.

International Search Report and Written Opinion for Application No. PCT/US2005/018146, dated Dec. 20, 2005, 12 pages.

International Search Report and Written Opinion for Application No. PCT/US2005/041663, dated Nov. 27, 2006, 16 pages.

International Search Report for Application No. PCT/US2005/018145 (WO2005120326), dated Feb. 20, 2006, 5 pages.

International Search Report dated Aug. 26, 2005 for PCT Application No. PCT/US04/15944 filed May 21, 2004, 1 page.

Invitation to Pay Additional Fees, Communication Relating to the Results of the Partial International Search dated Jul. 13, 2006 for PCT Application No. PCT/US2005/041663 filed on Nov. 18, 2005, 3 pages.

Isbell Jr., Lewis; U.S. Appl. No. 12/542,589 entitled "Instrument with articulation lock," filed Aug. 17, 2009.

Prasad S.M., et al., "Epicardial Ablation on the Beating Heart: Progress Towards an Off-Pump Maze Procedure," The Heart Surgery Forum, Forum Multimedia Publishing, LLC, 2002, vol. 5 (2), pp. 100-104.

Simha P.M., et al., "The Elctrocautery Maze—How I Do It," The Heart Surgery Forum, Forum Multimedia Publishing, LLC, 2001, vol. 4 (4), pp. 340-345.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

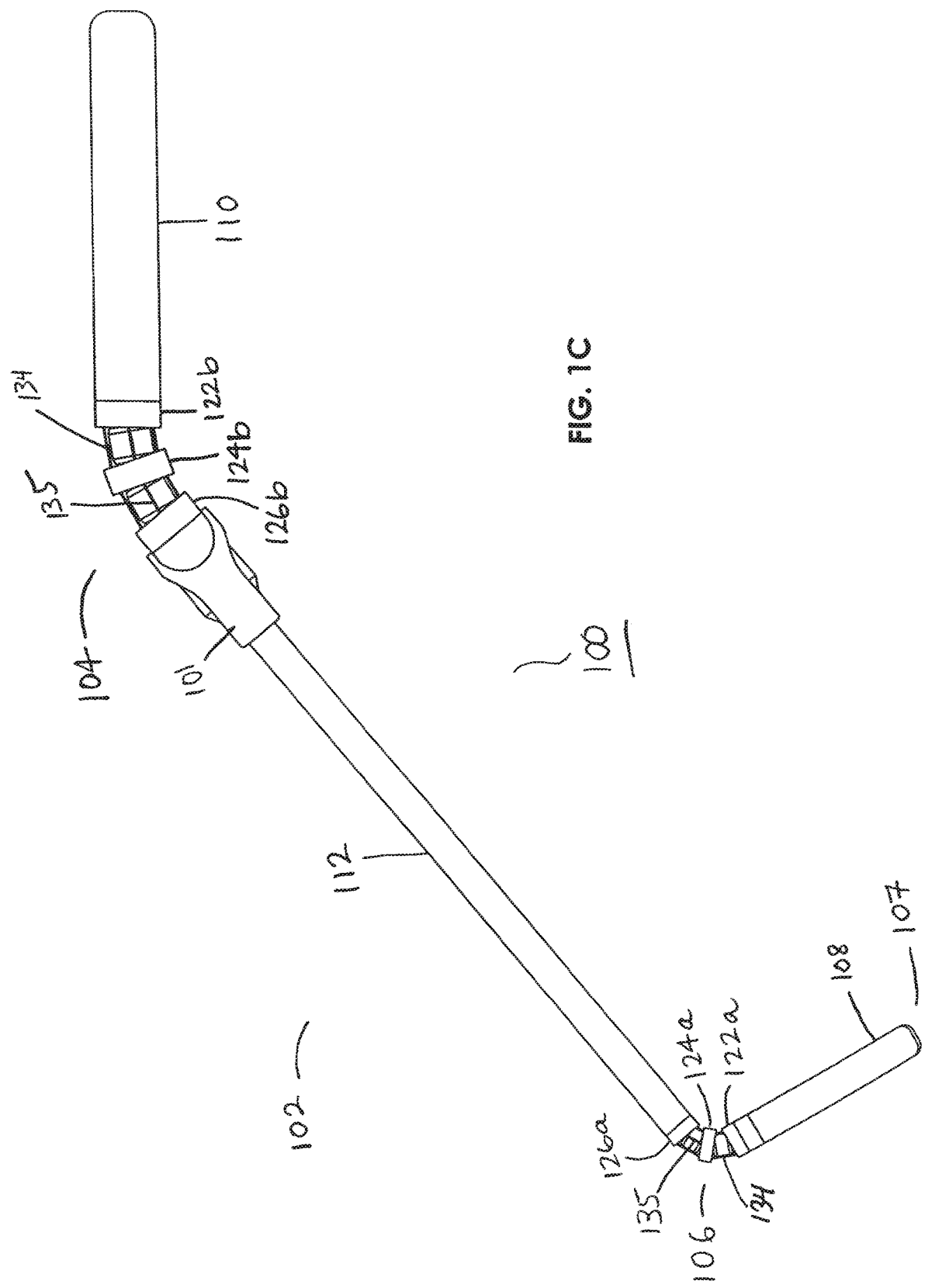

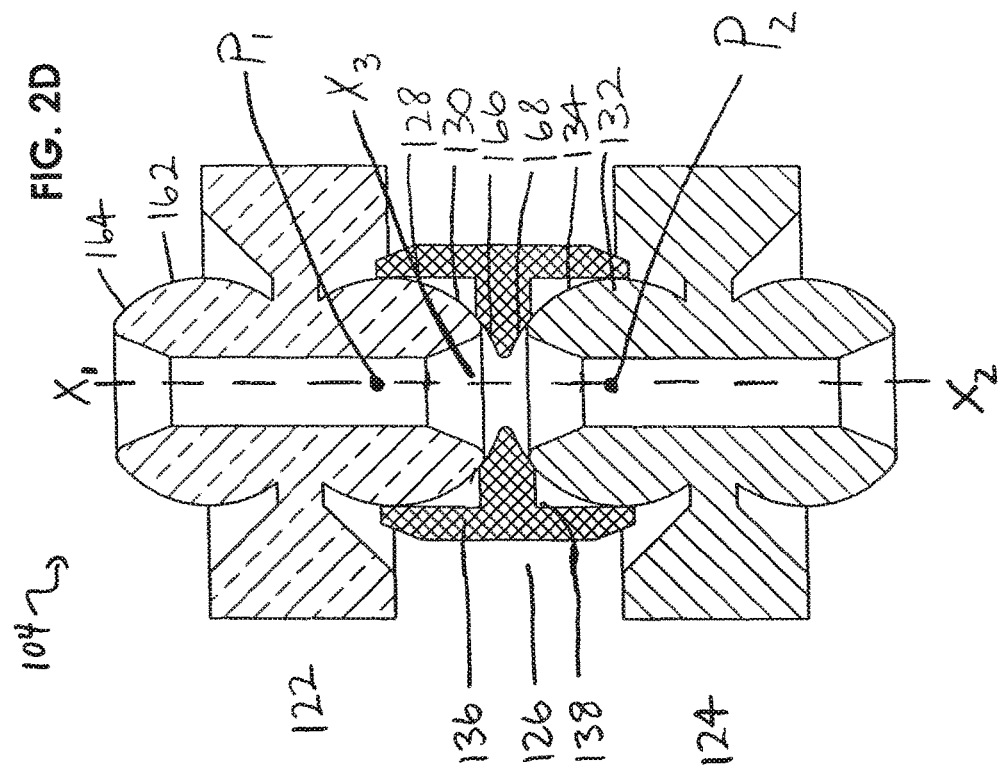
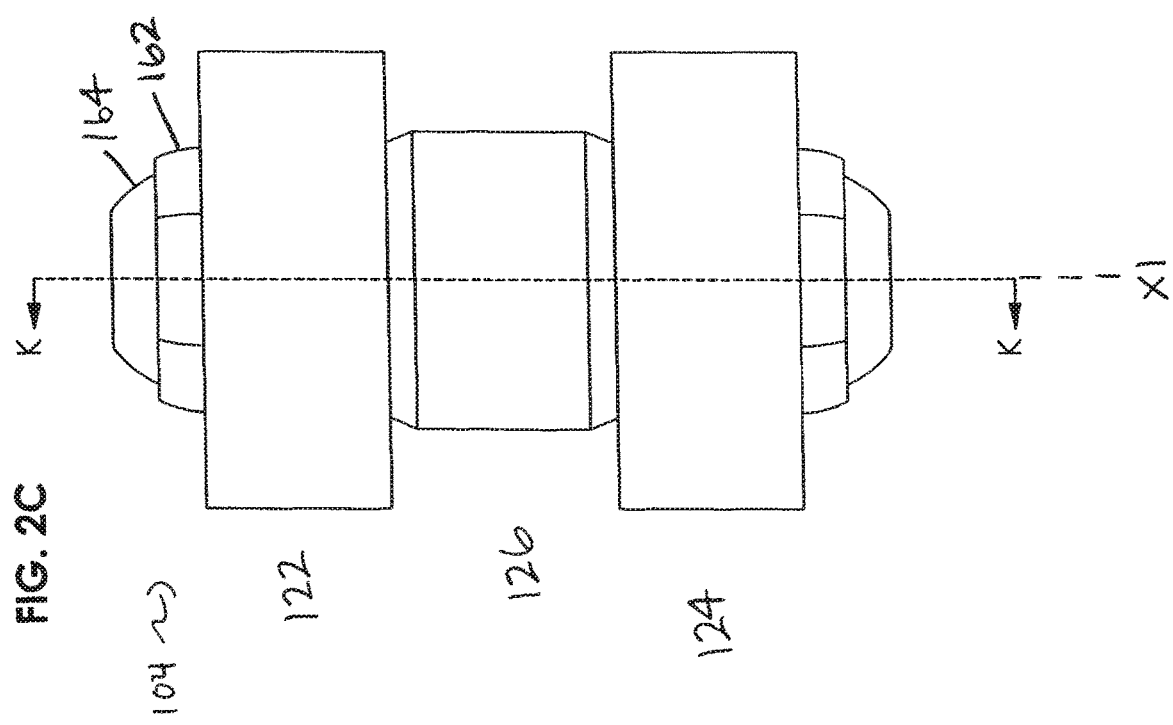

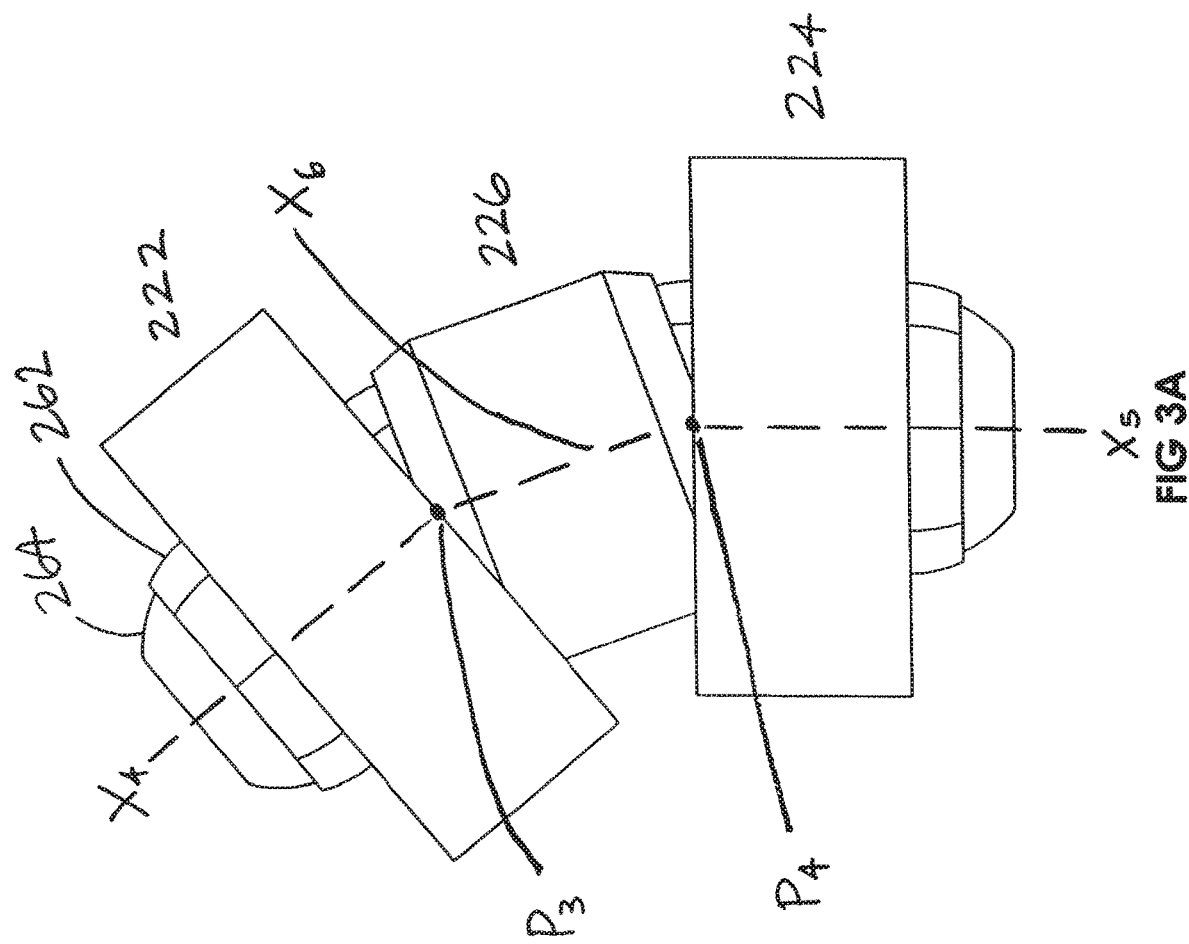

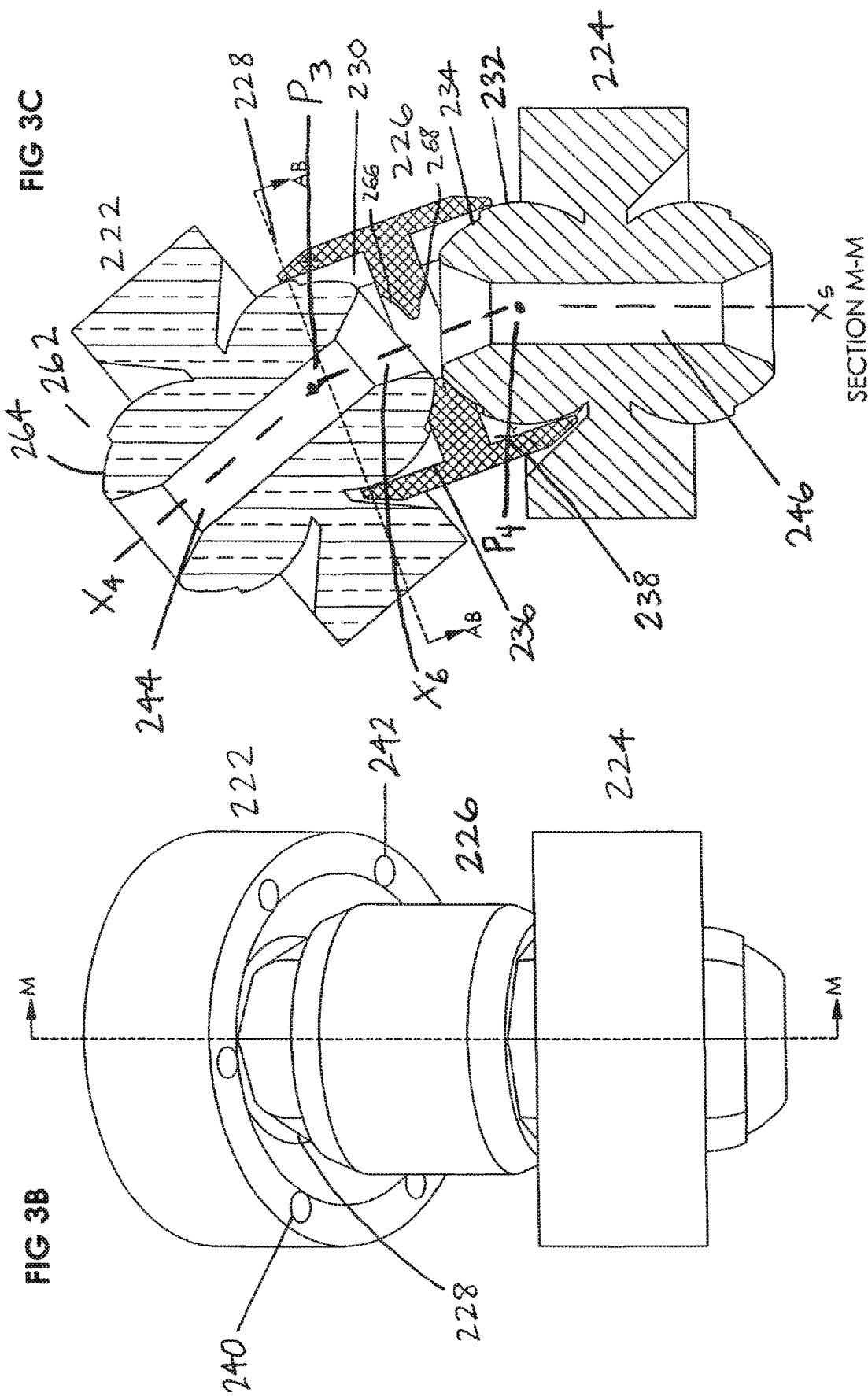

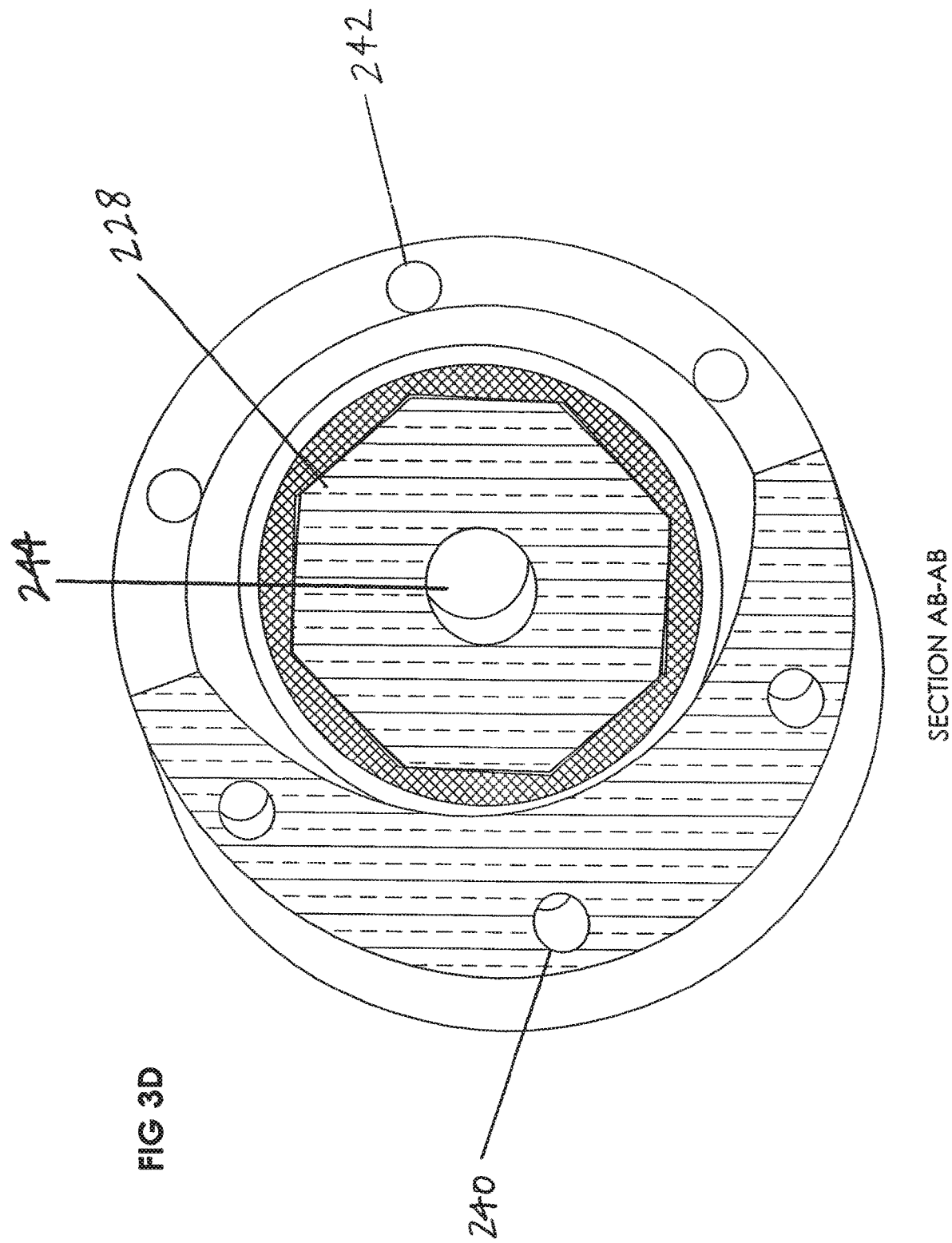

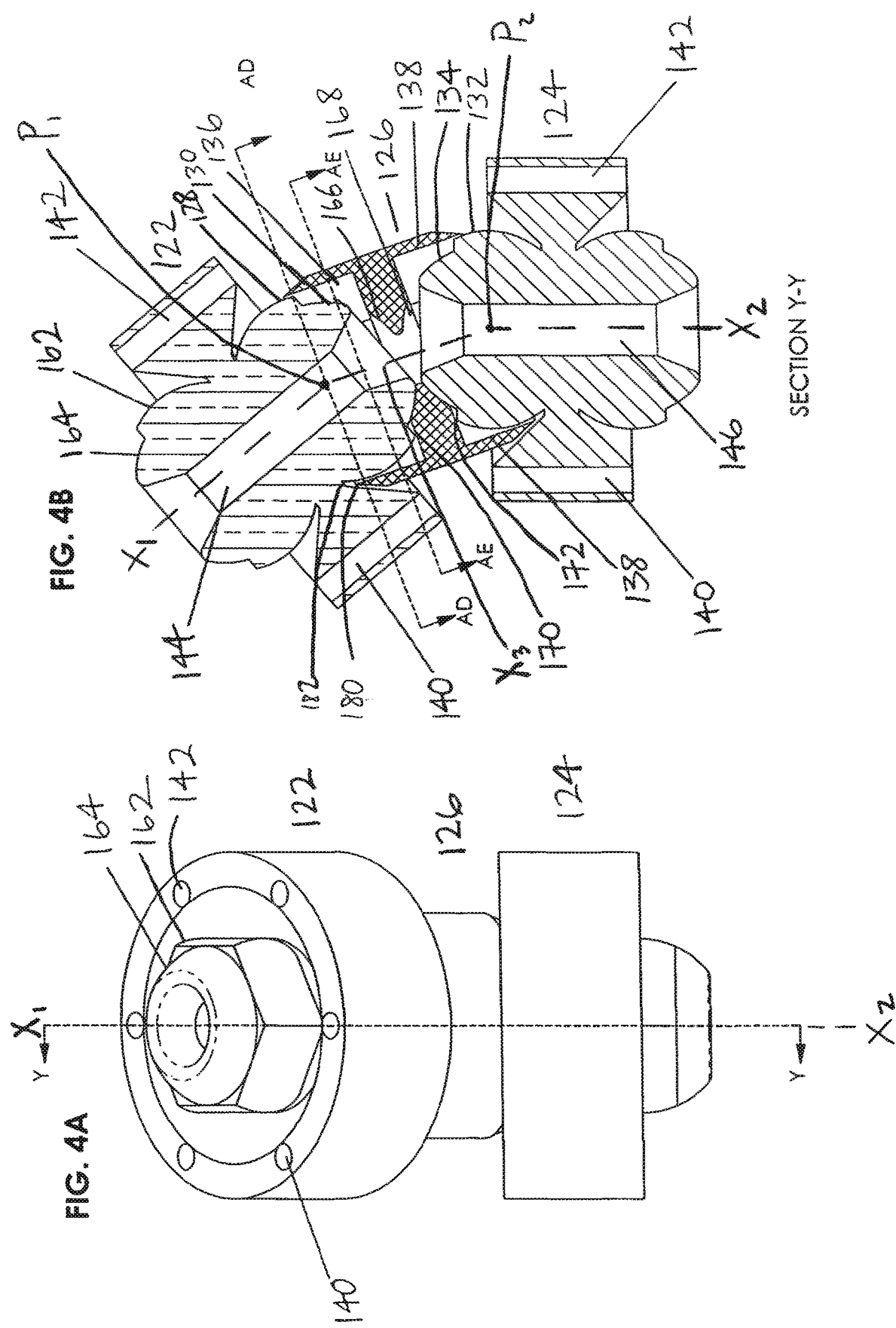

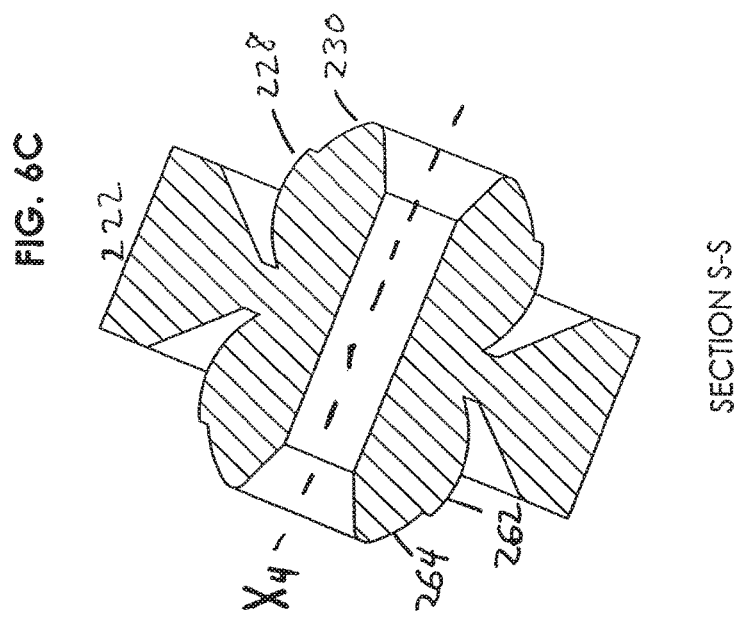
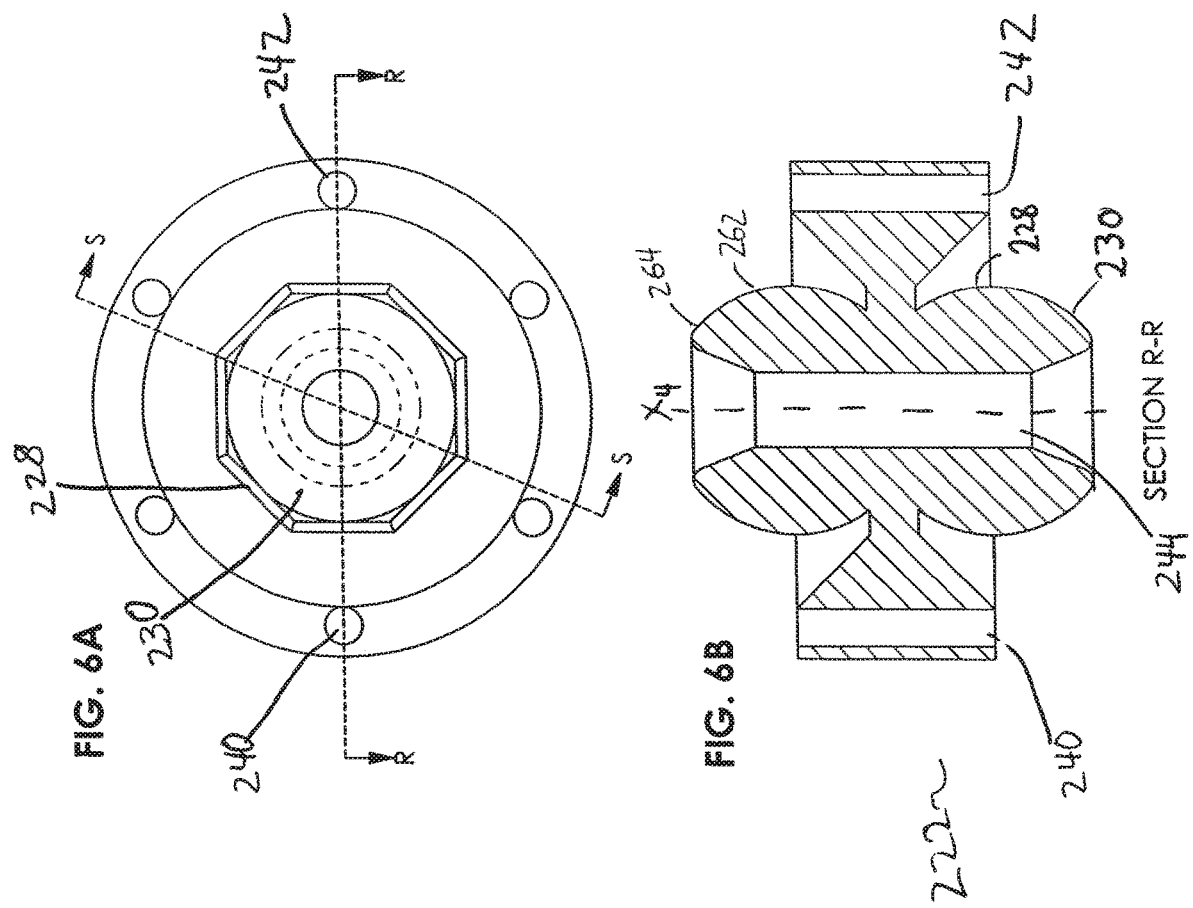

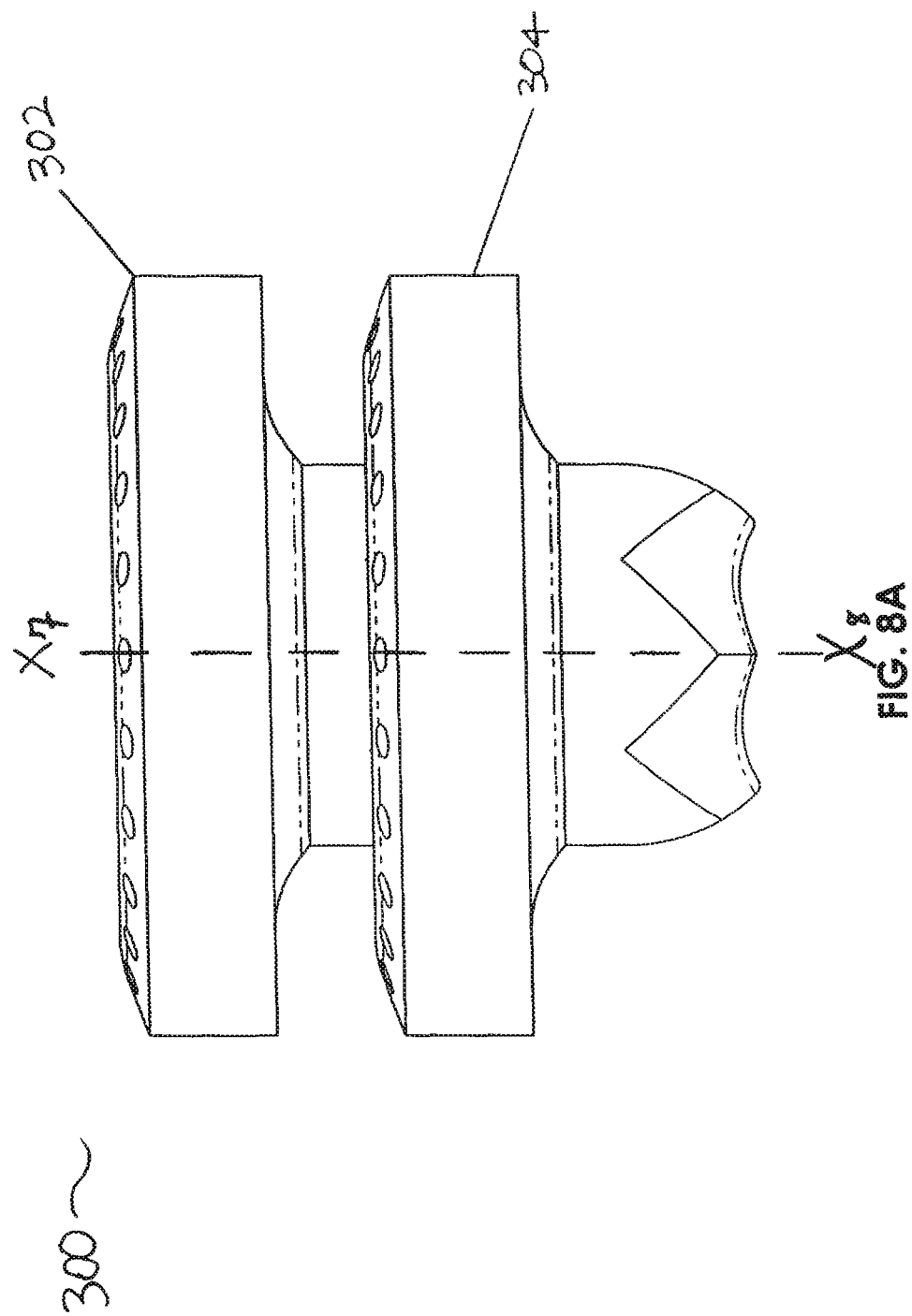

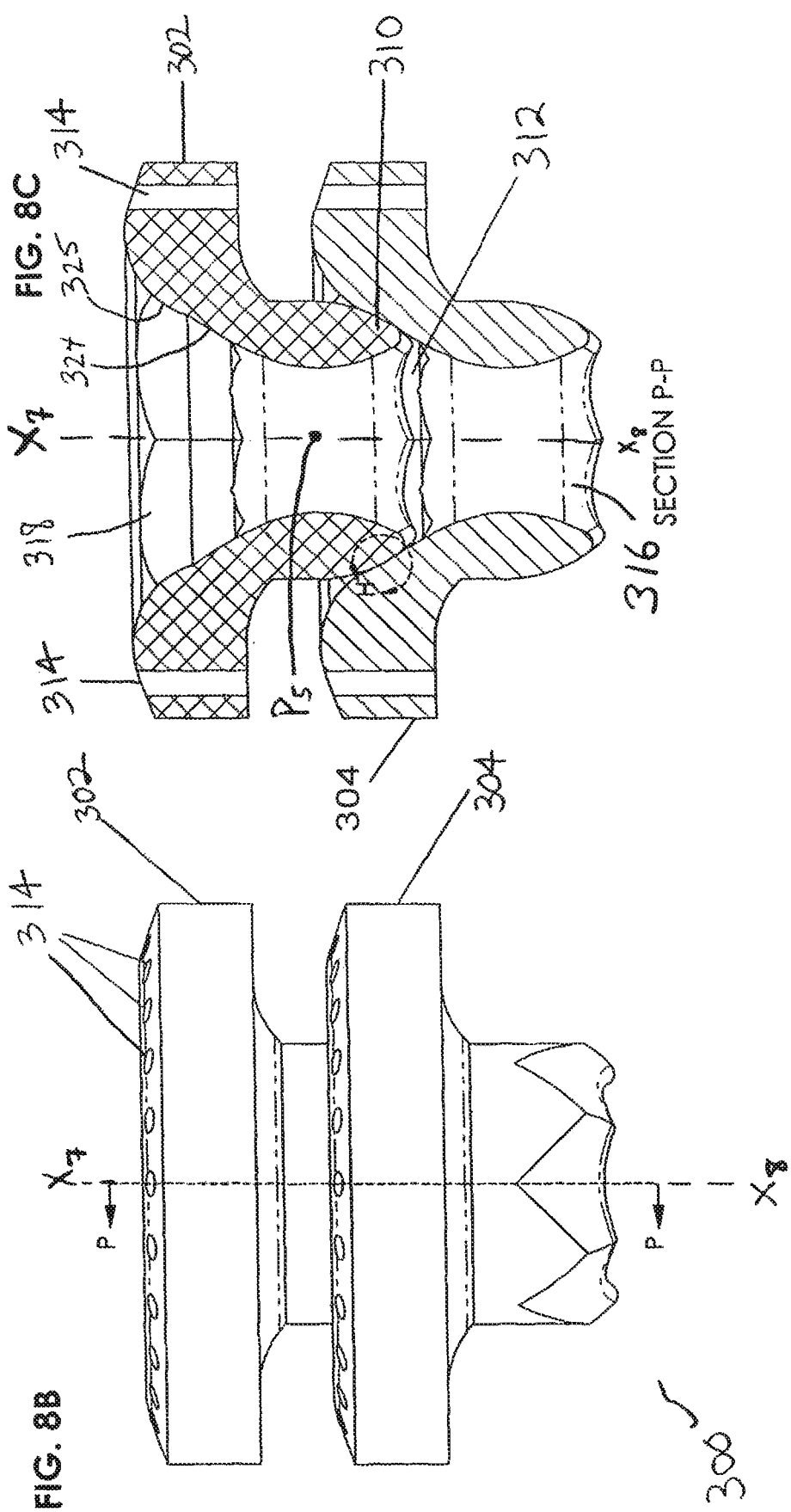

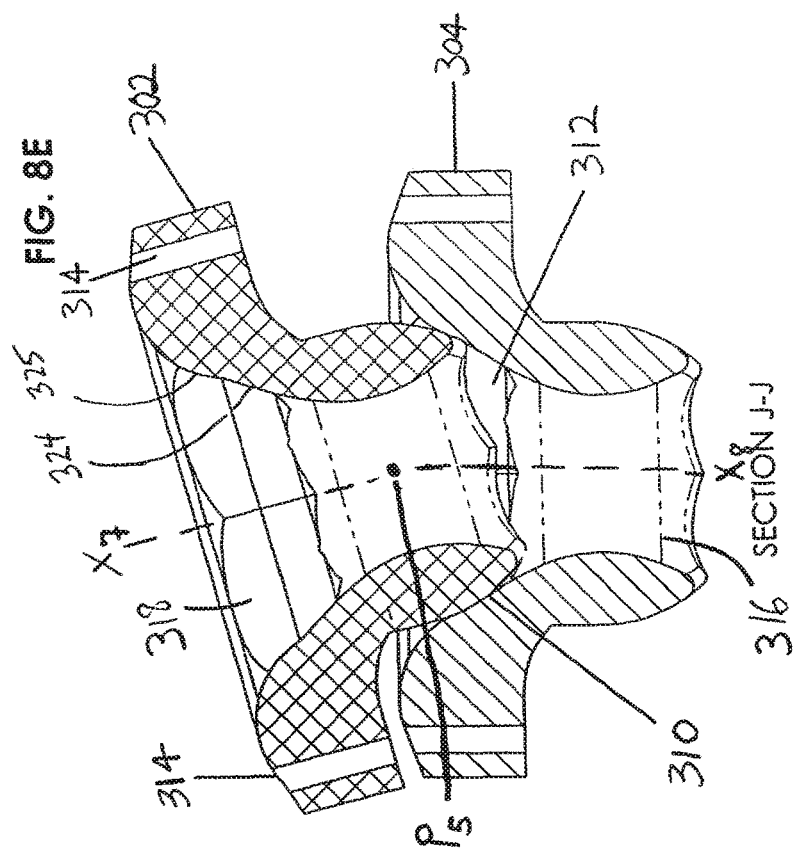
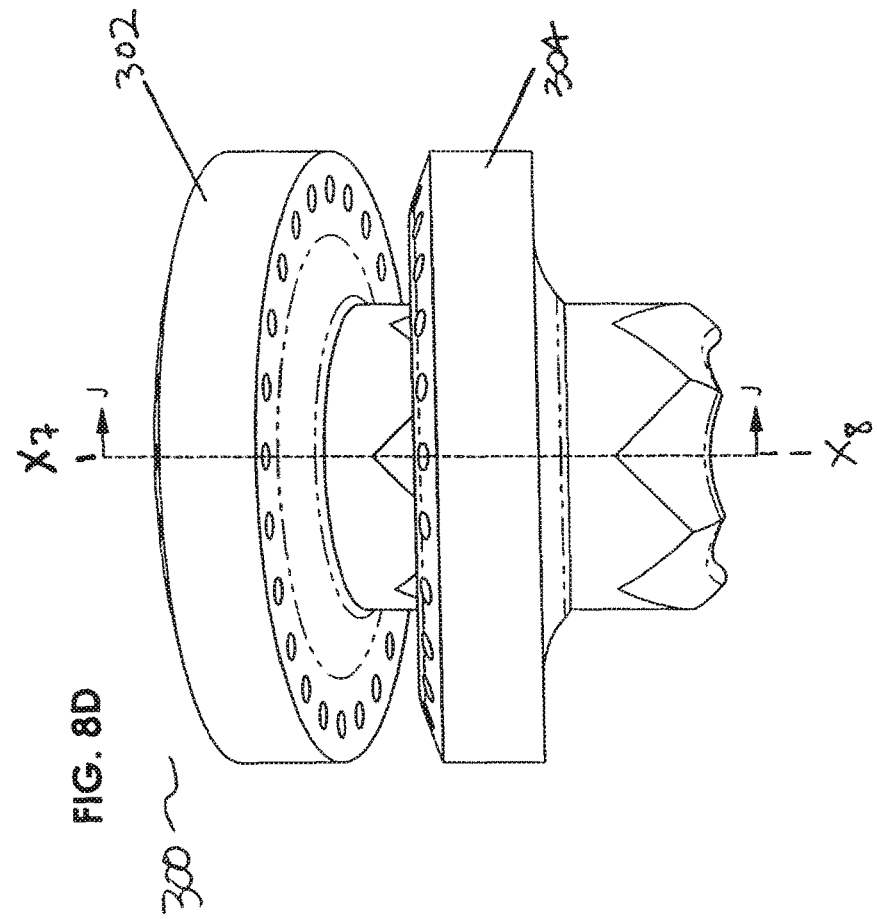

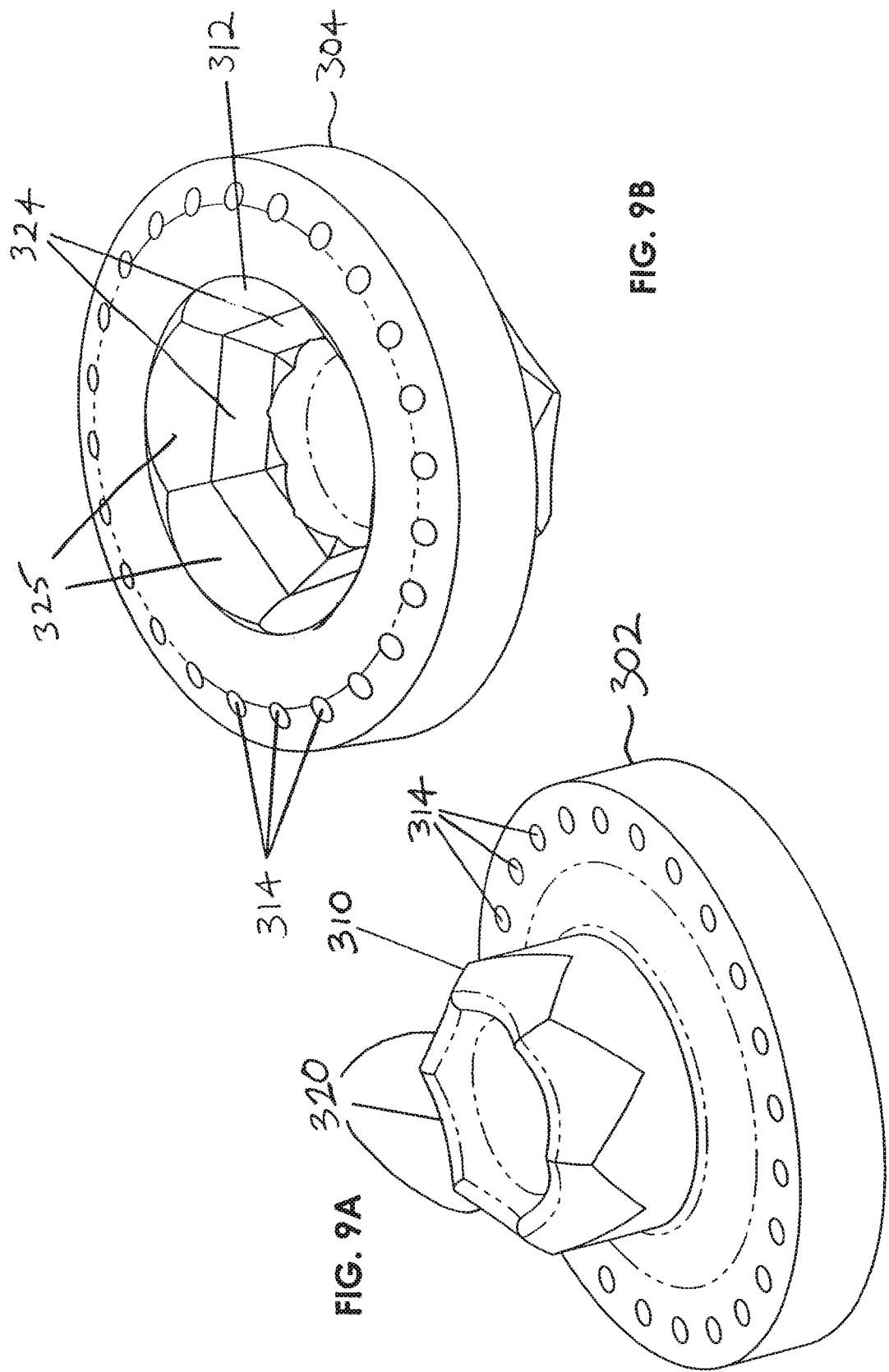

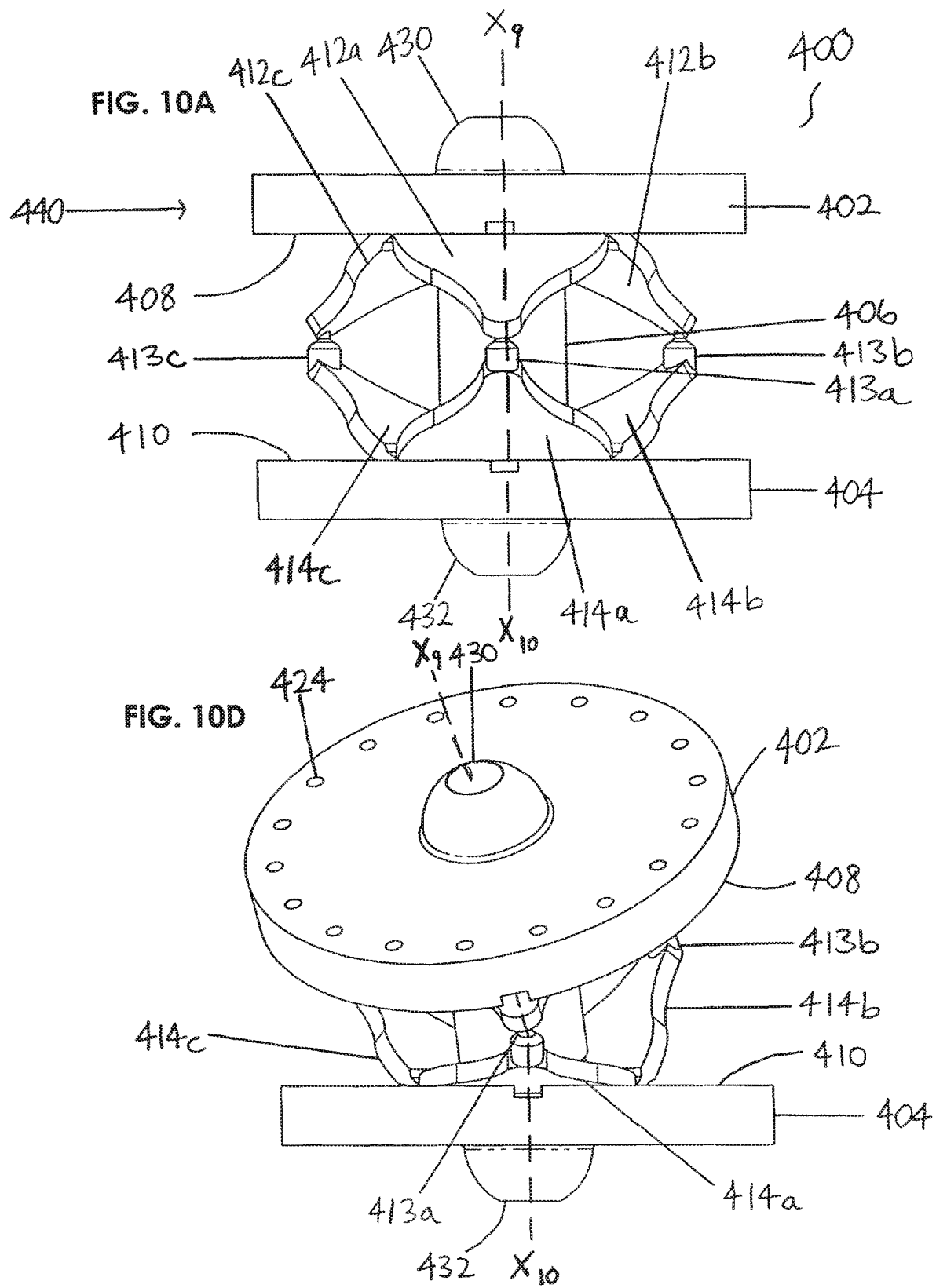

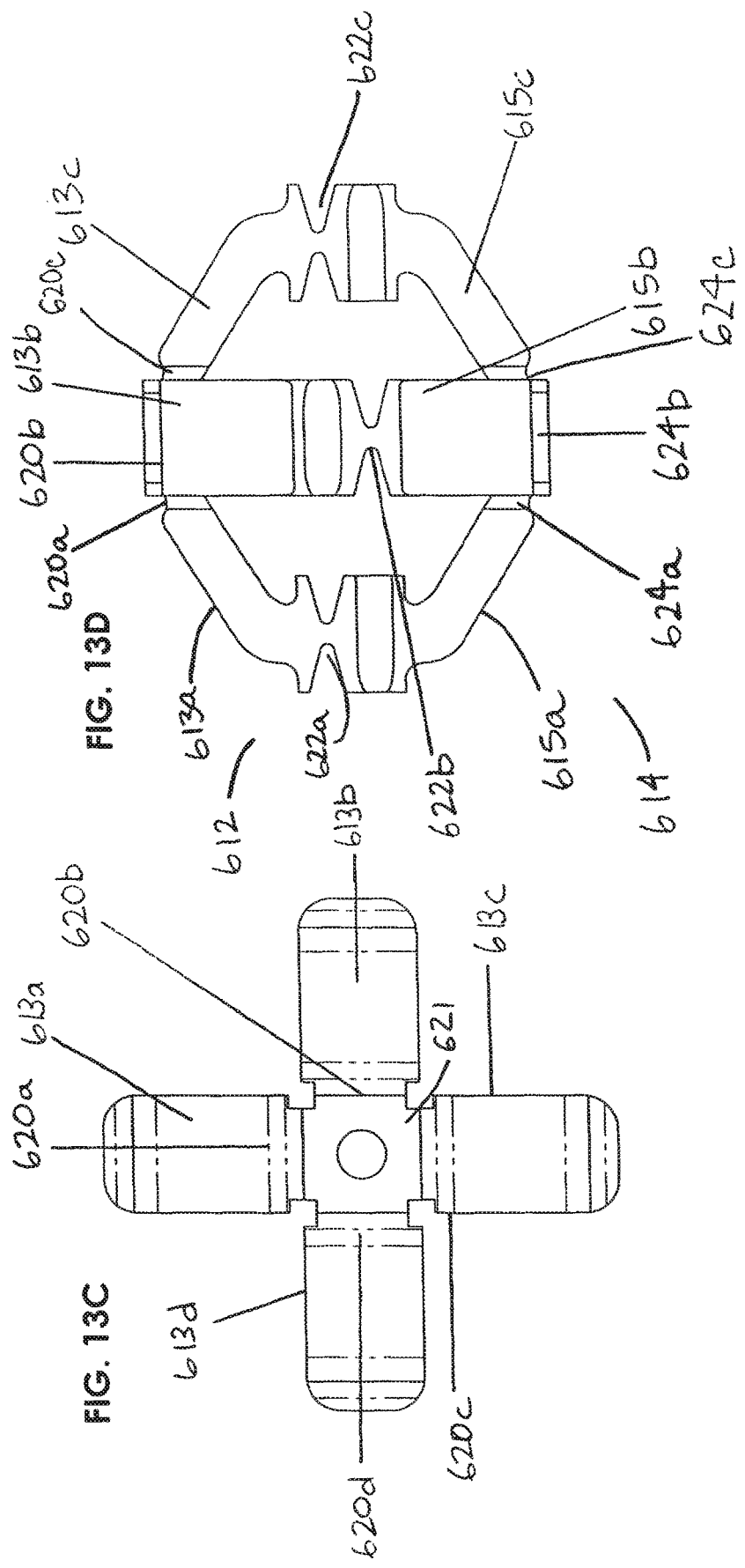

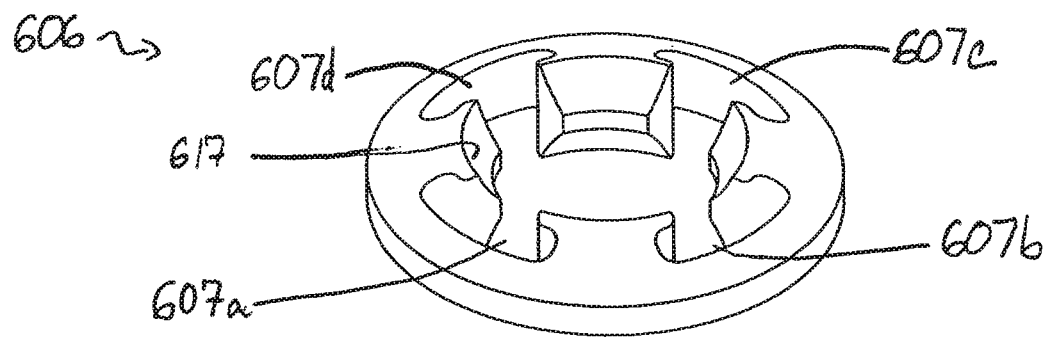

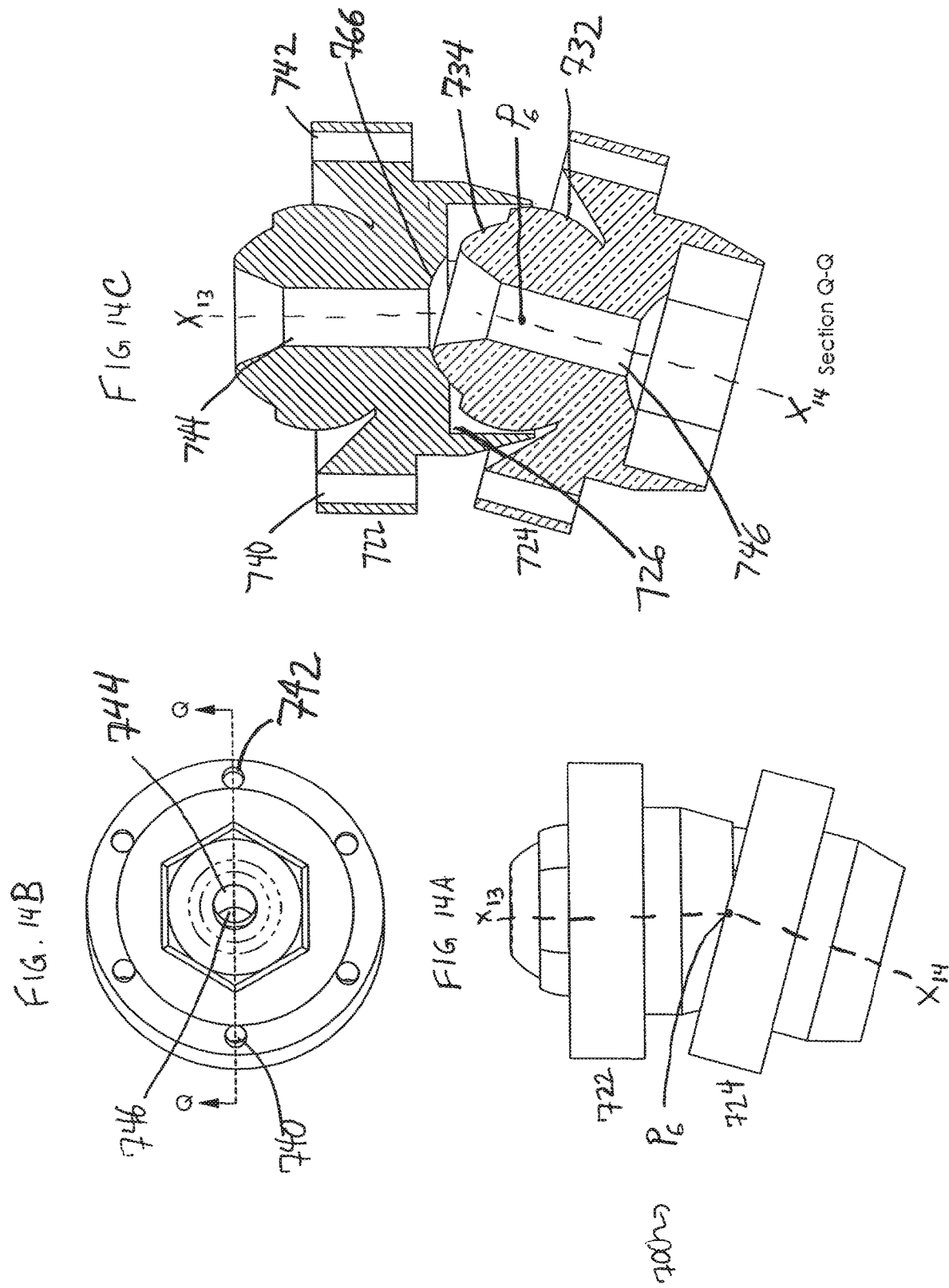

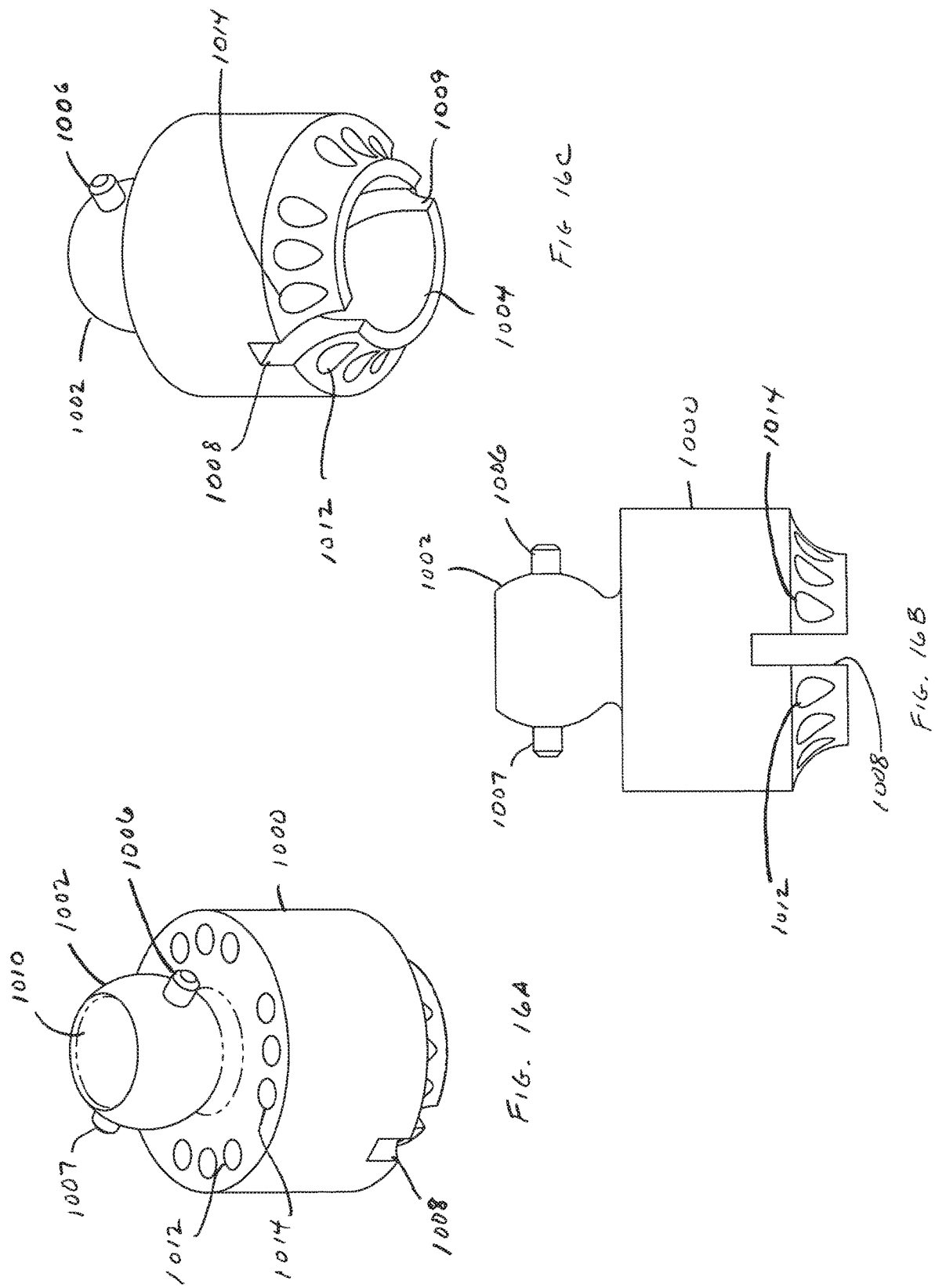

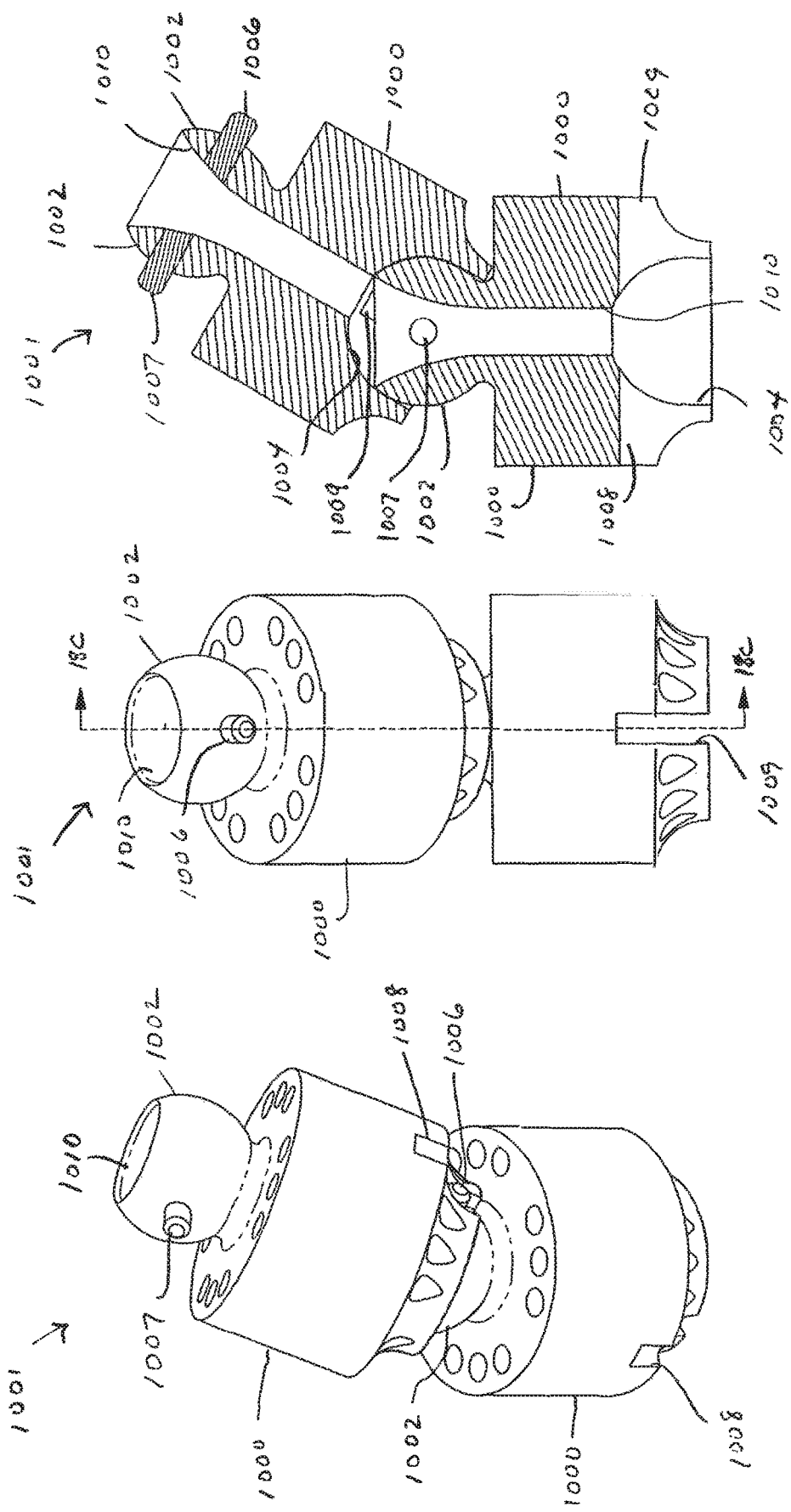

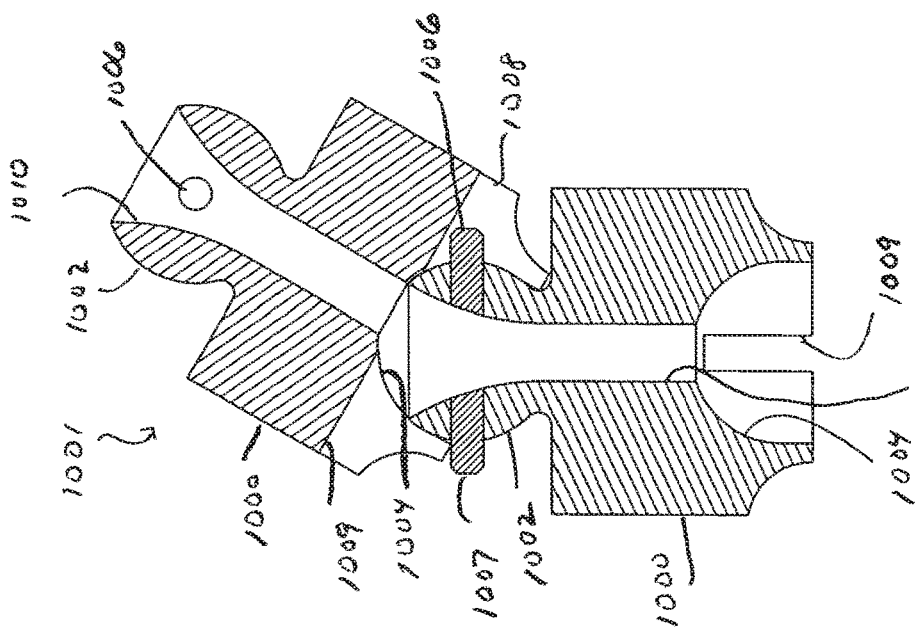
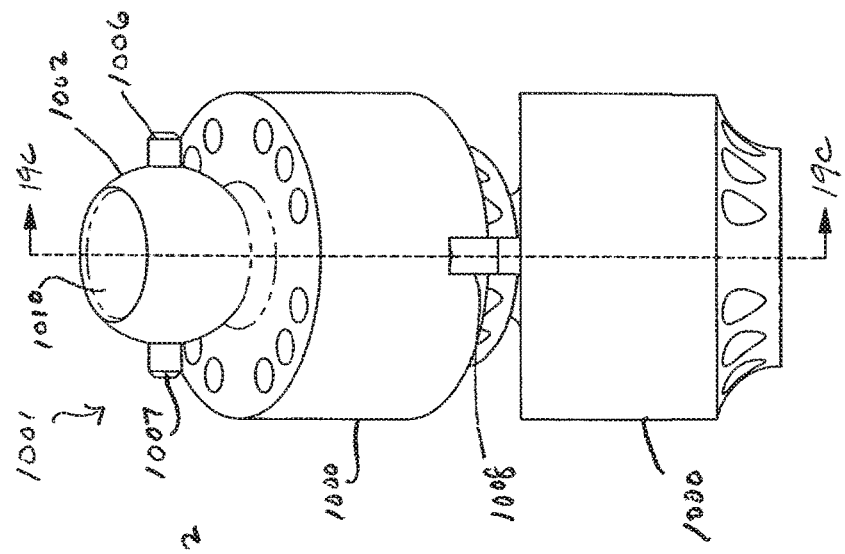
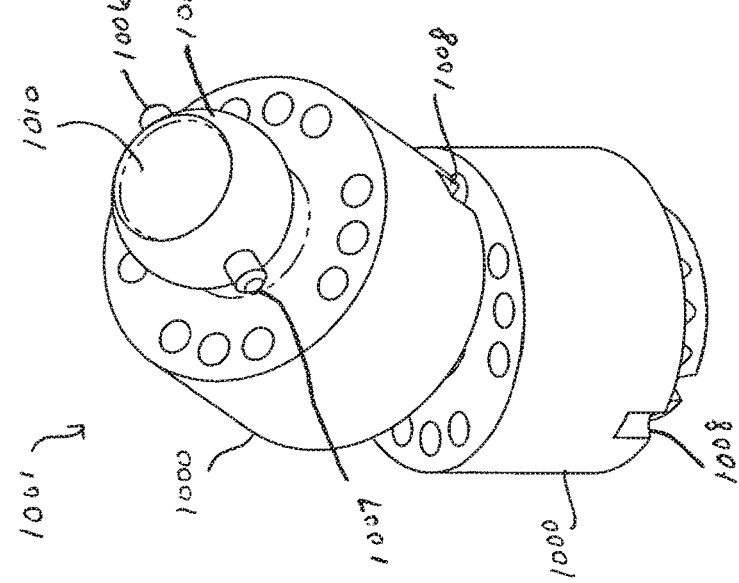

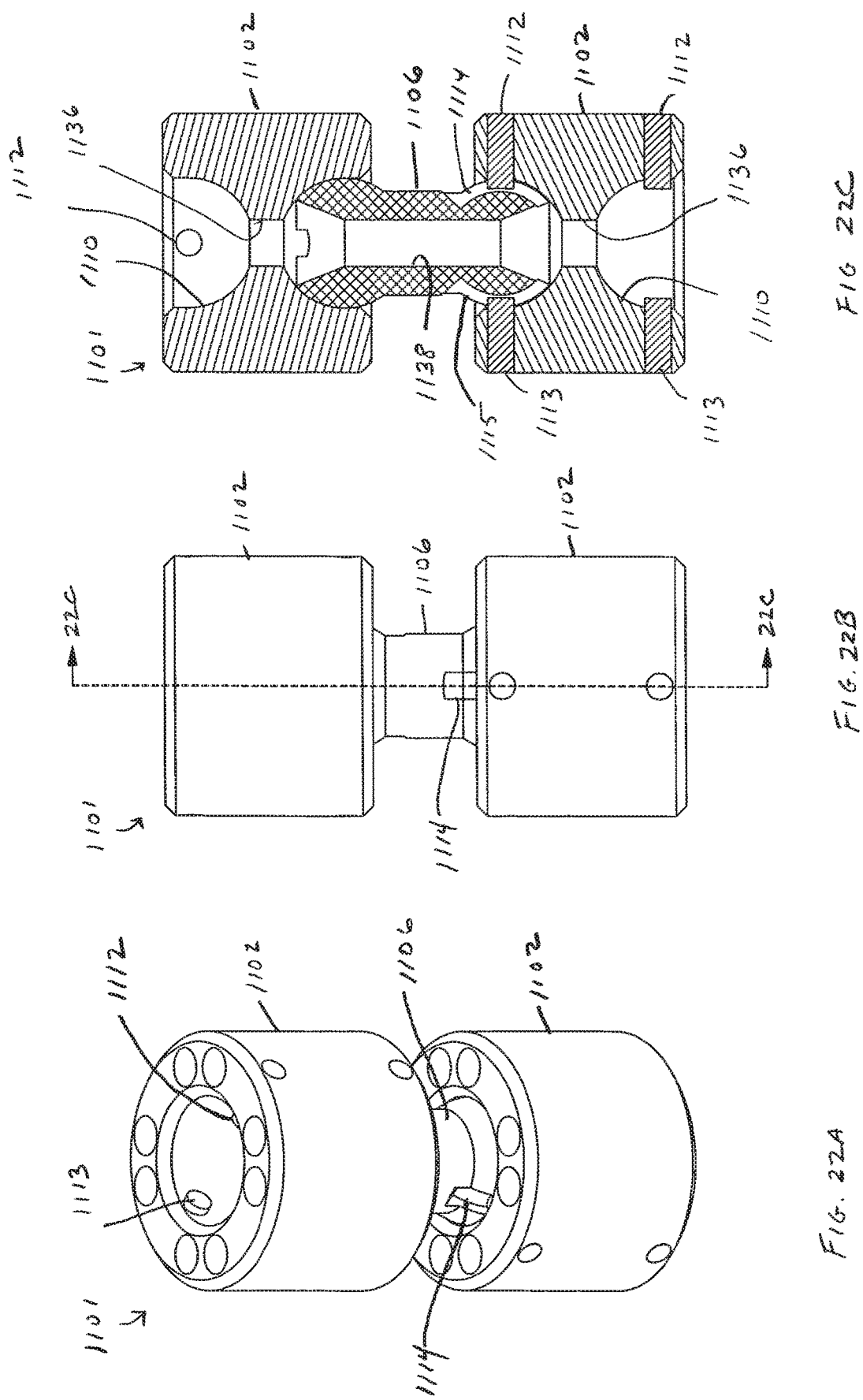

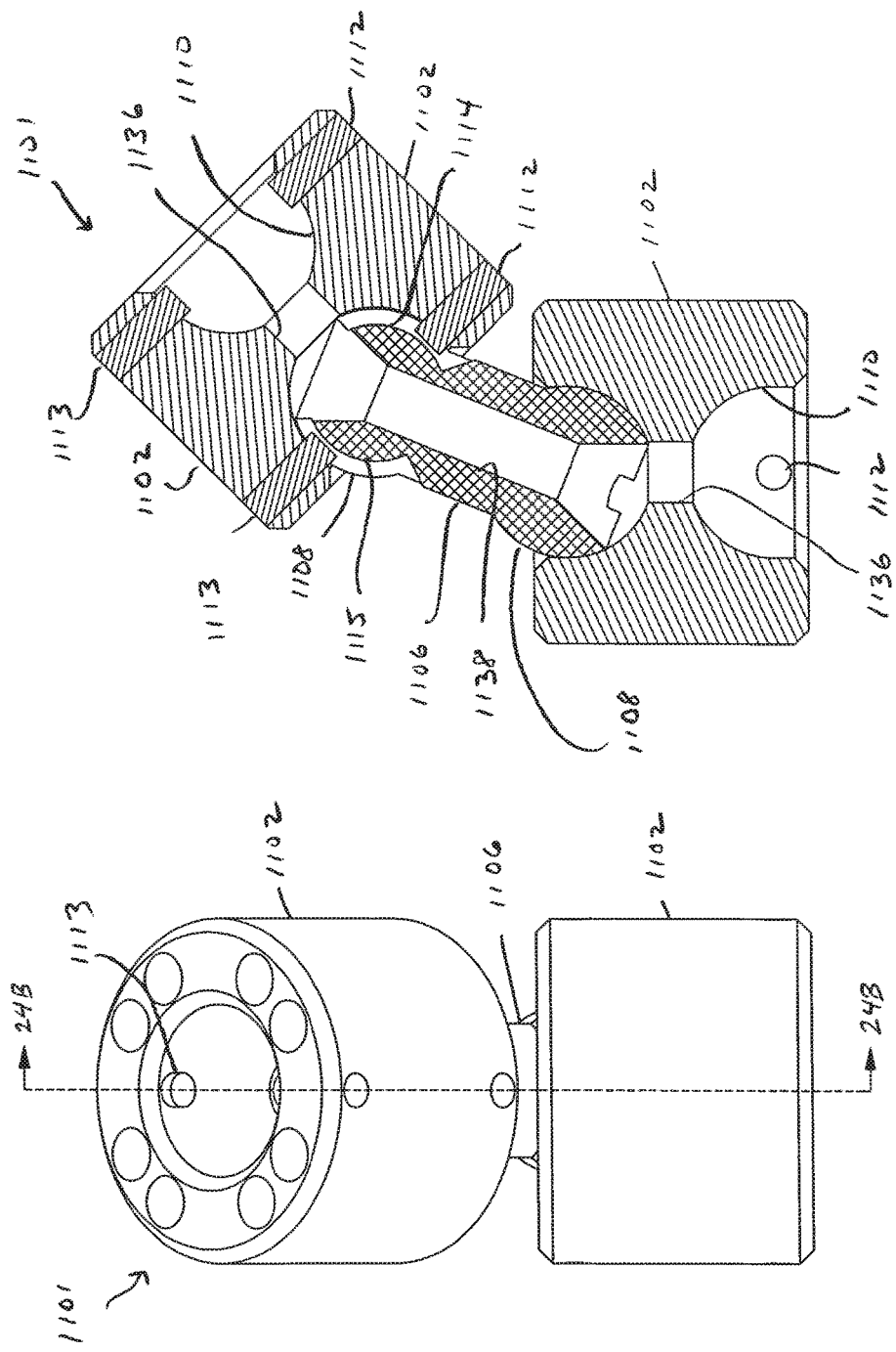

ARTICULATING MECHANISMS AND LINK SYSTEMS WITH TORQUE TRANSMISSION IN REMOTE MANIPULATION OF INSTRUMENTS AND TOOLS

CROSS-REFERENCE TO RELATED APPLICATIONS

This application is a division of U.S. patent application Ser. No. 11/122,598, filed May 4, 2005, which is a continuation-in-part of U.S. patent application Ser. No. 10/997,372 filed Nov. 23, 2004, now issued as U.S. Pat. No. 9,700,334, all the contents of which are hereby incorporated by reference herein in their entirety.

FIELD OF THE INVENTION

This invention relates to link systems and applications thereof, including the remote guidance and manipulation of instruments and tools.

BACKGROUND

The ability to easily remotely steer, guide and/or manipulate instruments and tools is, of interest in a wide variety of industries and applications, in particular where it is desired to navigate an instrument or tool into a workspace that is not easy to manually navigate by hand or that might otherwise present a risk or danger. These can include situations where the targeted site for the application of a tool or instrument is difficult to access, e.g., certain surgical procedures, the manufacture or repair of machinery, or even commercial and household uses, where manual access to a targeted site is restricted or otherwise. Other situations can include e.g., industrial applications where the work environment is dangerous to the user, such as workspaces exposed to dangerous chemicals. Still other situations can include e.g., law enforcement or military applications where the user may be at risk, such as deployment of a tool or instrument into a dangerous or hostile location.

Using surgical procedures as an illustrative example, procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward and retracted by pulling it back. The tip of the tube may be directed by twisting and general up/down and left/right movements. Oftentimes, this limited range of motion makes it difficult to negotiate acute angles (e.g., in the recto sigmoid colon), creating patient discomfort and increasing the risk of trauma to surrounding tissues. Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures. Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780. to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato). U.S. Pat. No. 5,916,147 to Boury et al. discloses a steerable catheter having four wires that run within the catheter wall. Each wire terminates at a different part of the catheter. The proximal ends of the wires extend loosely from the catheter so that the physician may pull them. The physician is able to shape and steer the catheter by selectively placing the wires under tension.

Although each of the devices described above is remotely steerable, the range of motion is generally limited. Moreover, it is difficult to transmit torque between links by rotating the device around the central axes of each link in such devices while still allowing components to pivot with respect to one another. Consequently, it would be advantageous for such a device to be capable of transferring torque about the central axis of each link, while preserving the capability of components to pivot with respect to each other. Further, it would be advantageous for components of such a device to pivot with respect to each other instead of moving laterally relative to each other (i.e. parallelogramming). Still further, it would be advantageous for such a device to have a locking mechanism capable of preventing movement of the device. Such a device would have widespread application in guiding, steering, and/or manipulating instruments and tools across numerous industries. Such a device would also of itself have entertainment, recreational, and educational value.

BRIEF SUMMARY OF THE INVENTION

The present invention provides for articulating mechanisms, link systems, and components thereof, useful for a variety of purposes including, but not limited to, the remote manipulation of instruments such as surgical or diagnostic instruments or tools. Such surgical or diagnostic instruments or tools include but are not limited to endoscopes, light sources, catheters, Doppler flow meters, microphones, probes, retractors, pacemaker lead placement devices, dissectors, staplers, clamps, graspers, scissors or cutters, ablation or cauterizing elements, and the like. Other instruments or tools in non-surgical applications include but are not limited to graspers, drivers, power tools, welders, magnets, optical lenses and viewers, light sources, electrical tools, audio/visual tools, lasers, monitors, and the like. Depending on the application, it is contemplated that the articulating mechanisms, link systems, and other components of the present invention can be readily scaled to accommodate the incorporation of or adaptation to numerous instruments and tools. The link systems and articulating mechanism may be used to steer these instruments or tools to a desired target site, and can further be employed to actuate or facilitate actuation of such instruments and tools.

In one aspect of the invention, an articulating link system capable of transmitting torque is provided. The link system includes a plurality of links and at least two adjacent links. The first adjacent link has a torque-conferring protrusion, at least a portion of which has a non-circular latitudinal circumference. A bushing interposed between the two adjacent links engages the torque-conferring protrusion. The link system thus provides torque transmission between the links while allowing for pivoting movement of the first adjacent link relative to the second adjacent link. In certain variations, the portion of the protrusion having a non-circular latitudinal circumference is curved along the longitudinal circumference. The first adjacent link can further include a ball section with a curved latitudinal circumference. The bushing can include a socket configured to receive the ball section. The non-circular latitudinal circumference of the torque conferring protrusion can have a plurality of radially distributed faces. The faces can be curved along the longitudinal circumference. Alternatively; both links have a torque-conferring protrusion and/or ball section, as described above.

In another aspect of the invention, an articulating link system is provided that is capable of transmitting torque without a bushing. The link system includes a plurality of links. A first adjacent link has a torque-conferring protrusion at least a portion of which has a non-circular latitudinal circumference. A second adjacent link has a socket configured to engage the torque-conferring protrusion of the first adjacent link. The link system provides for torque transmission between the links, while allowing for pivoting movement of the first link relative to the second link. In certain variations, the surface of the torque-conferring protrusion is curved along a longitudinal circumference. In another variation, the first adjacent link further includes a ball section having a curved latitudinal circumference. In yet another variation, the non-circular latitudinal circumference of the torque-conferring protrusion includes a plurality of radially distributed, longitudinally curved faces. In another variation, the socket of the second adjacent link has a plurality of radially distributed curved faces configured to engage the torque-conferring protrusion of the first adjacent link.

In another aspect, an articulating link system is provided that includes a plurality of links with at least two adjacent links. A plurality of tabs is disposed on the first adjacent link. The second adjacent link is operably connected to the tabs of the first adjacent link. The link system provides torque transmission between the links while allowing for pivoting movement of the first adjacent link relative to the second adjacent link.

In one embodiment, the tabs include a first set of tabs and a second set of tabs. The first set of tabs is disposed from the surface of the first adjacent link. The second set of tabs is disposed from the surface of the second adjacent link. Pairs of tabs, one from each set, are connected together in a two degree of freedom joint. In a further variation, a bushing may be disposed between the adjacent links.

In another embodiment, the first adjacent link has a plurality of radially dispersed depressions. The plurality of tabs associated with each link is radially dispersed from the central axes of each link of the articulating link system such that each tab engages one radially dispersed depression of the link. In one variation, the articulating link system further includes a bushing disposed between each of the two adjacent links.

In another variation, each tab on the first link is operably connected to a groove disposed radially on the second link, such that the terminus of each tab can move within the groove.

In yet another aspect of the invention, articulating link systems are provided that are capable of transmitting torque where the link system uses ball and socket interfaces that include engaging pins and reciprocal surfaces. One such system includes adjacent links, where a first adjacent link has a ball and a second adjacent link has a socket for receiving the ball, and where the ball and socket include at least one engaging pin and reciprocal surfaces that provide for torque transmission between the links while also allowing for pivoting movement of the first link relative to the second link. Another such system includes at least two adjacent links with a bushing disposed between the adjacent links. The adjacent links can include balls and/or sockets, with the bushing including corresponding sockets and/or balls that engage the balls or sockets of the links. The engaged balls and sockets include at least one engaging pin and reciprocal surfaces that provide for torque transmission between the links and bushing while allowing for pivoting movement of the first adjacent link relative to the second adjacent link. The reciprocal surfaces are typically arranged such that torque transmission can occur in either rotational direction (i.e., clockwise and counter-clockwise). In a simple variation, the reciprocal surfaces can be provided as the opposing faces of a reciprocal slot, with an engaging pin disposed in the slot. In other variations, two separate engaging pins can engage separate reciprocal surfaces, provided again that the reciprocal surfaces are oriented such that torque can be transmitted from one pin or the other pin in either rotational direction (i.e., clockwise and counter-clockwise).

In a further aspect of the invention, an articulating mechanism is provided for, e.g., remote manipulation of a surgical or diagnostic tool. The articulating mechanism can include one or more link systems that allow for remote manipulation of a distally located tool or instrument. In one variation, an articulating mechanism is provided that includes at least one pair of links, each link being maintained in a spaced-apart relationship relative to the other link of the pair. In another variation, an articulation mechanism is provided that includes multiple pairs of links. The articulating mechanism further includes at least one set of cables, each set connecting the links of a discrete pair to one another such that movement of one link of a pair causes corresponding relative movement of the other link of the pair. Alternatively, the articulating mechanism can include multiple sets of cables. The articulating mechanism thus provides torque transmission between adjacent links while allowing for pivoting movement.

In a further aspect of the invention, a surgical device is provided that includes a surgical or diagnostic tool and a plurality of links proximal of the surgical or diagnostic tool. An elongate shaft is proximal of the plurality of links. In certain variations one or more cables are distally connected to one or more links and received proximally through the elongate shaft. Movement of one or more cables causes movement of one or more links. The surgical device may include any of the link systems discussed above. Depending on the application, the shaft can have varying stiffness of flexibility and be of varying length.

In other aspects of the invention, a tool or instrument may be attached to and extend from the link systems and/or articulating mechanisms, or the link systems and/or articulating mechanisms may be otherwise incorporated into such instruments or tools. In the case of surgical applications, examples of surgical or diagnostic tools include, but are not limited to, endoscopes, light sources, catheters, Doppler flow meters, microphones, probes, retractors, pacemaker lead placement devices, dissectors, staplers, clamps, graspers, scissors or cutters, and ablation or cauterizing elements. For other applications, numerous tools or instruments are likewise contemplated, including, without limitation, graspers, drivers, power tools, welders, magnets, optical lenses and viewers, electrical tools, audio/visual tools, lasers, monitors, light sources, and the like. The types of tools or instruments, methods and locations of attachment, and applications and uses include, but are not limited to, those described in pending and commonly owned U.S. application Ser. Nos. 10/444,769, 10/948,911, and 10/928,479, each of which is incorporated herein by reference in its entirety.

BRIEF DESCRIPTION OF THE DRAWINGS

FIG. 1C shows a top view of the embodiment of FIG. 1A;

FIG. 2C shows another side view of the link system shown in FIG. 2A rotated by 90° about axes $X_1$ and $X_2$ from the view depicted in FIG. 2A;

FIG. 2D shows a cross-sectional view of the link system of FIG. 2C taken along the plane designated by line K-K;

FIG. 3A shows a side view of a link system similar to the distal link system of the embodiment depicted in FIG. 1A;

FIG. 3B shows a different side view of the link system of FIG. 3A rotated by 90° about axis $X_5$ from the view depicted in FIG. 3A;

FIG. 3C shows a cross-sectional view of the device depicted in FIG. 3A taken along the plane designated by line M-M;

FIG. 3D shows a cross-sectional view of the device depicted in FIG. 3C taken along the plane designated by line AB-AB;

FIG. 4A shows a side view of the link system of FIG. 2A in a bent conformation;

FIG. 4B shows a cross-sectional view of the device depicted in FIG. 4A taken along the plane designated by line Y-Y;

FIG. 6A shows an end view of a single link, according to another embodiment of the invention, with an octagonal torque-conferring protrusion;

FIG. 6B shows a cross-sectional view of the link depicted in FIG. 6A taken along the plane designated by line R-R;

FIG. 6C shows a cross-sectional view of the link depicted in FIG. 6A taken along the plane designated by line S-S;

FIG. 8A shows a side view of a hex-socket articulating link system in a straight conformation according to an embodiment of the invention;

FIG. 8B shows another side view of the hex-socket articulating link system of FIG. 8A rotated by 90° about axes $X_7$ and $X_8$ from the view depicted in FIG. 8A;

FIG. 8C shows a cross-sectional view of the articulating link system depicted in FIG. 8B taken along the plane designated by line P-P;

FIG. 8D shows a side view of the hex-socket articulating link system of FIG. 8B in a bent conformation;

FIG. 8E shows a cross-sectional view of the articulating link system depicted in FIG. 8D taken along the plane designated by line J-J;

FIGS. 9A AND 9B show perspective views of a single link of the hex-socket articulating link system of FIG. 8A;

FIG. 10A shows a side view of a link system in a straight conformation, according to another embodiment of the invention;

FIG. 10D shows a side view of the link system of FIG. 10A in a bent conformation;

FIG. 13C shows a top view of two sets of tabs from the link system of FIG. 13A;

FIG. 13D shows a side view of two sets of tabs from the link system of FIG. 13A;

FIG. 13E shows a perspective view of a bushing used in the link system of FIG. 13A;

FIG. 14A shows a perspective view of a link system, according to another embodiment of the invention;

FIG. 14B shows a top view of the link system depicted in FIG. 14A;

FIG. 14C shows a cross-sectional view of the link system depicted in FIG. 14B, taken along the plane designated by line Q-Q;

FIG. 16A shows a perspective view of a link according to another embodiment of the invention;

FIG. 16B shows a side view of the link of FIG. 16A;

FIG. 16C shows another perspective view of the link of FIG. 16A;

FIGS. 18A, 18B and 18C show perspective, side, and cross-sectional views, respectively, of a link assembly formed of the links of FIG. 16A, in a bent conformation;

FIGS. 19A, 19B and 19C show perspective, side, and cross-sectional views, respectively, of a link assembly formed of the links of FIG. 16A, in another bent conformation;

FIGS. 22A, 22B and 22C show perspective, side, and cross-sectional views, respectively, of a link assembly formed of the links and bushing of FIGS. 20A and 21A, in an unbent conformation;

FIGS. 24A and 24B show side, and cross-sectional views, respectively, of a link assembly of FIG. 22A, in another bent conformation

DETAILED DESCRIPTION OF THE INVENTION

Figure 1A:
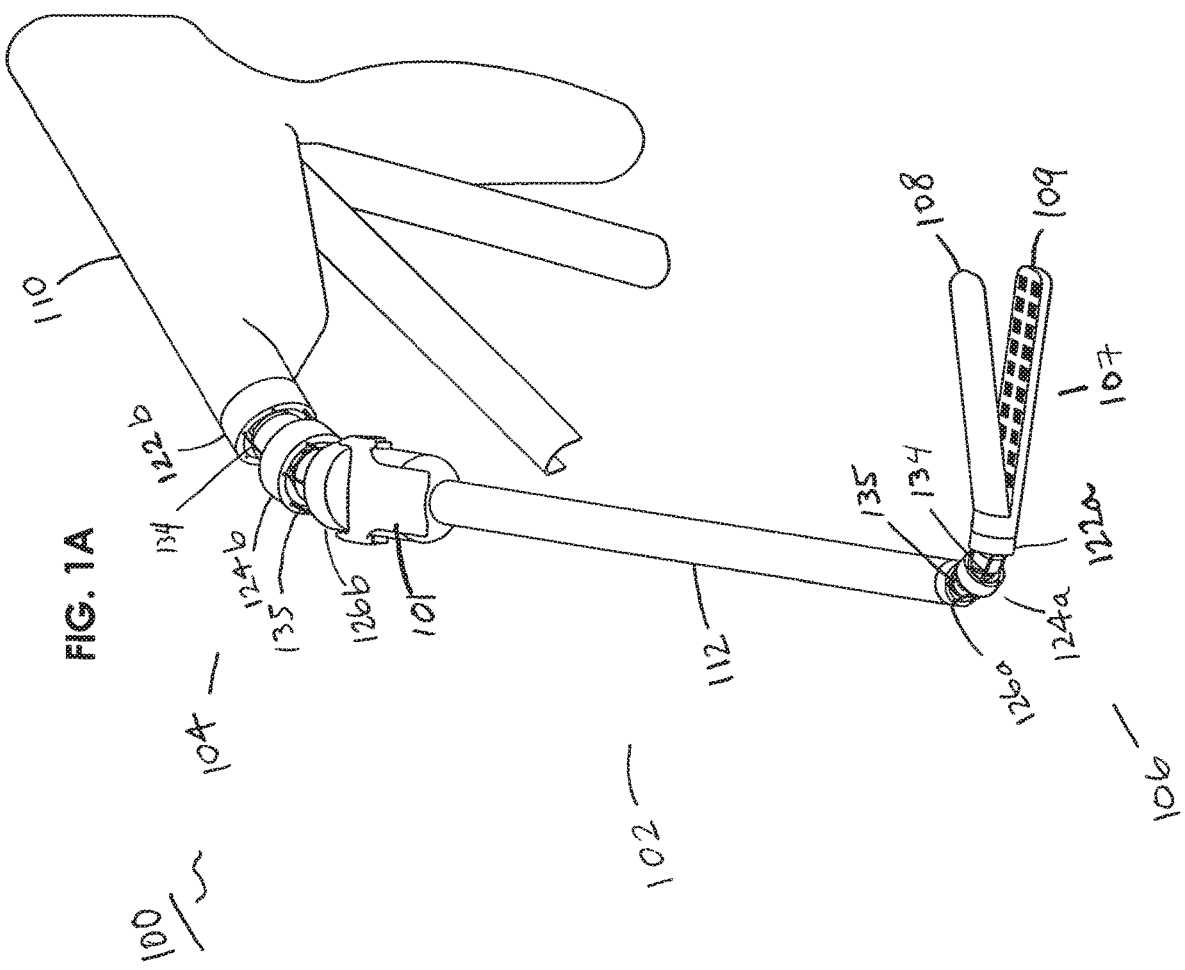
FIG. 1A shows a perspective view of a surgical stapler device according to one embodiment of the invention, with proximal and distal articulating link systems.

As further detailed herein, articulating link systems and mechanisms are provided that can form, or be incorporated into, or otherwise constitute, a wide variety of devices. The link systems may be made from a combination of individual links. Articulating mechanisms according to the invention generally include at least one pair of links and at least one set of cables connecting at least one discrete pair of links. Alternatively, articulating mechanisms can include multiple pairs of links and/or multiple sets of cables connecting at least one discrete pair of links. The term "link" as used herein refers to a discrete portion of a link system or articulating mechanism that is capable of movement relative to another discrete portion of the mechanism or system. In some embodiments, the link may correspond to another discrete portion or defined area at the opposite end of the mechanism. Links typically have at least a cylindrical portion. The links are generally aligned along the central axes of each link of the mechanism. In certain embodiments, the link systems will include a plurality of links. In certain other embodiments, at least two adjacent links can be separated by a bushing.

The link systems can form or be incorporated into a variety of articulating mechanisms. In various embodiments, articulating mechanisms according to the invention generally include at least one pair of links and at least one set of cables. In other variations, an articulation mechanism is provided that includes multiple pairs of links and/or multiple sets of cables. In further embodiments, the articulating mechanism includes a plurality of links or segments that are members of discrete pairs. The links form a proximal end and a distal end, with one link of each pair being situated in a link system at the proximal end and the other link of the link pair in a link system at the distal end.

In such articulating mechanisms, each cable set connects the links of a discrete pair in the articulating mechanism to one another so that movement of one link of a pair causes a corresponding movement of the other link in the pair. As used herein, the term "active link" or "active link pair" refers to links that are directly connected to one another by a cable set. The term "spacer link" or "spacer link pair" refers to links that are not directly connected by a cable set. Spacer links can nevertheless be disposed between active links and provide for the passage of cable sets that connect active links. The ability to manipulate active link pairs allows for the mechanism to readily form complex three-dimensional configurations and geometries as is further detailed herein. With conventional articulating devices that rely on a cable set or wire that passes through otherwise unconnected links, it is difficult to obtain such complex geometries because such devices are typically designed such that the steering cables or wires pass through each link and terminate at a distal-most link. Thus, all the segments bend together in a coordinated response to movement of the wire or cable set, typically in a curved or arcuate fashion.

The link systems or articulating mechanisms of the present invention may, for example, be incorporated into devices used to direct and steer a surgical or diagnostic instrument tool to a target site within a body region of a patient. The device can be introduced either in its native, straight configuration, or after undergoing various manipulations at its proximal end from a location outside the patient. In various embodiments, link systems form a part or parts of an articulating mechanism. Movement of the proximal end of the mechanism results in movement at the distal end. Further, the resulting directional movement of the distal end can be inverted, mirrored, or otherwise moved, depending on the degree of rotation of the proximal end relative to the distal end. Also, to control the steering and manipulation of the distal end the proximal end provides for a user interface that is convenient and easy to use. This user interface allows, for example, a user to readily visualize the shape and directional movement of the distal end of the mechanism that is located, e.g., within a patient, based on the manipulated shape of the externally positioned proximal end user interface. Alternatively, control or actuation of the distal end links can be accomplished by more conventional methods of manipulating the link actuating. cables, e.g., through the use of knob-and-pulley systems and the like.

In addition to the formation of complex configurations, the present invention also allows for increased rigidity of the mechanism by constraining manipulated active links and allowing such links to resist movement due to laterally applied forces. A given link pair is considered fully constrained if upon manipulating the links to achieve the desired shape and fixing one link of the pair in that desired shape, the other link of the pair can resist loads while maintaining its desired, unloaded shape. For links that are otherwise free to move in three degrees of freedom, a minimum of three cables are required to fully constrain the links. This is not always the case with conventional articulating devices. Spacer links will not be so constrained, and the inclusion of such unconstrained links may be advantageous in many situations where it is desirable to have portions of the actuated mechanism be less rigid.

The terms "instrument" and "tool" are herein used interchangeably and refer to devices that are usually handled by a user to accomplish a specific purpose. For purposes of illustration only, link systems and articulating mechanisms of the invention will be described in the context of use for the remote guidance, manipulation, and/or actuation of surgical or diagnostic tools and instruments in remotely accessed regions of the body. As previously noted, other applications of the link systems and articulating mechanisms besides surgical or diagnostic applications are also contemplated. Generally, any such application will include any situation where it is desirable to navigate an instrument or tool into a workspace that is not easy to manually navigate by hand or that might otherwise present a risk or danger. These include, without limitation, industrial uses, such as for the navigation of a tool, probe, sensor, etc. into a constricted space, or for precise manipulation of a tool remotely, for the assembly or repair of machinery. The device can also be used to turn e.g. a screw, whether in the straight or bent configuration. These can also include commercial and household situations where the targeted site for the application of a tool or instrument is difficult to access. Other situations can include, e.g., industrial applications where the work environment is dangerous to the user, for example, workspaces exposed to dangerous chemicals. Still other situations can include, e.g., law enforcement or military applications where the user may be at risk, such as deployment of a tool or instrument into a dangerous or hostile location. Yet other uses include applications where simple remote manipulation of complex geometries is desirable. These include uses in recreation or entertainment, such as toys or games, e.g., for remote manipulation of puppets, dolls, figurines, and the like.

Figure 1B:
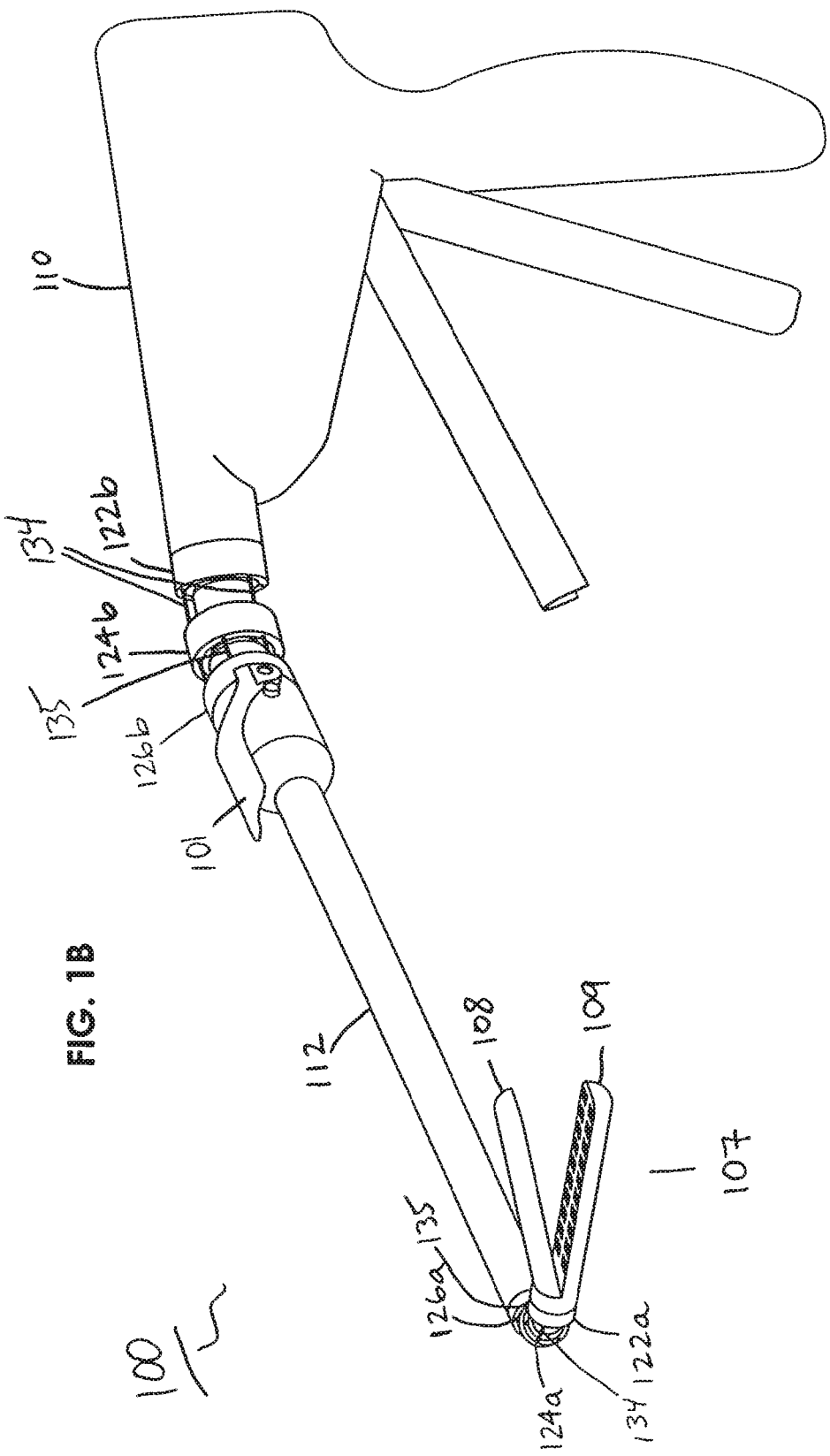
FIG. 1B shows a second perspective view of the embodiment of FIG. 1A.

With reference to FIGS. 1A-C, an embodiment of the invention is depicted which incorporates an articulating mechanism and link system according to the invention. As shown in FIG. 1A, surgical stapler 100 includes an articulating mechanism 102 having a proximal link set 104 and corresponding distal link set 106, separated by elongated shaft 112, which both maintains the proximal and distal link sets in a spaced-apart relationship and also provides a working shaft for advancing the stapler. Stapler tool 107 with jaws 108, 109 is attached to the distal end of distal link set 106 and is operationally connected to stapler handle 110, which is attached to the proximal end of proximal link set 104.

Surgical stapler 100 as configured is suitable for laparoscopic use. Surgical stapler 100 can be substituted with any surgical stapler known in the art, including, for example, staplers disclosed in U.S. Pat. Nos. 6,250,532, 6,644,532 B2, 5,704,534, and 5,632,432, incorporated herein by reference in its entirety. While this embodiment incorporates a stapler, it will be readily appreciated that a wide variety of surgical tools and instruments can be operationally attached to the distal end, including but not limited to endoscope, light source, catheter, Doppler flow meter, microphone, probe, pacemaker lead placement device, retractor, dissector, clamp, grasper, needle driver, scissors or cutter, or ablation or cauterizing elements, as well as other tools or instruments for non-surgical applications, as has been previously noted.

Proximal and distal link sets 104 and 106 include corresponding pairs of links, i.e., each individual link in proximal link set 104 is paired with an individual link in distal link set 106 to form a series of discrete pairs. Distal link set 106 include links 122a, 124a, and 126a, while proximal link set 104 include links 122b, 124b, and 126b. Links 122a and 122b, 124a and 124b, and 126a and 126b are discrete link pairs. The proximal links (122b, 124b, and 126b) are connected to the distal links (122a, 124a, and 126a) by sets of cables 134, 135 such that movement of proximal links in proximal link set 104 causes a corresponding relative movement of distal link set 106. In particular, links 122a and 122b are connected by cables 134, and links 124a and 124b are connected by cables 135, with links 126a and 126b integral to shaft 112. Links 122a and 122b, and links 124a and 124b, thus form active link pairs. Alternatively, links 122a and 122b are integral to the stapler tool 107 and stapler handle•110, respectively.

Stapler handle 110 is bent with respect to elongated shaft 112 and stapler tool 107. Link set 104 is bent, resulting in a bend between stapler handle 110 and elongated shaft 112. The bend of link set 104 causes a corresponding bend in link set 106. Stapler tool 107 can be bent up, down, left right, or rotated relative to the central axis of link 122a, even when the central axis of link 122a is not in line with the central axis of elongated shaft 112. Stapler handle is used to articulate stapler tool 107. Movement of stapler tool 107 relative to elongated shaft 112 can be accomplished simultaneously, allowing for smooth articulation and dynamic rotation of the stapler tool 107 in multiple degrees of freedom.

Generally speaking, one or more sets of cables are used to connect active link pairs of an articulating mechanism according to varying embodiments of the invention. As previously noted, each active link at one end of an articulating mechanism is connected to its corresponding link at the other end by two or more cables that form a cable set. Movement of one active link pair is controlled by its corresponding cable set and is independent of any other active link pair. Additional links and cable sets may be added to control additional pairs of links. Surgical stapler 100 can include a cable locking mechanism 101. Cable locking mechanism 101, and permutations thereof, is described in more detail, for example, in U.S. patent application Ser. No. 10/928,479.

In various embodiments of the invention, the link sets or link systems are designed to provide torque transmission between the adjacent links while still allowing for pivoting movement between the links. When an actuating force is applied by a cable or cables along one side of the links, adjacent links pivot with respect to one another. The pivoting motion of one or more links causes a bend in the link set. Torque transmission between links is accomplished by operably connecting adjacent links such that rotation of one link around its central axis transfers torque to the next link.

According to various embodiments, adjacent links are configured to have a torque-conferring protrusion that is engaged by a socket of an adjacent link or bushing. The torque-conferring protrusions generally have a non-circular circumference around a cross-section of the protrusion perpendicular to the central axis of the link (referred to herein as the "latitudinal circumference"). Such protrusions are said to have a "non-circular latitudinal circumference." The non-circular latitudinal circumference allows one adjacent link to be rotated around its central axis and confer torque from the torque-conferring protrusion to the socket, and in turn to the adjacent link. The transfer of torque causes corresponding rotation of the second adjacent link around its central axis while still allowing for pivoting movement between the links.

Torque-conferring protrusions can have a circular circumference around a cross-section of the protrusion that intersects or is aligned with the central axis of the link (referred to herein as the "longitudinal circumference"). Such protrusions are said to have a "circular longitudinal circumference." The circular longitudinal circumference allows one adjacent link to be pivoted within an engaged socket of a bushing or adjacent link. The pivoting motion causes a corresponding bend in the link system while still allowing for torque transfer between the links. More generally, a torque-conferring protrusion can have a curved longitudinal circumference. The term "curved longitudinal circumference" includes a circular longitudinal circumference, as well" as other curved longitudinal surfaces.

In addition, according to various embodiments, adjacent links are configured to have a ball section that, along with the torque-conferring protrusion, is also engaged by a socket of an adjacent link or bushing. The ball section can be configured to have a circular latitudinal circumference and a circular longitudinal circumference. The circular longitudinal circumference and circular latitudinal circumference allows the link to pivot freely within the socket of the adjacent bushing or link. More generally, a ball section can have a curved longitudinal circumference and/or a curved latitudinal circumference. The term "curved latitudinal circumference" includes a circular latitudinal circumference, as well as other curved latitudinal surfaces.

FIGS. 2A-2D show a representative embodiment of such a link system in greater detail. Adjacent links 122 and 124 are separated by bushing 126. With respect to FIG. 2A, the link system is in an unbent conformation in which central axes X1, X$_2$, and X3 of link 122, link 124, and bushing 126, respectively, overlap. Link 122 includes torque-conferring protrusion 128 and ball section 130. Likewise, link 124 includes torque-conferring protrusion 132 and ball section 134. Bushing 126 engages torque-conferring protrusion 128 of link 122 in socket 136 and engages torque-conferring protrusion 132 of link 124 in socket 138. Ball section 130 engages ball-shaped recess 166 of bushing 126, while ball section 134 engages ball-shaped recess 168. Engagement of ball sections 130 and 134 and ball-shaped recesses 166 and 168, respectively, allows thrust loads to be directed from link 122 to link 124, and vice versa.

Links 122, 124 further include cable channels 140, 142 that allow the passage or anchoring of cable sets (not shown). Cable channels 140, 142 are offset from the axes X1 and X2 of links 122, 124 such that when a tension force is applied to one or more cables, torque-conferring protrusions 128, 132 of links 122, 124 pivot within sockets 136, 138 of bushing 126, and ball sections 130, 134 pivot within ball-shaped recesses 166, 168, causing link system 104 as a whole to bend. Each link 122, 124 also includes a central channel 144, 146, respectively, that is aligned with the central axis of its link. When assembled, these channels form a central lumen through which actuating cables (not shown) are passed for controlling and/or actuating the stapler (FIG. 1, 107). The central channel generally also provides passage for additional cables, wires, fiber optics, or other like elements associated with any desired tool or instrument used in conjunction with the link system or articulating mechanism of the invention. This allows the links and bushings to pivot relative to one another without impinging the passage of an actuating cable in central channels 144, 146 for tools at the end of link system 200. While the provision of a central channel is advantageous for the above reasons, it will be appreciated that links and bushings can also be provided without such channels, and that control of a tool or instrument associated with the link system or articulating mechanism of the invention can also be accomplished by routing actuating cables and other like elements along the periphery of the link system or articulating mechanism.

Figure 2B:
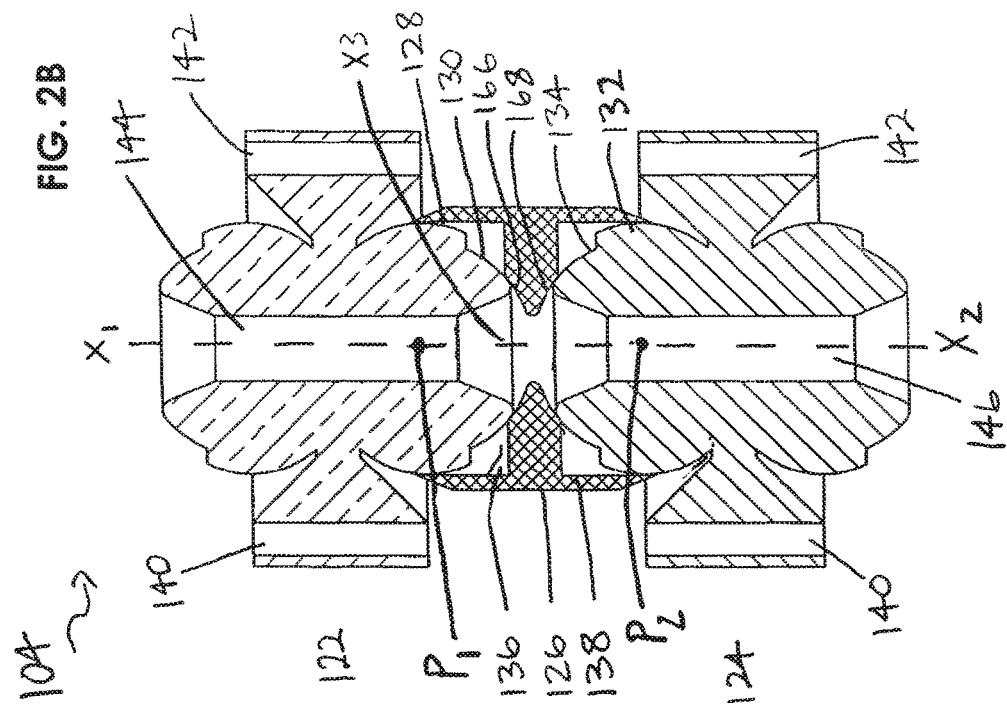
FIG. 2B shows a cross-sectional view of the link system of FIG. 2A, taken along the plane designated by line L-L.
Figure 2A:
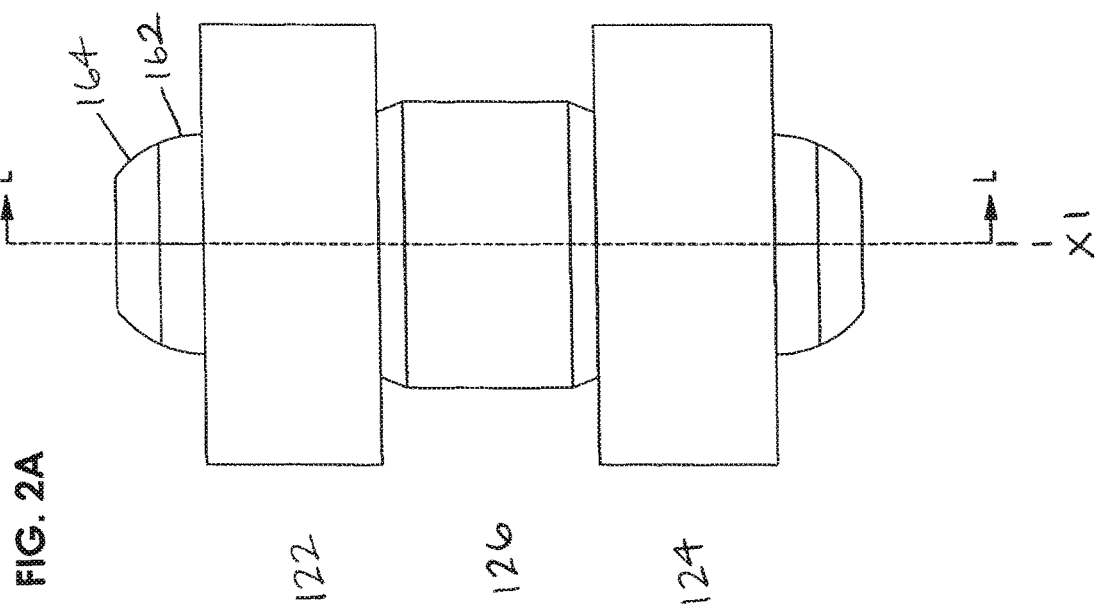
FIG. 2A shows a side view of a link system similar to the distal link system of the embodiment depicted in FIG. 1A.
Figure 2E:
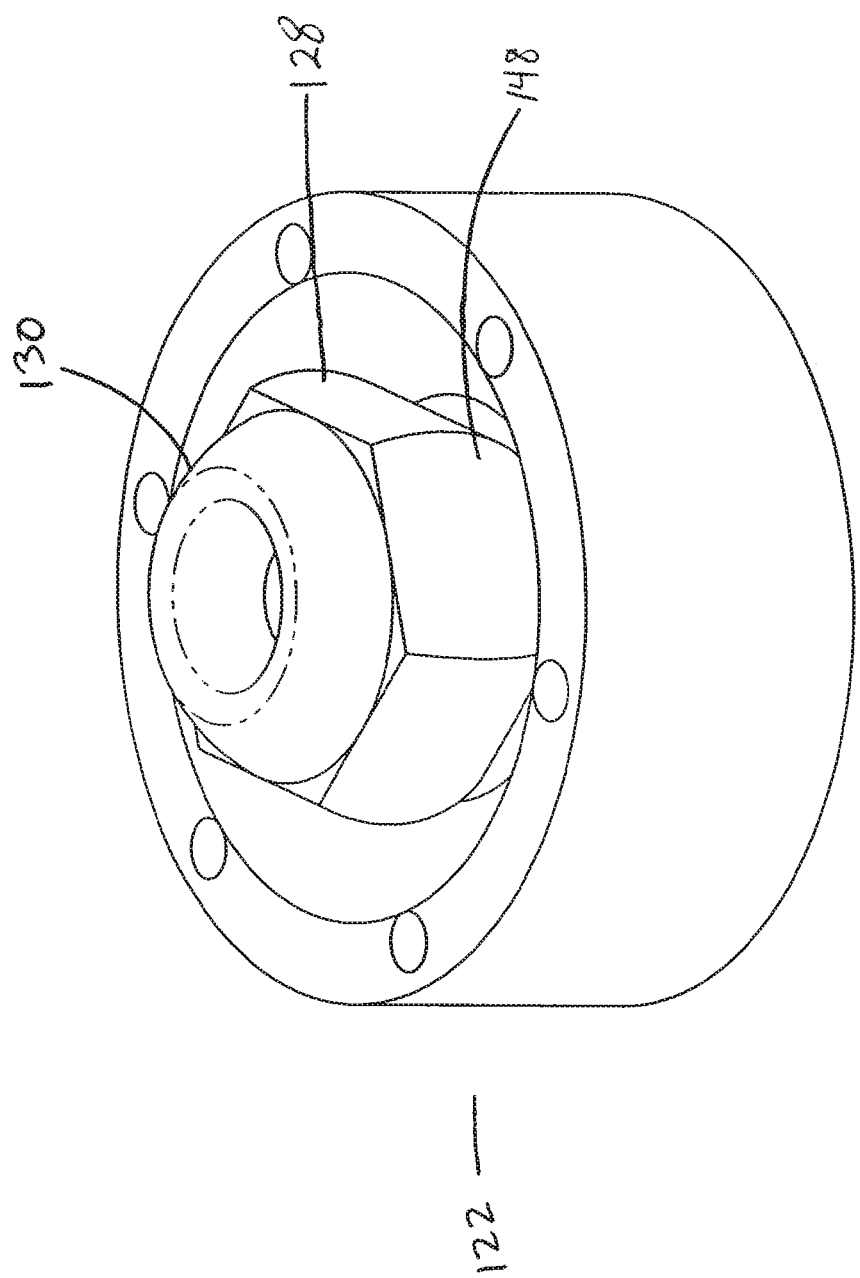
FIG. 2E shows a perspective view of a single link of the link system of FIG. 2A.
Figure 5C:
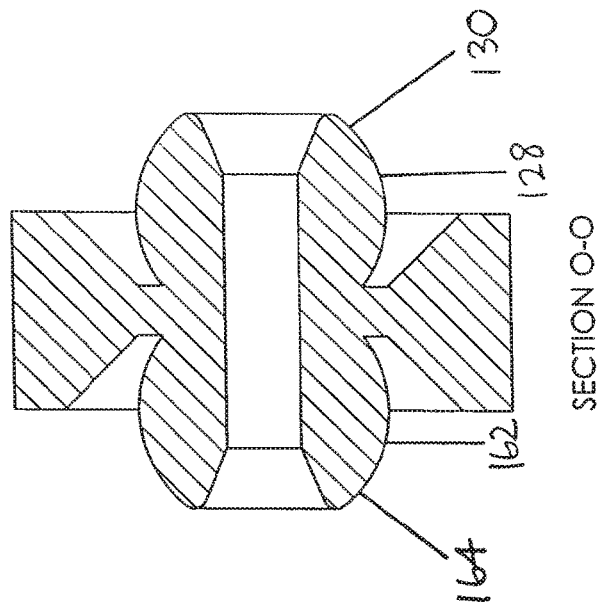
FIG. 5C shows a cross-sectional view of the link depicted in FIG. 5A taken along the plane designated by line) O-O.
Figure 5A:
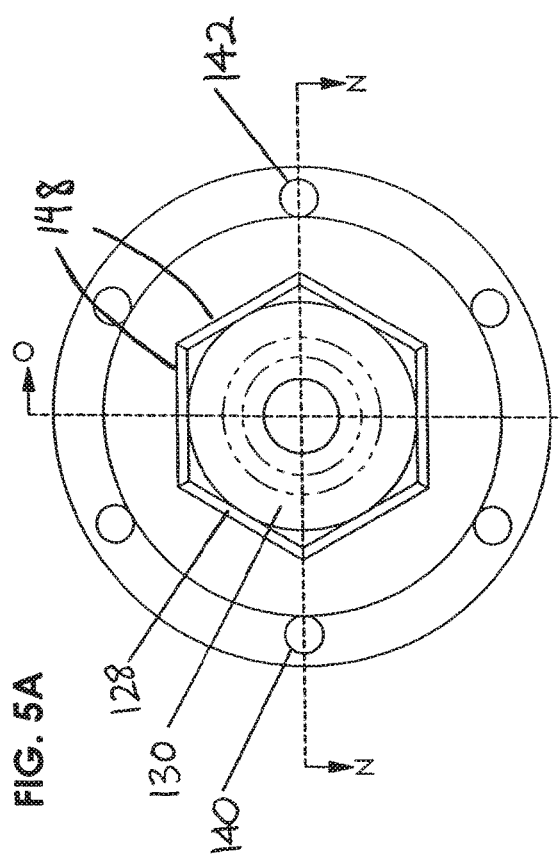
FIG. 5A shows an end view of a single link of the link system of FIG. 2A.
Figure 5B:
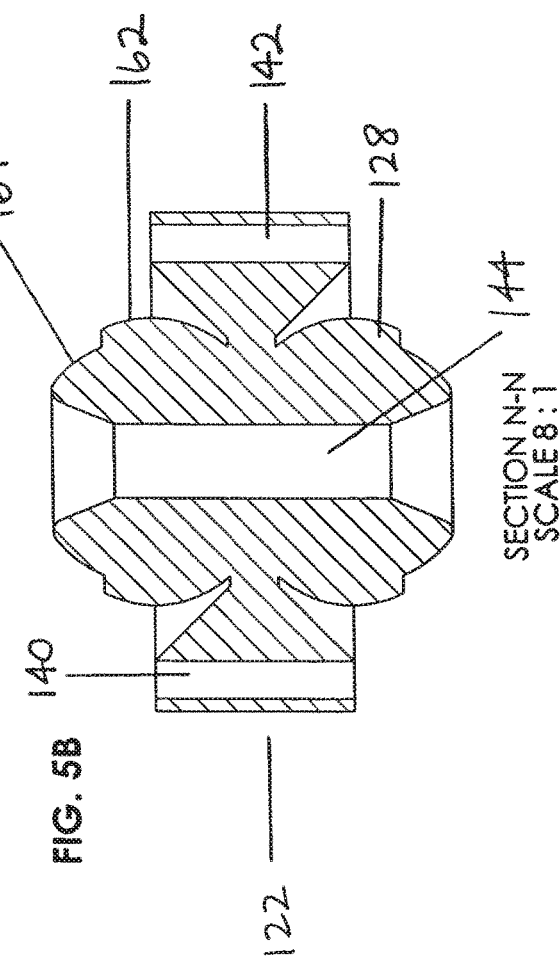
FIG. 5B shows a cross-sectional view of the link depicted in FIG. 5A taken along the plane designated by line N-N.
Figure 7D:
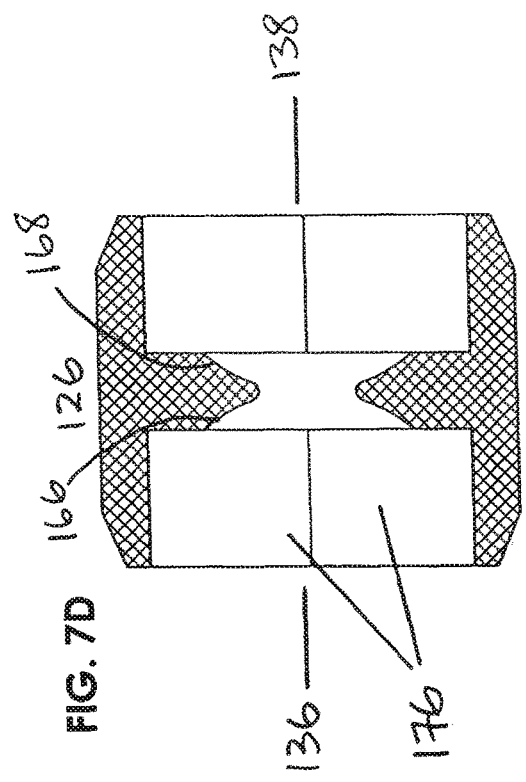
FIG. 7D shows a cross-sectional view of the bushing depicted in FIG. 7B taken along the plane designated by line U-U.
Figure 7A:
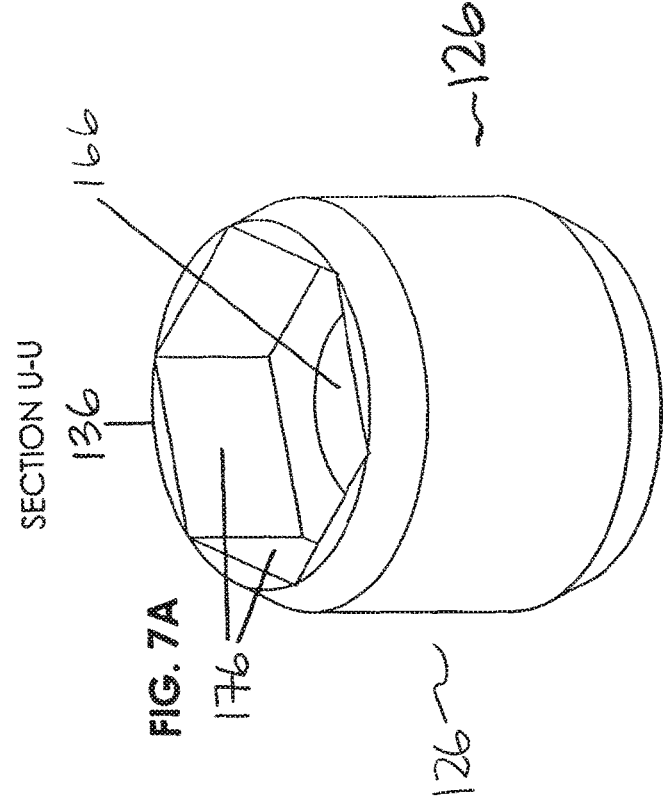
FIG. 7A shows a perspective view of a single bushing of the link system depicted in FIG. 2A.
Figure 7B:
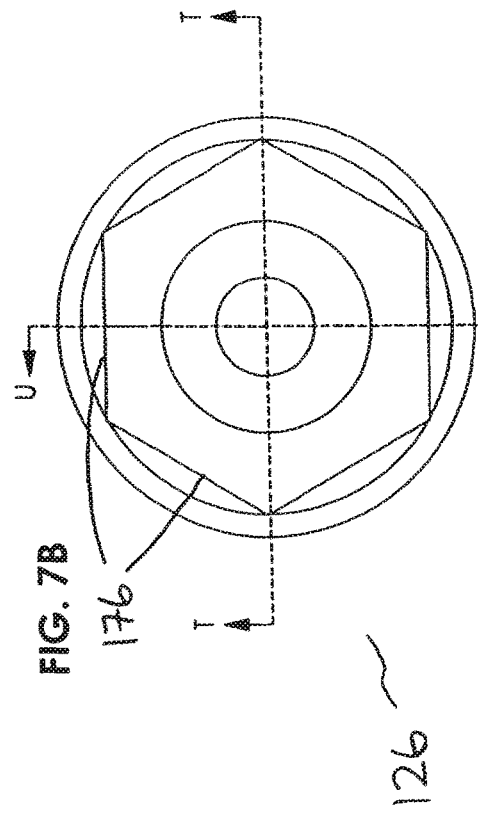
FIG. 7B shows an end view of the bushing depicted in FIG. 7A.
Figure 7C:
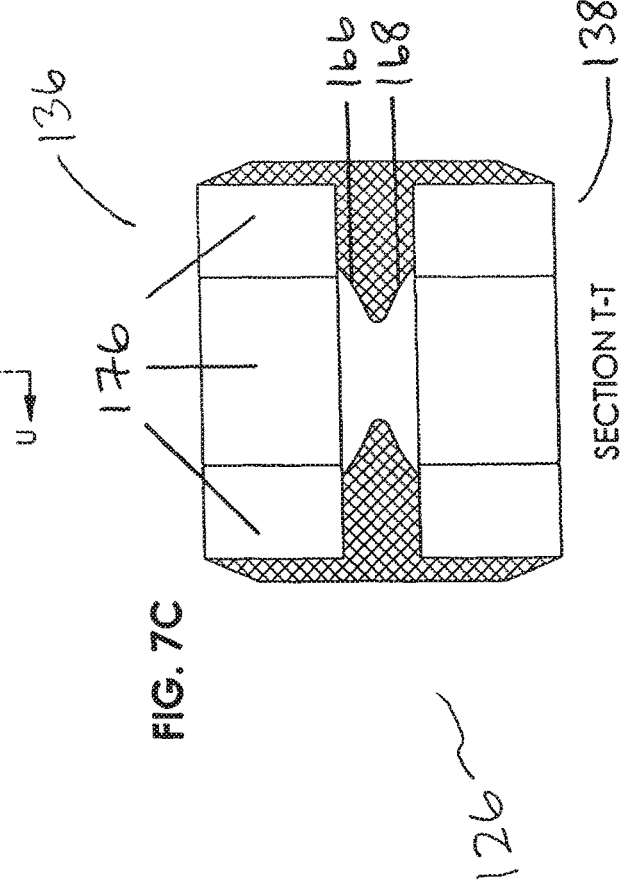
FIG. 7C shows a cross-sectional view of the bushing depicted in FIG. 7B taken along the plane designated by line T-T.

The torque-conferring and pivoting capability of the link set shown in FIGS. 2A-2D is illustrated more clearly with reference to individual links and bushings. FIG. 2E and FIGS. 5A-C depict link 122 of the link-bushing-link embodiment. FIGS. 7A-D depict bushing 126 of the link-bushing-link embodiment:

With reference to FIG. 2E, link 122 has a torque-conferring protrusion 128 with six tangentially distributed faces 148, giving torque-conferring protrusion 128 a hexagonal latitudinal circumference. Torque-conferring protrusion 128 is circular along the longitudinal circumference. Link 122 further includes ball section 130. The ball section 130 is circular along the longitudinal circumference and the latitudinal circumference. With reference to FIGS. 5A-C, hexagonal torque-conferring protrusion 128 and ball section 130 are mirrored on the opposite end of link 122 at torque-conferring protrusion 162 and ball section 164. Torque-conferring protrusion 162 is circular along the longitudinal circumference. Like ball section 130, ball section 164 has a circular latitudinal circumference and a circular longitudinal circumference. Decoupling the torque-conferring protrusion 128 from the ball section 130 allows separate sections to transfer separate components of force in different directions. Torque-conferring section 128 transmits torque but cannot transfer axial loads in the direction of axis X$_1$ Conversely, ball section 130 transfers axial loads in the direction of axis X$_1$, but does not transfer torque around axis X$_1$. The torque-conferring capability of torque-conferring protrusion 128 is decoupled from the axial load conferring capability of ball section 130. Because the torque-conferring function and axial load conferring function are separated to different portions of link 122, the link transfers torque around axis X$_1$ and transfers axial loads along axis X$_1$ with greater precision.

Each torque-conferring protrusion and ball section is configured to engage a socket of a bushing. One such bushing of the present embodiment is illustrated more clearly in FIGS. 7A-D. Bushing 126 has two sockets 136, 138, each terminating in a ball-shaped recess 166, 168, respectively. Each socket 136, 138 includes six recessed faces 176 to form a hexagonal structure. Each hexagonal socket 136, 138 is configured to engage hexagonal torque-conferring protrusions 128 and 162. Ball-shaped recesses 166 and 168 are configured to receive ball sections 130 and 164, respectively.

FIGS. 2C and 2D show the link system of FIGS. 2A and 2B, respectively, rotated by 90°. With reference to FIG. 2B, the view depicts an abrupt change from torque-conferring protrusions 128, 132 to ball sections 130, 134, respectively. In the perspective provided by FIG. 2D, however, the transition between torque-conferring protrusions 128, 132 to ball sections 130, 134, respectively, is smooth. From this perspective, link 122 lacks a vertex between protrusions 128, 132 to ball sections 130, 134, respectively.

The torque-conferring protrusion and bushing provide for torque transmission between the links. Each face 148 (FIG. 5A) on torque-conferring protrusion 128 abuts a face 176 (FIGS. 7 A-D) in socket 136, so as to restrict relative rotational motion between link 122 and bushing 126. When link 122 is rotated, each face 148 of protrusion 128 engages its corresponding face 176 of socket 136, transferring rotational force, i.e., torque, to the socket. With further reference to FIGS. 2A-D, this torque transfers through torque-conferring protrusion 128 of link 122 to engaged socket 136 of bushing 126 and causes corresponding rotation of bushing 126 around axis X3. Likewise, each face of torque-conferring protrusion 132 of link 124 abuts a face in socket 138 of bushing 126. When bushing 126 rotates around axis $X_3$, each face of socket 138 engages its corresponding face of torque-conferring protrusion 132. Rotational force (i.e., torque) is transferred from socket 138 of bushing 126 to torque-conferring protrusion 132 of link 124, resulting in corresponding rotational movement of link 124. Thus, rotation of link 122 around axis $X_1$ causes corresponding rotation of bushing 126 around axis $X_3$, which in turn causes rotation of link 126 around axis $X_2$.

While the link system of this embodiment provides torque transfer as described, at the same time it freely allows for pivoting motion between links 122, 124. Specifically, links 122 and 124 can pivot relative to one other to cause a bend in the link set. Pivoting motion is more clearly illustrated with reference to FIGS. 4A-D. Each torque-conferring protrusion 128, 132 is circular along its longitudinal circumference. Likewise, each ball section 130, 134 is circular along its longitudinal circumference and latitudinal circumference. The circular longitudinal circumference of each ball section 130, 134 allows each ball section 130, 134 to move within its corresponding ball-shaped recess 166, 168. The circular longitudinal circumference of each ball section 130, 134 creates pivot points between adjacent links. With respect to FIG. 4B, pivot points P1 and P2 are located along the central axis of each link 122, 124. More specifically, $P_1$ and P2 are located at the centers of the circular longitudinal circumference of ball sections 130 and 134, respectively. The circular longitudinal circumference of torque-conferring protrusion 128, 132 allows each link 122, 124 to pivot within bushing 126 about points $P_1$ and $P_2$, respectively. That is, the torque-conferring protrusions do not engage or interfere with the bushing when subjected to pivoting movement, such that the links can freely pivot about ball sections 130 and 134. The pivoting motion of each link 122, 124 with respect to bushing 126 results in a bend in the link system. The link system allows pivoting motion between links 122 and 124, while providing for torque transmission between the links.

Figure 4D:
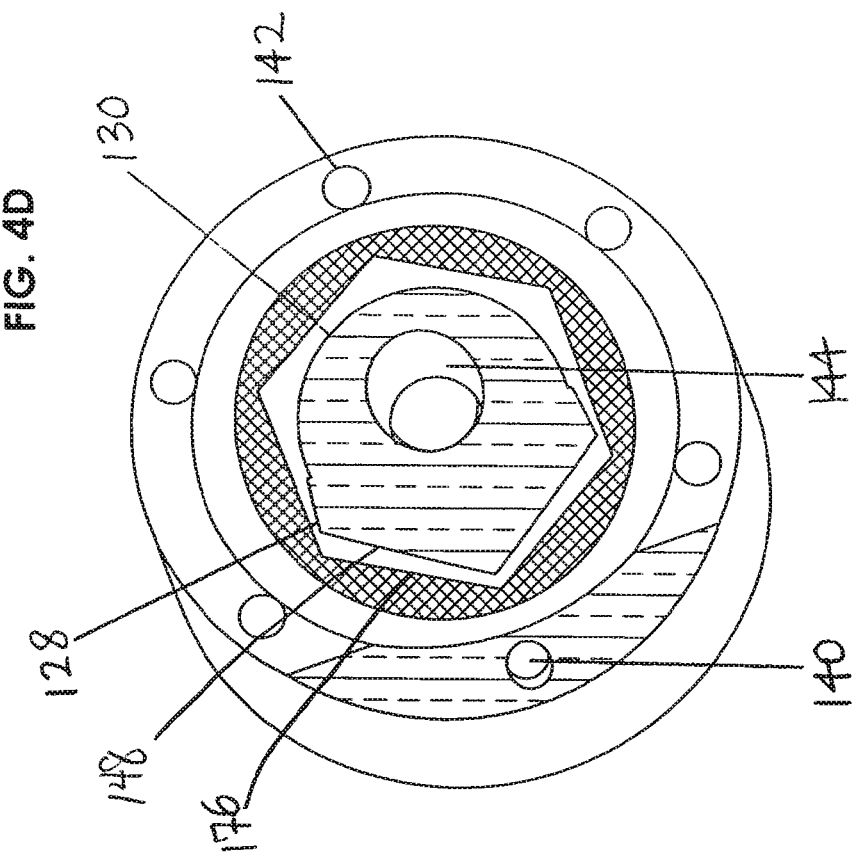
FIG. 4D shows a cross-sectional view of the device depicted in FIG. 4B taken along the plane designated by line AE-AE.
Figure 4C:
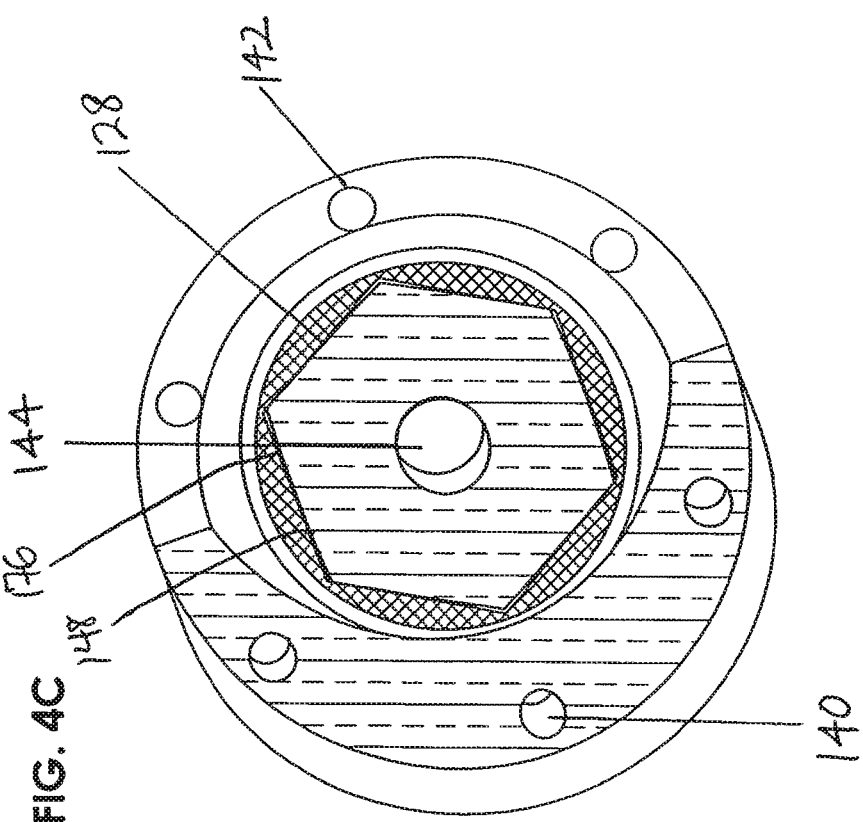
FIG. 4C shows a cross-sectional view of the device depicted in FIG. 4B taken along the plane designated by line AD-AD.

The pivoting link system retains the ability to transfer torque when the link system is in the bent conformation. With further reference to FIGS. 4C and 4D, links 122 and 124 are pivoted within respective sockets 136, 138 of bushing 126, resulting in a bend in the link system. In this bent conformation, protrusion 128 remains engaged by hexagonal socket 136. Rotation of link 122 around axis $X_1$ transfers torque from link 122 to bushing 126. Similarly, hexagonal torque-conferring protrusion 134 remains engaged by hexagonal socket 138. Rotation of bushing 126 around axis $X_3$ transfers torque from bushing 126 to link 124, and link 124 rotates around axis X2. Rotation of link 122 around axis $X_1$ causes corresponding rotation of link 124 around axis $X_2$. Torque is transferred between links in the bent link system, while still allowing for pivoting motion between the links.

In the present embodiment, the degree of pivoting motion is limited by the torque-conferring protrusion more clearly illustrated in FIG. 4B. As described above, torque-conferring protrusions 128, 132 and ball sections 130, 134 pivot in bushing 126 with respect to points $P_1$ and $P_2$ when engaged by sockets 136, 138 of a bushing 126. Each torque-conferring protrusion pivots as far as respective ball-shaped recesses 166, 168 of each socket 136, 138. Vertex 170 between adjoining faces of torque-conferring protrusion 128 is prevented from extending into the ball-shaped recess 166 of socket 136. Similarly, vertex 172 between faces of torque-conferring protrusion 132 is prevented from extending into the ball-shaped recess 168 of socket 138.

In other embodiments, other features can limit the ability of a torque-conferring protrusion to extend into a ball-shaped region and restrain pivoting motion. For example, bushing rim 180 of bushing 126 can come into contact with conical depression 182 of link 122. When bushing rim 180 contacts conical depression 182, link 122 cannot pivot further about pivot point $P_1$.

With certain embodiments of link systems described herein include a link-bushing-link conformation, other embodiments of link systems without bushings are also capable of transmitting torque while still allowing for pivoting movement between the links. FIGS. 14A-C show another embodiment of a representative link system. Link system 700 includes adjacent links 722 and 724. Link 724 includes torque-conferring protrusion 732 and ball section 734. Socket 726 of link 722 engages torque-conferring protrusion 732 of link 724. Links 722, 724 further include cable channels 740, 742 that allow the passage or anchoring of cable sets (not shown). Cable channels 740, 742 are offset from the axes $X_{13}$ and $X_{14}$ of links 722, 724 such that when a tension force is applied to one or more cables, torque-conferring protrusion 732 and ball section 734 of link 724 can pivot within socket 726 of link 722, pivoting links 722, 724 with. respect to each other about pivot point $P_6$ and causing link system 700 as a whole to bend. Link system 700 does not include a bushing disposed between links 722 and 724.

Each link 722, 724 also has a central channel 744, 746. When link system 700 is assembled, these channels form a central lumen through which actuating cables (not shown) are passed. When assembled, these channels form a central lumen through which actuating cables (not shown) are passed for controlling and/or actuating the stapler (FIG. 1, 107). The central channel generally also provides passage for additional cables, wires, fiber optics, or other like elements associated with any desired tool or instrument used in conjunction with the link system or articulating mechanism of the invention. This allows the links and bushings to pivot relative to one another without impinging the passage of an actuating cable. While the provision of a central channel is advantageous for the above reasons, it will be appreciated that links and bushings can also be provided without such channels, and that control of a tool or instrument associated with the link system or articulating mechanism of the invention can also be accomplished by routing actuating cables and other like elements along the periphery of the link system or articulating mechanism.

The torque-conferring protrusion and bushing provide for torque transmission between the links. With reference to FIG. 14C, each face of torque-conferring protrusion 732 abuts a face in socket 726, so as to restrict relative rotational motion between link 722 and link 724. When link 722 is rotated around axis $X_{13}$, torque-conferring protrusion 732 transfers rotational force, i.e., torque, to socket 726, causing corresponding rotation of link 724 around axis $X_{14}$.

While the link system of this embodiment provides torque transfer as described, at the same time it freely allows for pivoting motion between links 722, 724. Specifically, links 722 and 724 can pivot relative to one other to cause a bend in the link set. Torque-conferring protrusion 732 is circular along its longitudinal circumference. Ball section 734 is circular along its longitudinal circumference and latitudinal circumference. The circular longitudinal circumference of ball section 734 allows ball section 734 to move within the corresponding ball-shaped recess 766 of socket 726. The circular longitudinal circumference of torque-conferring protrusion 732 creates pivot point $P_6$ between adjacent links 722, 724. The pivoting motion of links 722 and 724 with respect to one another results in a bend in link system 700. Link system 700 allows pivoting motion between links 722 and 724, while providing for torque transmission between the links.

The ability to provide torque transmission while allowing for pivoting movement between links can be achieved in other link-bushing-link conformations. Another alternative link system is depicted in FIGS. 3A-3D.

Adjacent links 222 and 224 are separated by bushing 226. Link 222 includes torque-conferring protrusion 228 and ball section 230. Likewise, link 224 includes torque-conferring protrusion 232 and ball section 234. Bushing 226 engages torque-conferring protrusion 228 of link 222 in socket 236 and engages torque-conferring protrusion 232 of link 224 in socket 238. Ball sections 230 and 234 rest in the corresponding ball-shaped recess 266, 268. Links 222, 224 further include cable channels 240, 242 that allow the passage or anchoring of cable sets (not shown). Cable channels 240, 242 are offset from the axes $X_4$ and $X_5$ of links 222, 224 such that when a tension force is applied to one or more cables, torque-conferring protrusions 228, 232 and ball sections 230, 234 of links 222, 224 can pivot within sockets 236, 238 of bushing 226, pivoting links 222, 224 with respect to each other and causing the link system as a whole to bend.

Each link 222, 224 also includes a central channel 244, 246, respectively, aligned with the central axis of the link. When assembled, these channels form a central lumen through which actuating cables (not shown) are passed for controlling and/or actuating the stapler (FIG. 1, 107). The central channel generally also provides passage for additional cables, wires, fiber optics, or other like elements associated with any desired tool or instrument used in conjunction with the link system or articulating mechanism of the invention. This allows the links and bushings to pivot relative to one another without impinging the passage of an actuating cable. While the provision of a central channel is advantageous for the above reasons, it will be appreciated that links and bushings can also be provided without such channels, and that control of a tool or instrument associated with the link system or articulating mechanism of the invention can also be accomplished by routing actuating cables and other like elements along the periphery of the link system or articulating mechanism.

The torque-conferring protrusion and bushing provide for torque transmission between the links. With reference to FIGS. 6B and 6C, link 222 has torque-conferring protrusion 228 and a ball section 230, and torque-conferring protrusion 262 and ball section 264. With reference to FIG. 6A, torque-conferring protrusion 228 includes eight radially distributed faces, giving the torque-conferring protrusion 228 an octagonal latitudinal circumference.

With further reference to FIGS. 3A-E, torque transfers through torque-conferring protrusion 228 of link 222 to engaged socket 236 of bushing 226 and causes corresponding rotation of bushing 226 around axis $X_6$. Likewise, each face of torque-conferring protrusion 232 of link 224 abuts a face in socket 238 of bushing 226. When bushing 226 rotates around axis $X_6$, each face of socket 238 engages its corresponding face of torque-conferring protrusion 232. Rotational force (i.e., torque) is transferred from socket 238 of bushing 226 to torque-conferring protrusion 232 of link 224, resulting in corresponding rotational movement of link 224.

Thus, rotation of link 222 around axis causes corresponding rotation of bushing 226 around axis $X_6$, which in turn causes rotation of link 226 around axis $X_5$.

While the link system of this embodiment provides torque transfer as described, at the same time it freely allows for pivoting motion between links 222, 224. Specifically, links 222 and 224 can pivot relative to one other to cause a bend in the link set. Each torque-conferring protrusion 228, 232 is circular along its longitudinal circumference. Likewise, each ball section 230, 234 is circular along its longitudinal circumference and latitudinal circumference. The circular longitudinal circumference of each ball section 230, 234 allows each ball section 230, 234 to move within its corresponding ball-shaped recess 266,268. Ball sections 230•and 234, respectively, creates pivot points between adjacent links. With respect to FIG. 3C, pivot points P3 and $P_4$ are located along the central axis of each link 222, 224, respectively. The circular longitudinal circumference of ball sections 230 and 234 allows links 222 and 224 to pivot within bushing 226 about pivot points $P_3$ and $P_4$. The pivoting motion of each link 222, 224 with respect to bushing 226 results in a bend in the link system. The link system allows pivoting motion between links 222 and 224, while providing for torque transfer between the links.

Figure 8F:
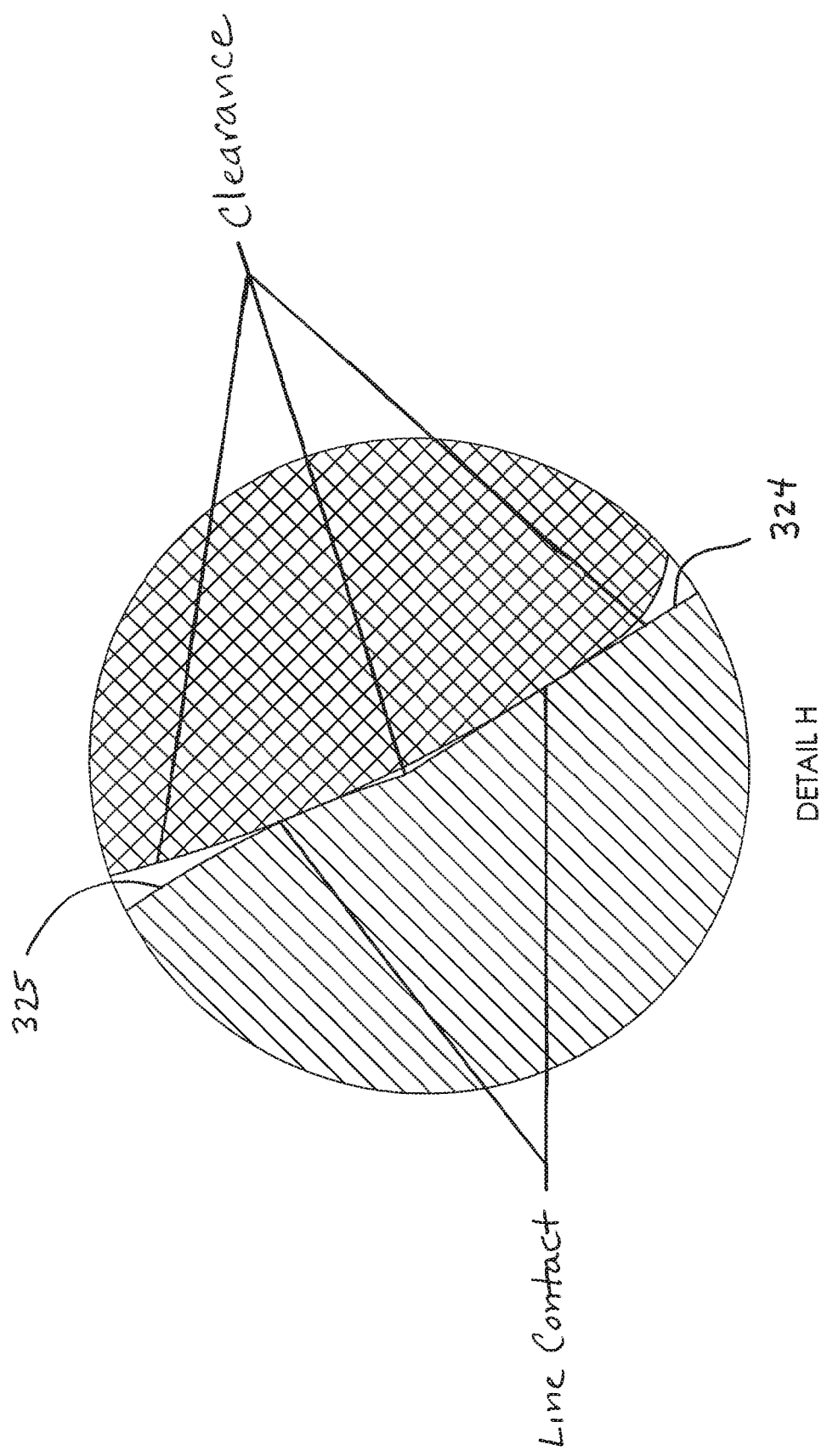
FIG. 8F is an exploded cross-sectional view of the articulating link system of FIG. 8C taken along the plane designated by circle H.

Another embodiment of the link systems is depicted in FIGS. 8A-F. With reference to FIG. 8A, link system 300 includes adjacent links 302 and 304. Axis $X_7$ of link 302 and axis $X_8$ of link 304 are aligned when the links are in the straight, unbent conformation. With reference to FIGS. SC and 8E, link 302 includes torque-conferring protrusion 310. Link 304 includes socket 312. Torque-conferring protrusion 310 of link 302 is engaged by socket 312. Links 302, 304 further include a plurality of cable channels 314 that allow the passage or anchoring of cable sets (not shown). When a tension force is applied to one or more cables, torque-conferring protrusion 310 pivots about point $P_5$ within socket 312 of link 304, pivoting link 302 with respect to link 304 and allowing the link set as a whole to bend. Each link 302 and 304 also includes central channels 316 and 318 that are respectively aligned with axes $X_7$ and $X_8$ of the link system 300.

The torque-conferring and pivoting capability of the link set shown in FIGS. 8A-F is illustrated more clearly with reference to FIGS. 9A-B. With reference to FIG. 9A, torque-conferring protrusion 310 has six radially distributed faces 320, such that the latitudinal circumference of torque-conferring protrusion 310 is hexagonal, and has a curved longitudinal circumference. With reference to FIG. 9B, link 304 includes socket 312. Socket 312 includes six radially distributed faces 324 and six radially distributed faces 325 both configured to engage torque-conferring protrusion 310 of link 302 of FIG. 9A. The latitudinal circumference of faces 324 is hexagonal, and the longitudinal cross section is flat. The latitudinal circumference of faces 325 is hexagonal, and the longitudinal cross section is curved in a convex fashion.

When link 302 engages link 304, rotation of link 302 transfers torque to link 304. With further reference to FIGS. 8A-F, hexagonal torque-conferring protrusion 310 is engaged by hexagonal socket 312 of link 304. Each face 320 on torque-conferring protrusion 310 abuts a face 324 on socket 312 forming a line contact between face 320 and face 324. When link 302 rotates around axis $X_7$; the contact between each face 320 of torque-conferring protrusion 310 and the corresponding faces 324 of hexagonal socket 312 results in torque transfer from link 302 to link 304. Transfer of torque results in a corresponding rotation of link 304 around axis $X_8$. Rotation of link 302 causes corresponding rotation of link 304.

Link system 300 also allows for pivoting motion between links 302 and 304. As depicted in FIGS. 8D and 8E, pivoting of link 302 relative to link 304 causes a bend in link system 300. Torque-conferring protrusion 310 is circular along its longitudinal circumference. This circular longitudinal circumference allows torque-conferring protrusion 310 to pivot about point P5 within socket 312 of link 304. The pivoting motion of links 302 and 304 relative to one another allows link system 300 to bend. Link system 300 allows pivoting motion between the links, while providing for torque-transmission between the links.

The pivoting link system retains the ability to transfer torque when the link system is in the bent conformation. With further reference to FIG. 8E, protrusion 310 pivots within socket 312 of link 304. Moreover, the hexagonal latitudinal circumference of socket 312 continues to engage the hexagonal latitudinal circumference of protrusion 310 even in the bent conformation. Rotation of link 302 around axis $X_7$ transfers torque from link 302 to link 304 in the bent conformation, resulting in corresponding rotation of link 304 around axis $X_8$.

While particular embodiments of links have been described as having a hexagonal or octagonal torque-conferring protrusion, it will be recognized that a torque-conferring protrusion can have any configuration, provided that it has a non-circular latitudinal circumference. By way of example and not limitation, such non-circular latitudinal circumference can have any number of sides to form a triangular, square, rectangular, pentagonal, or heptagonal torque-conferring protrusion. The non-circular latitudinal circumference of the torque-conferring protrusion can also include one or more non-circular curved sections, such as, for example, an ellipse or portion thereof. Further, while particular embodiments of links have been described as having a ball section, it will be recognized that links may be designed without a ball section and still maintain the ability to provide torque transmission while allowing for pivoting movement between links.

Likewise, while particular embodiments of bushings have been described as having hexagonal or octagonal sockets that engage hexagonal or octagonal torque-conferring protrusions of corresponding links, it will be recognized that sockets of a bushing can be configured in any configuration, provided that it engages the corresponding torque-conferring protrusion to transfer torque, while allowing pivoting motion of the link in the bushing. By way of example and not limitation, such bushings may include any number of faces to form, for example, a triangular, square, rectangular, pentagonal, or heptagonal socket. The socket can be configured to receive non-circular circumference of the torque-conferring protrusion such as, for example, an ellipse or portion thereof. Further, while particular embodiments of sockets have been described as having a ball-shaped recess, it will be recognized that links may be designed without a ball-shaped recess and still maintain the ability to provide torque transmission while allowing for pivoting movement between links. For example, the ball section of a protrusion could abut a hole in the bottom of the socket so the contact between the two parts would be line contact, while still allowing the pivoting link system to transmit torque and axial thrust loads.

Though various embodiments have been disclosed, it will be understood that aspects of different embodiments can be interchanged or combined in any combination. For example, in embodiments having two links interposed by a bushing, the torque-conferring protrusion can be disposed on either the link or the bushing. In other variations, a torque-conferring protrusion and a ball section are disposed on one end of a bushing, and a socket is disposed on the other end of the bushing. The variations can include any variation disclosed, for example, in pending and commonly U.S. application Ser. Nos. 10/444,769 and 10/928,479, each of which is incorporated herein by reference in its entirety.

Although the embodiments herein describe torque-conferring protrusions and ball sections having circular longitudinal circumferences, it will be appreciated that the torque-conferring protrusions and ball sections can more generally have curved longitudinal circumferences. Such embodiments still maintain the ability to provide torque transmission while allowing for pivoting movement between links.

In other embodiments of the invention, adjacent links are configured to be connected by a plurality of tabs disposed radially around from each axis of adjacent links. The tabs allow one link to be rotated around its respective axis and confer torque to the tabs of an adjacent link. The tabs also allow the one link to pivot with respect to the second link.

Figure 12:
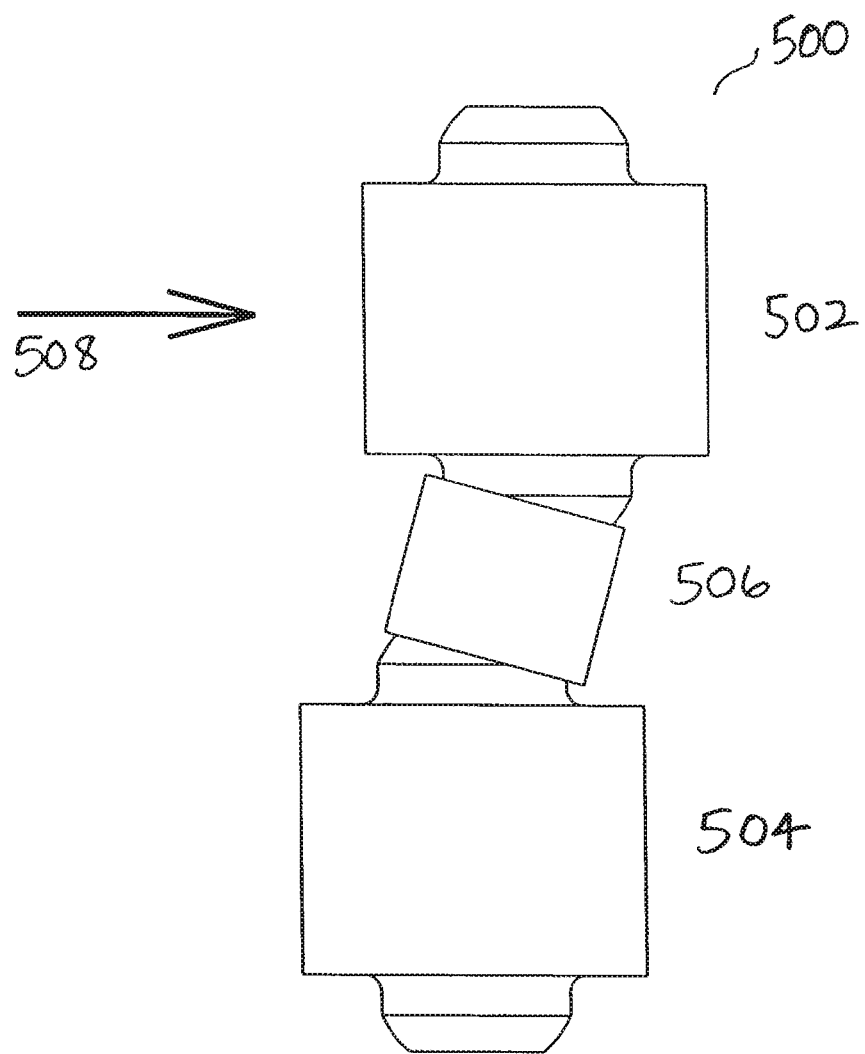
FIG. 12 shows parallelogramming of a link-bushing-link system.

Such link systems also prevent a phenomenon known as "parallelogramming." In a two pivot system such as a link-bushing-link system, "parallelogramming" refers to lateral movement of one link with respect to another link when a side tension or force is applied to the first link. FIG. 12 shows parallelogramming in link-bushing-link system 500. Link system 500 includes link 502 and link 504 separated by bushing 506. When a side load 508 is applied to link 502, link 502 can translate laterally in the direction of the force, instead of pivoting with respect to link 504.

Figure 10B:
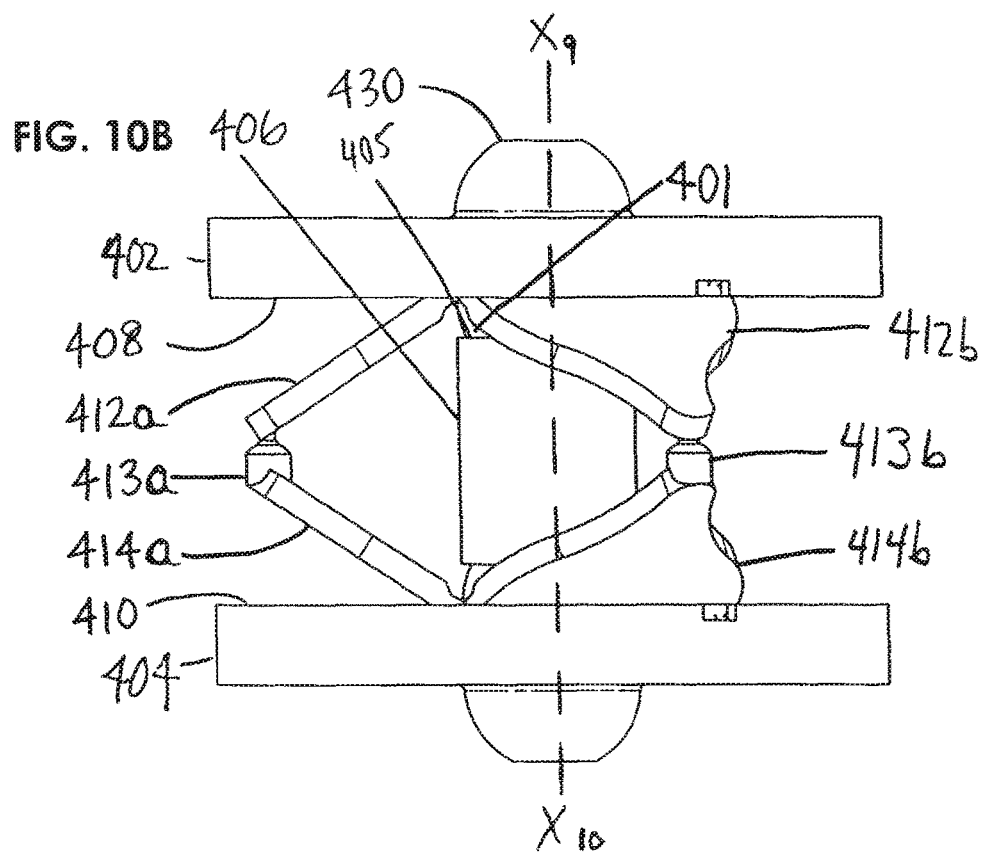
FIG. 10B shows another side view of the link system of FIG. 10A rotated by 90° about axis $X_{10}$ from the view depicted in FIG. 10A.

Link systems having two pivot points between two links, each pivot with one or two degrees of freedom, can be constrained to prevent parallelogramming. One exemplary embodiment of a link system designed to transmit torque while preventing parallelogramming is depicted in FIGS. 10A-F. Link system 400 includes adjacent links 402 and 404 separated by bushing 406. With reference to FIG. 10A, in the straight conformation central axis $X_9$ of link 402 is aligned with central axis $X_{10}$ of link 404. Convex protrusion 401 of adjacent link 402 is engaged by concave depression 405 of bushing 406. Similarly, convex protrusion 403 of adjacent link 404 is engaged by concave depression 407 of bushing 406. Convex protrusion 401 can pivot within concave depression 405, and/or convex protrusion 403 can pivot within concave depression 407.

Figure 10E:
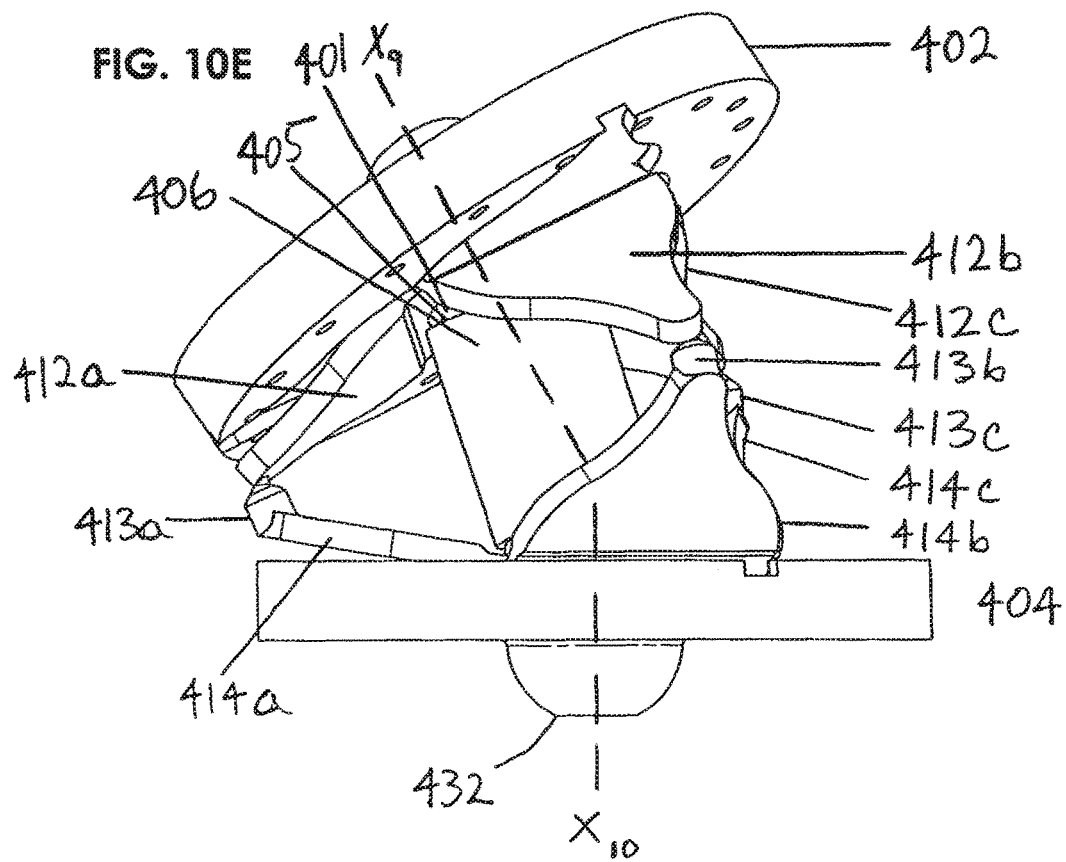
FIG. 10E shows another side view of the bent link system of FIG. 10D.
Figure 10C:
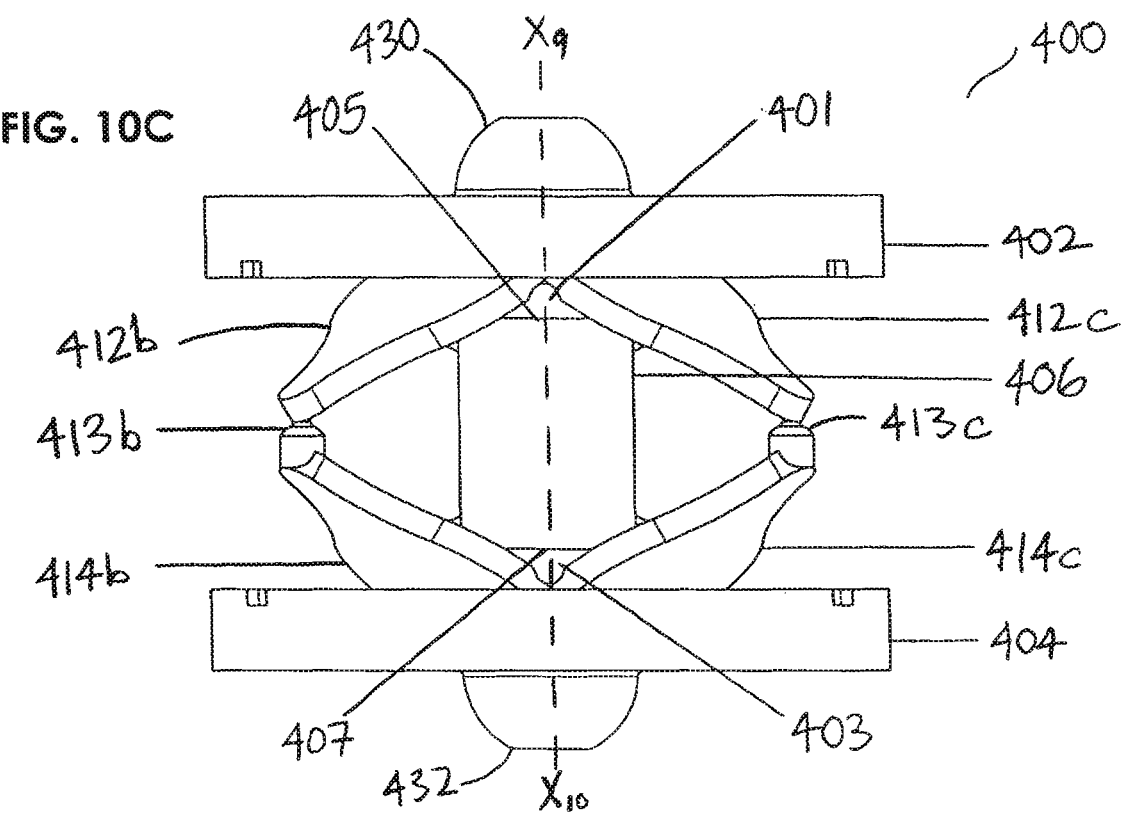
FIG. 10C shows yet another side view of the link system of FIG. 10A rotated by 180° about axes $X_{10}$ from the view depicted in FIG. 10A.
Figure 10F:
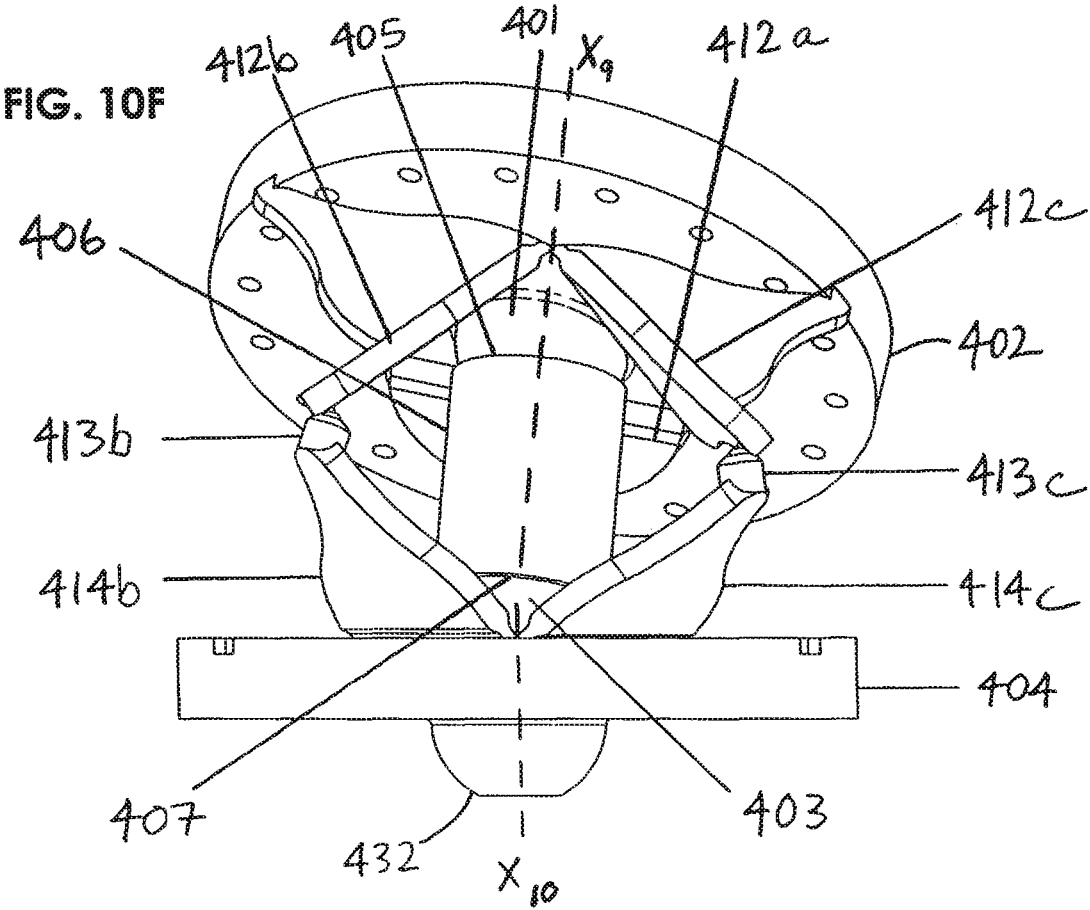
FIG. 10F shows yet another side view of the bent link system of FIG. 10D.

Cable channels 424, 426 are offset from the axes $X_9$ and $X_{10}$ of links 402, 404, respectively, such that when a tension force is applied to one or more cables, concave protrusions 401, 403 can rotate within their respective concave depressions 405, 407, pivoting each link and causing the link set as a whole to bend, as shown more clearly in FIGS. 10D-F. Link 402 includes a first set of three triangular tabs 412 integrally formed with the link. Link 404 includes a second set of three triangular tabs 414 integrally formed with the link. Each set of tabs 412 and 414 is disposed radially from central axes $X_9$ and $X_{10}$, respectively. The tabs are connected to the links by a one degree of freedom joint. Each tab (412a, 412b, and 412c) of the first set of tabs 412 is operably connected to a corresponding tab (414a, 414b, and 414c) of the second set of tabs 414 by ball-and-socket joints (413a, 413b, and 413c). It will be appreciated that the tabs need not be integrally formed with the links, but can be connected to the links by other known methods. Also, it is preferable but not necessary that the tabs dispose radially from the central axes, as tabs disposed non-radially can also be employed.

Figure 11B:
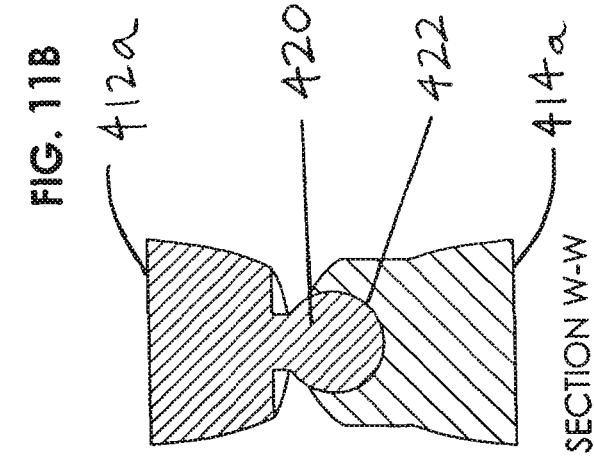
FIG. 11B shows a cross-sectional view of the ball-socket joint depicted in FIG. 11A.
Figure 11A:
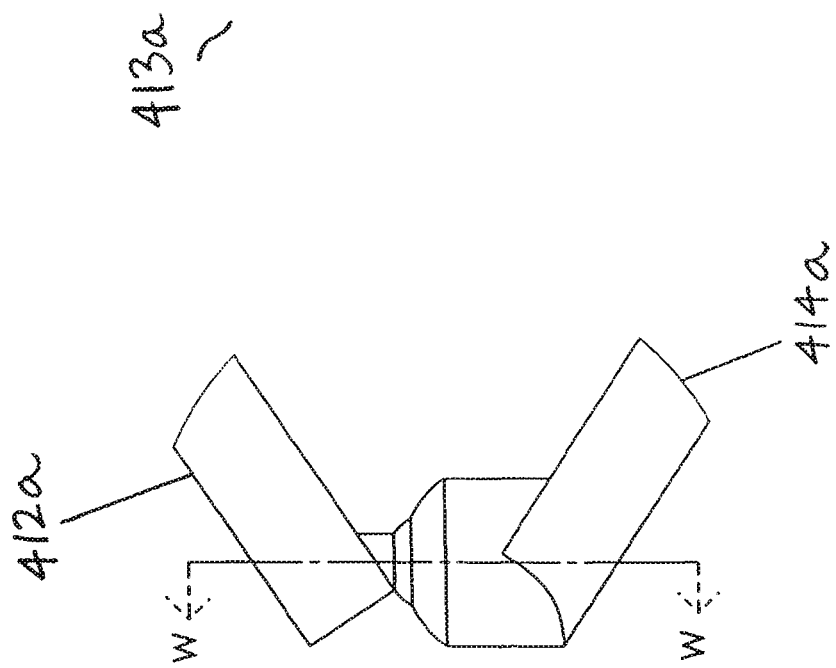
FIG. 11A shows a side view of a ball and socket joint between connected tabs of adjacent links depicted in FIG. 10A.

FIGS. 11A and 11B depicts ball-and-socket joint 413A. Tab 414a terminates in socket 422. Tab 412a terminates at ball 420. Ball 420 is configured to rotate within socket 422. As will be apparent to those of skill in the art, any number of other attachment mechanisms can be used as alternatives to ball-and-socket joint 413a. The only requirement is that the joint is a two degree of freedom joint.

With further reference to FIG. 10A, link system 400 is designed to prevent parallelogramming. When a side load 440 is applied to link 402, the side load is transferred to the two degree of freedom ball-and-socket joints (413a, 413b, and 413c) between each tab (412a, 412b, and 412c) and corresponding tab (414a, 414b, and 414c) by the one degree of freedom joint between each link 402,404 and the corresponding tabs (412a, 412b, and 412c) and (414a, 414b, and 414c), respectively. At least one one-degree of freedom joint is not normal to the side load. In this manner, the first set of tabs 412 operably connected to the second set of tabs 414 prevents translation of link 402 laterally with respect to link 404. Moreover, when link 402 is rotated around axis X9, torque generated by the rotation is transferred through each tab (412a, 412b, and 412c) of the first set of tabs 412 to its corresponding tab (414a, 414b, and 414c) of the second set of tabs 414. Torque is transferred from link 402 to link 404.

Each link 402, 404 also includes central channel 430, 432, respectively, aligned with the axis of its respective link 402, 404. Central channels 430, 432 form a central lumen through which one or more actuating cables may be passed. The cables can be used to control and/or actuate a stapler (FIG. 1, 107). The central channel generally also provides passage for additional cables, wires, fiber optics, or other like elements associated with any desired tool or instrument used in conjunction with the link system or articulating mechanism of the invention. Alternatively, a central channel is not included. Additional cables, wires, fiber optics or other like elements associated with any desired tool or instrument used in conjunction with the link system can be provided off the axis of the link system.

The tabs can be disposed on any link system disclosed herein. In addition, tabs can be disposed on any link system disclosed in U.S. patent application Ser. Nos. 10/444,769, 10/948,911, and 10/928,479. While particular embodiments of link systems have been described as having certain number of tabs, it will be recognized that the link systems require a plurality of tabs. Typically, there are at least as many tabs as the degrees of freedom in the pivot points between the links, i.e., for a one degree of freedom pivoting, at least one tab is used, and for two degrees of freedom, at least two tabs are used. By way of example and not limitation, the link system can include two, three, four, five, six, or more tabs. While particular embodiments have been described as having triangular tabs, the tabs can be any shape. By way of example and not limitation, the tabs can be triangular, rectangular, pentagonal, hexagonal, curved, or partially curved. It will also be recognized that other embodiments of the link systems do not require a bushing. Tabs may be connected in any fashion known in the art, including a ball-and-socket joint, hinged joints, glue, or wire. Alternatively, tabs may be disposed on a flex hinge. Exemplary flex hinges are described, for example, in U.S. patent application Ser. No. 10/928,479.

Figure 13A:
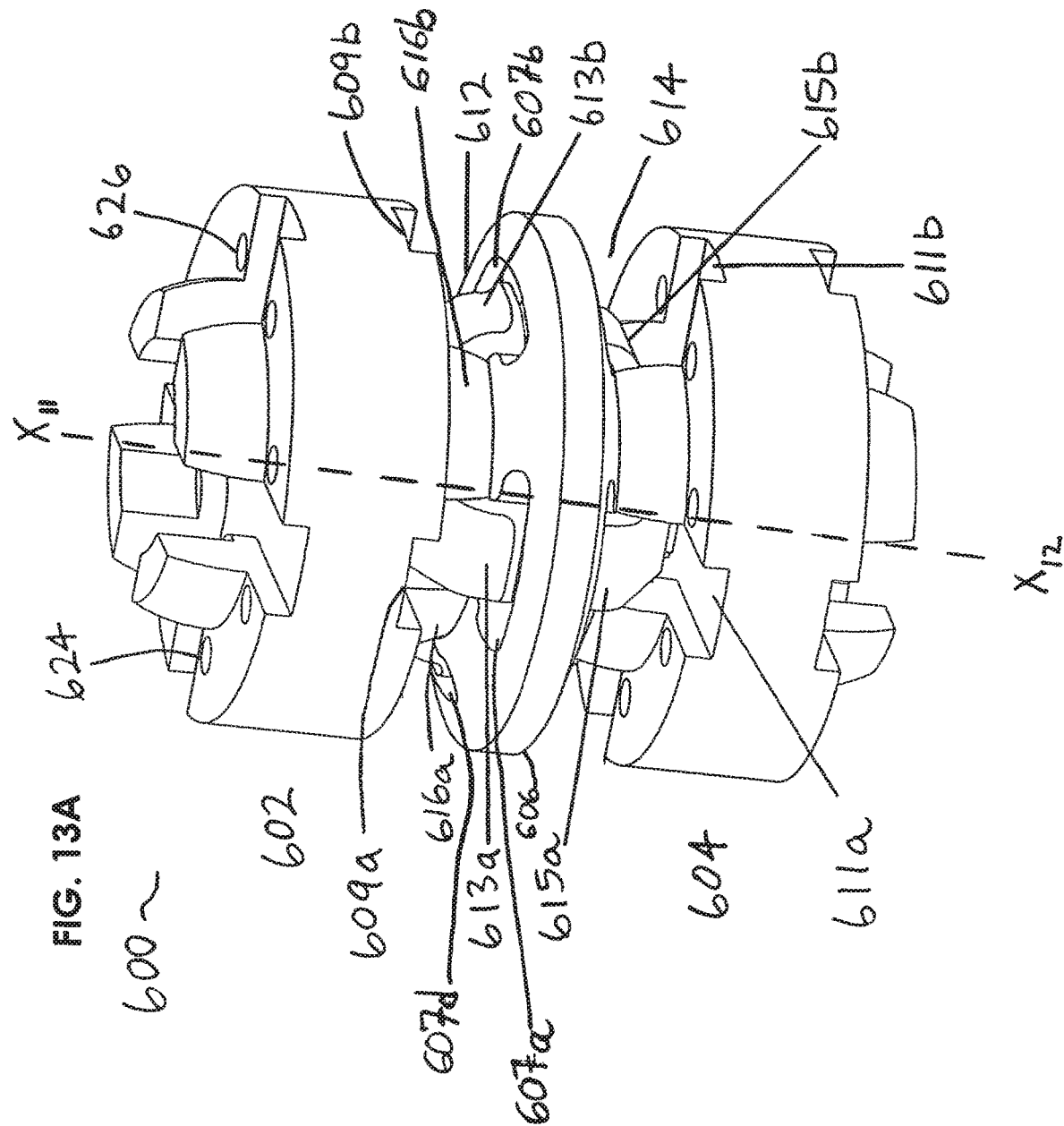
FIG. 13A shows a perspective view of a link system, according to another embodiment of the invention.
Figure 13B:
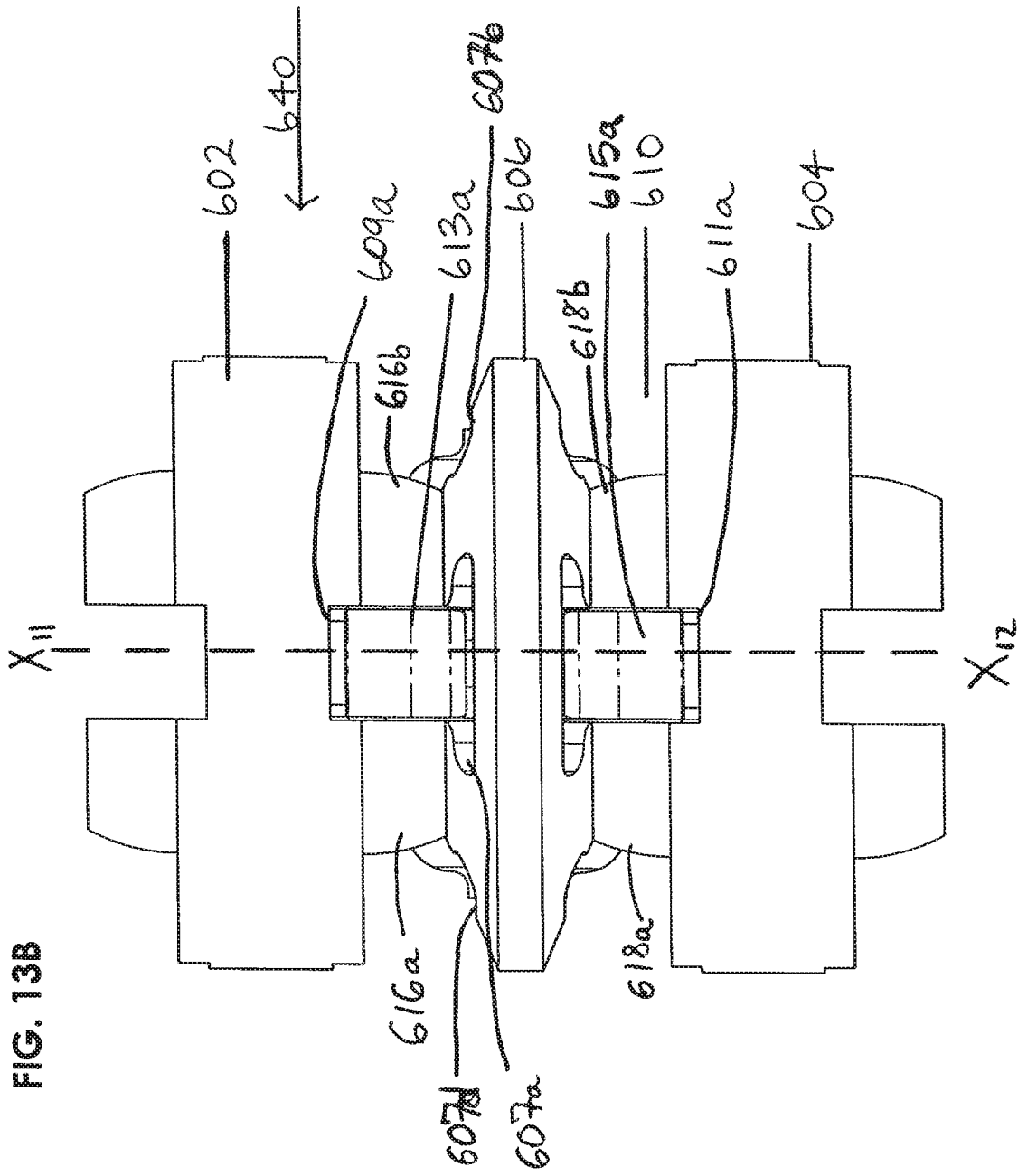
FIG. 13B shows a side view of the link system of FIG. 13A.

Another link system embodiment is shown in FIGS. 13A and 13B that likewise transmits torque and prevents parallelogramming. Link system 600 includes adjacent links 602 and 604 separated by bushing 606. When link system 600 is in the straight conformation, central axis $X_{11}$ of link 602 and central axis $X_{12}$ of link 604 overlap. Link 602 can pivot with respect to link 604, resulting in a bend in link system 600. Cable channels 624, 626 are offset from the axes $X_{11}$ and $X_{12}$ of link system 600 such that when a tension force is applied to one or more cables, link 602 pivots with respect to link 604, causing the link set as a whole to bend. Bushing 606 is disposed between links 602 and 604. Link 602 has four depressions (609a, 609b, 609c, 609d) and four ball portions (616a, 616b, 616c, 616d). Link 602 is engaged by a first set of tabs 612. First set of tabs 612 includes four radially dispersed tabs (613a, 613b, 613c, 613d). Each tab engages one radially dispersed depression (609a, 609b, 609c, 609d) between two radially dispersed ball portions (616a, 616b, 616c, 616d) of link 602. Likewise, link 604 has four radially dispersed depressions (611a, 611b, 611c, 611d) and four radially dispersed ball portions (618a, 618b, 618c, 618d). Link 604 is engaged by a second set of tabs 614. Second set of tabs 614 includes four radially dispersed tabs (615a, 615b, 615c, 615d). Each tab engages one radially dispersed depression (611a, 611b, 611c, 611d) between two and four dispersed ball portions (616a, 616b, 616c, 616d) of link 604.

The first and second sets of tabs 612, 614 are more clearly illustrated in FIGS. 13C and 13D. With respect to FIG. 13C, first set of tabs 612 includes four radially dispersed tabs (613a, 613b, 613c, 613d). Each individual tab in the first set is connected to a base 621 by a one degree of freedom joint, i.e., flex hinge (62 a, 620b, 620c, 620d). Base 621 has a central channel to allow passage of actuating cables and the like. Likewise, second set of tabs 614 includes four radially dispersed tabs (615a, 615b, 615c, 615d). Each individual tab is connected. to the base 623 via a one degree of freedom joint, i.e., flex hinge (624a, 624b, 624c, 624d) Like the flex hinges of the first set, the flex hinge of each individual tab of the second set of tabs 614 allows the tab to bend relative to the other tabs of the set. Each tab (613a, 613b, 613c, 613d) of the first set of tabs 612 is operably connected to a corresponding tab (615a, 615b, 615c, 615d) of the second set of tabs 614 by corresponding two flex hinges (622a, 622b, 622c, 622d) to give two degrees of freedom. Any two degree of freedom joint can be used. The flex hinge of each separate tab allows the tab to bend relative to the other tabs of the set.

Bushing 606 includes clearance channels (607a, 607b, 607c, 607d) to accommodate the first set of tabs 612 and second set of tabs 614. Specifically, clearance channels (607a, 607b, 607c, 607d) accommodate each of tabs (613a, 613b, 613c, 613d) and tabs (615a, 615b, 615c, 615d). The clearance channels (607a, 607b, 607c, 607d) provide clearance for tabs (613a, 613b, 613c, 613d) and tabs (615a, 615b, 615c, 615d) when links 602 and 604 bend with respect to one another.

FIG. 13E shows a perspective view of bushing 606. As discussed above, clearance channels (607a, 607b, 607c, 607d) are designed to accommodate first set of tabs 612 and second set of tabs 614. Bushing 606 also includes socket 617. Socket 617 is configured to accept ball portions (616a, 616b, 616c, 616d).

Flexing of the flex hinges of first and second link sets 612 and 614 allows link 602 to pivot with respect to link 604, allowing link system 600 to bend. With further reference to FIGS. 13A and 13B, when an actuating force is applied to one or more cables in cable channels 624, 626, an axial force is provided in the direction of the axis to one side of link 602. As link 602 begins to pivot around the ball-and-socket joint (not shown), one or more flex hinges 620, 622, or 624 of the first and/or second sets of tabs 612,614 flex. Link 602 pivots with respect to link 604, bending link system 600.

Links 602, 604 of link system 600 are prevented from parallelogramming. With reference to FIG. 13B, when side load 640 is applied to link 602, the load is transferred to first set of tabs 612. First set of tabs 612, which is connected to second set of tabs 614, prevents translation of link 602 laterally with respect to link 604.

Each link 602, 604 also includes one central channel 630, 632, respectively, that is aligned with the central axis of each link. These channels form a central lumen through which an actuating cable may be passed. The central channel generally also provides passage for additional cables, wires, fiber optics, or other like elements associated with any desired tool or instrument used in conjunction with the link system or articulating mechanism of the invention. This allows the links and bushings to pivot relative to one another without impinging the passage of an actuating cable. While the provision of a central channel is advantageous for the above reasons, it will be appreciated that links and bushings can also be provided without such channels, and that control of tool or instrument associated with the link system or articulating mechanism of the invention can also be accomplished by routing actuating cables and other like elements along the periphery of the link system or articulating mechanism.

While the particular embodiment of the link system described above includes adjacent links including a protrusion having four depressions engaged by four tabs, it will be recognized that the protrusion can have a plurality of depressions and a plurality of tabs. Typically, there are at least as many tabs as the degrees of freedom in the pivot points between the links, i.e., for a one degree of freedom pivoting, at least one tab is used, and for two degrees of freedom, at least two tabs are used. By way of example and not limitation, each protrusion can have two, three, four, five, six, seven, eight, or more depressions, and each set of tabs can have two, three, four, five, six, seven, eight, or more individual tabs. For example, two tabs can be included with one degree of freedom hinges. In addition, while the particular embodiment of the link system described above includes two sets of tabs, the link system can include one set of tabs between adjacent links of the link system. The tabs in other embodiments of the link systems do not have to have flex hinges. The link system may be configured with or without a bushing. The link system may be a link system or portion of a link system, including a ball-and-socket joint or flex joints, in any combination, described in, for example, U.S. patent application Ser. Nos. 10/444,769, 10/948,911, and 10/928,479.

Figure 15A:
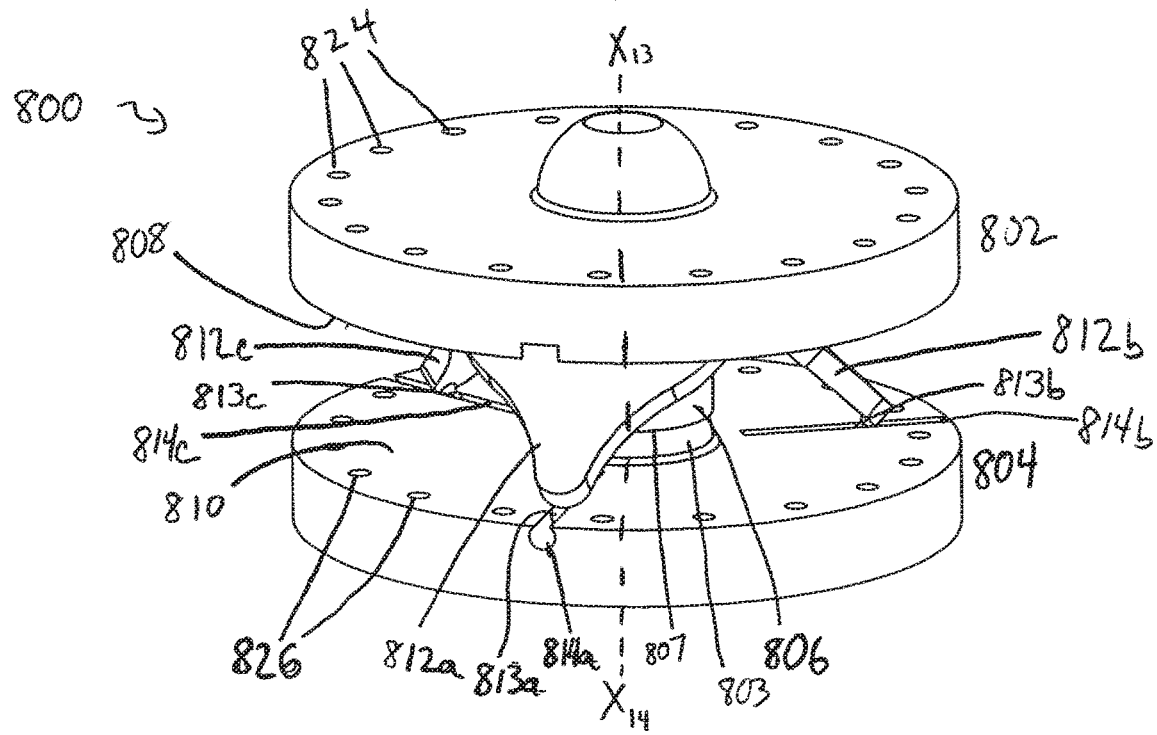
FIG. 15A shows a perspective view of a link system in a straight conformation, according to another embodiment of the invention.

Another exemplary embodiment of a link system designed to transmit torque while preventing parallelogramming is depicted in FIGS. 15A-D. Link system 800 includes adjacent links 802 and 804 separated by bushing 806. With reference to FIG. 15A, in the straight conformation central axis $X_{13}$ of link 802 is aligned with central axis $X_{14}$ of link 804. Convex protrusion 803 of link 804 is engaged by concave depression 807 of bushing 806. Convex protrusion 803 can pivot within concave depression 807. A similar concave protrusion and convex depression arrangement is between link 802 and bushing 806.

Figure 15C:
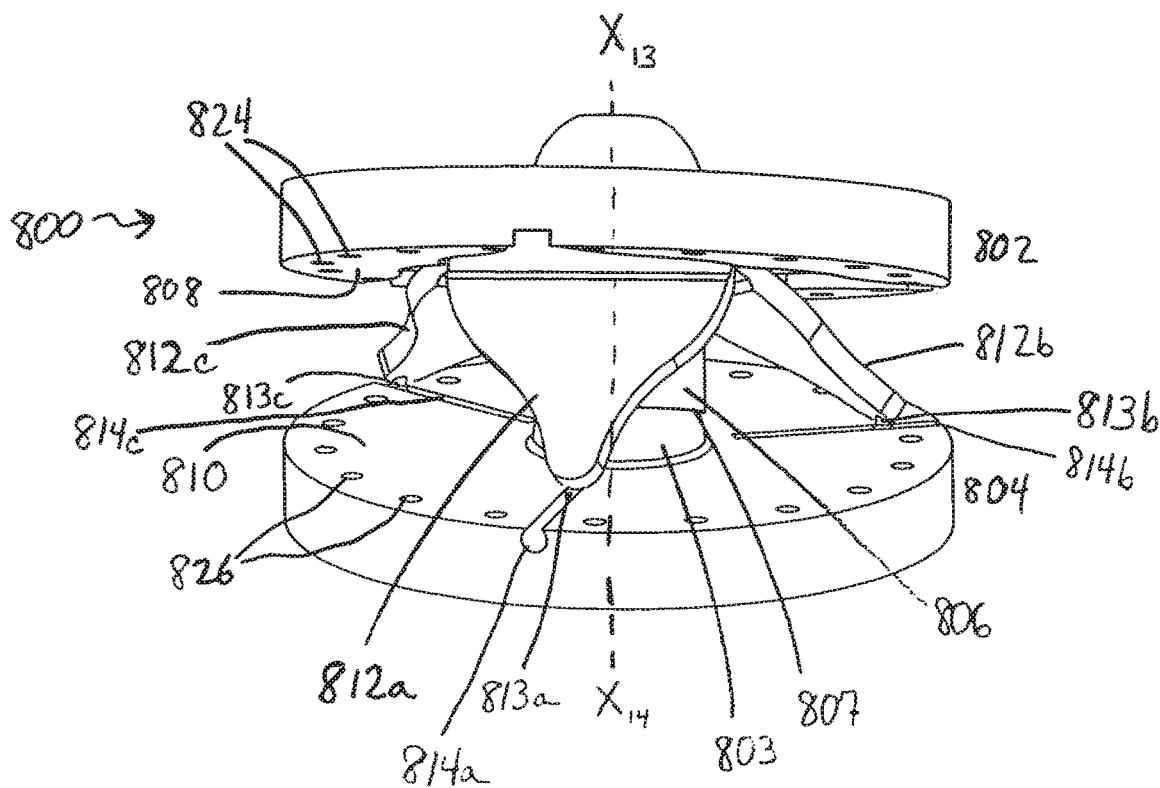
FIG. 15C shows a perspective view of the link system of FIG. 15A in a bent conformation.
Figure 15B:
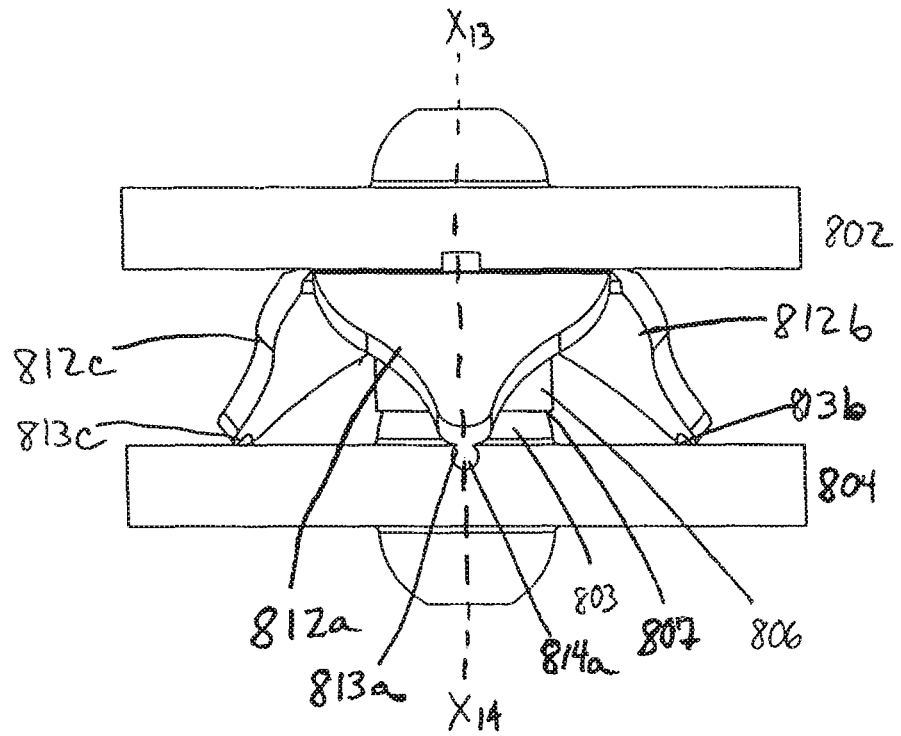
FIG. 15B shows a side view of the link system of FIG. 15A in a straight conformation, according to another embodiment of the invention.
Figure 15D:
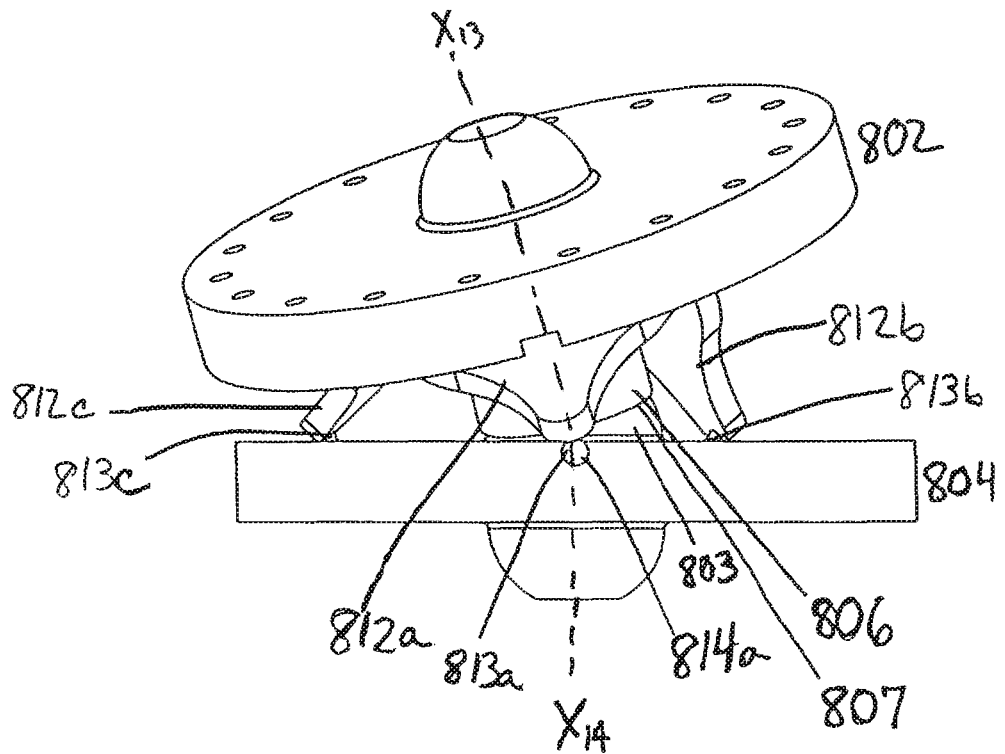
FIG. 15D shows a perspective view of the link system of FIG. 15A in a bent conformation.

Cable channels 824, 826 are offset from the axes $X_{13}$ and $X_{14}$ of links 802, 804, respectively, such that when a tension force is applied to one or more cables, concave protrusions of each link can rotate within their respective concave depression of bushing 806, pivoting each link 802, 804 and causing link set 800 to bend, as shown more clearly in FIGS. 15C and 15D. Adjacent link 802 includes a first set of three triangular tabs (812a, 812b, 812c) integrally formed with the link. Each triangular tab (812a, 812b, 812c) is connected to link 802 by a one degree of freedom joint and terminates at ball (813a, 813b, 813c). Link 804 includes three grooves (814a, 814b, 814c) extending radially away from the central axis $X_{14}$ of link 804. Each ball (813a, 813b, 813c) of each respective tab (812a, 812b, 812c) fits within a single groove (814a, 814b, 814c). Again, it will be appreciated that the tabs need not be integrally formed with the links, but can be connected to the links by other known methods. Also, the grooves can extend non-radially as long they are normal to the orientation of the one degree of freedom joint.

Each ball (813a, 813b, 813c) of each respective tab (812a, 812b, 812c) is configured to slide within its respective groove (814a, 814b, 814c) when link 802 pivots with respect to link 804. With reference to FIG. 15C, link 802 is bent with respect to link 804. Balls 813b and 813c slide radially within grooves 814b and 814c, respectively, away from central axis $X_{14}$ of link 804. Link 802 bends with respect to 804. Ball 813a slides radially within groove 814a toward central axis $X_{14}$ of link 804 as well as pivot side to side. Similarly, with reference to FIG. 15D, link 802 is bent with respect to link 804. Balls 813a and 813c slide radially within grooves 814a and 814c, respectively, away from central axis $X_{14}$ of link 804. Ball 813b slides radially within groove 814b toward central axis $X_{14}$ of link 804.

Link system 800 is designed to prevent parallelogramming. When a side load is applied to link 802, the tabs 812 operably connected to the grooves 814 prevent translation of link 802 laterally with respect to link 804. Moreover, when link 802 is rotated around axis $X_{13}$, torque generated by the rotation is transferred through each tab (812a, 812b, and 812c), to its corresponding groove (814a, 814b, and 814c). Torque is transferred from link 802 to link 804.

Each link 802, 804 also includes central channels aligned with the axis each link. Central channels form a central lumen through which one or more actuating cables may be passed. The cables can be used to control and/or actuate a stapler, such as the stapler depicted in FIG. 1, 107. The central channel generally also provides passage for additional cables, wires, fiber optics, or other like elements associated with any desired tool or instrument used in conjunction with the link system or articulating mechanism of the invention. Alternatively, a central channel is not included. Additional cables, wires, fiber optics, or other like elements associated with any desired tool or instrument used in conjunction with the link system can be provided off the axis of the link system.

The tabs can be disposed on any link system disclosed herein. In addition, tabs can be disposed on any link system disclosed in U.S. patent application Ser. Nos. 10/444,769, 10/948,911, and 10/928,479. While particular embodiments of link systems have been described as having certain number of tabs, it will be recognized that the link systems require a plurality of tabs. Typically, there are at least as many tabs as the degrees of freedom in the pivot points between the links, i.e., for a one degree of freedom pivoting, at least one tab is used, and for two degrees of freedom, at least two tabs are used. By way of example and not limitation, the link system can include two, three, four, five, six, or more tabs. While particular embodiments have been described as having triangular tabs, the tabs can be any shape. By way of example and not limitation, the tabs can be triangular, rectangular, pentagonal, hexagonal, curved, or partially curved. It will also be recognized that other embodiments of the link systems do not require a bushing. Tabs may be connected in any fashion known in the art, including a ball-and-socket joint, hinged joints, glue, or wire. Alternatively, tabs may be disposed on a flex hinge.

Exemplary flex hinges are described, for example, in U.S. patent application Ser. No. 10/928,479.

Other embodiments of the link sets or link systems also provide torque transmission between the adjacent links while still allowing for pivoting movement between the links, including links and link systems having engaging pins and corresponding receiving slots on the link system components.

FIGS. 16-18 show a representative embodiment of such a link system in greater detail. Turning to FIGS. 16A-16C, link 1000 includes ball section 1002 and socket 1004 on opposing ends of central axis of the link. Ball section 1002 includes pins 1006 and 1007 extending normal to central axis on opposing sides of the ball section. Socket 1004 includes slots 1008 and 1009 that run in a direction parallel to the central axis of the link. Ball section 1002 is configured to engage a corresponding socket 1004 on an adjacently located link. Likewise, socket 1004 is configured to receive a corresponding ball section 1002 on an adjacently located link, as is further depicted in FIGS. 17-19.

Link 1000 also includes a central channel 1010 aligned with central axis of the link that forms a central lumen through which actuating cables (not shown) are passed for controlling and/or actuating a tool. The central lumen generally also provides passage for additional cables, wires, fiber optics, or other like elements associated with any desired tool or instrument used in conjunction with the link system or articulating mechanism of the invention. Link 1000 further include cable channels 1012 and 1014 that allow the passage or anchoring of cable sets (not shown). Cable channels 1012 and 1014 run parallel to and are offset from central axis of link 1000, such that when a tension force is applied to one or more cables, ball section 1002 can pivot within a corresponding socket of an adjacently located link (or bushing). Likewise, a ball section from another located link (or bushing) can pivot within socket 1004.

Figures 17A, 17B, 17C:
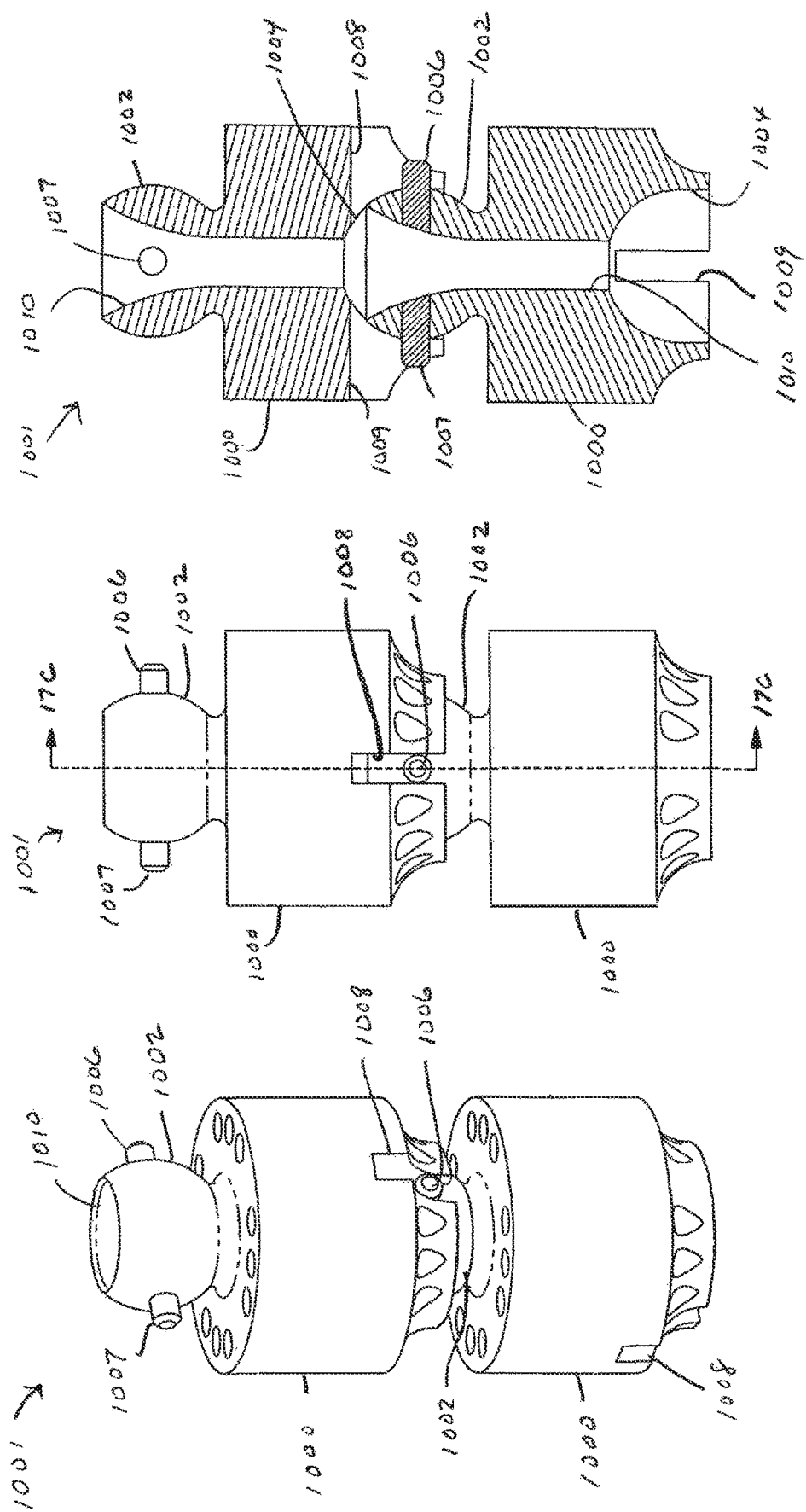
FIGS. 17A, 17B and 17C show perspective, side, and cross-sectional views, respectively, of a link assembly formed of the links of FIG. 16A, in an unbent conformation.

FIGS. 17-18 show two links 1000 engaged with one another to form a link system 1001. FIGS. 17A-17C depict the system in an unbent conformation, in which central axes of links 1000 are aligned. The ball section 1002 of the link engages socket 1004 of the adjacent link. Engagement of ball and socket allows thrust or axial loads to be transmitted between the links. As further depicted, pins 1006 and 1007 extend from opposite sides of ball section 1002 and engage slots 1008 and 1009, respectively, of the adjacent link. Thus, when link 1000 is rotated about central axis, the rotational force is transmitted to the adjacent link through the engaged pins and slots, providing for transfer of torque between the links, in both the unbent conformation, as shown in FIGS. 17A-17C, and in bent conformations, as shown in FIGS. 18A-18C and 19A-19C.

As previously noted, links 1000 include a central channel 1010. When assembled together, these central·channels 1010 form a central lumen through which actuating cables (not shown) are passed for controlling and/or actuating a tool. The central lumen generally also provides passage for additional cables, wires, fiber optics, or other like elements associated with any desired tool or instrument used in conjunction with the link system or articulating mechanism of the invention. This allows the links to pivot relative to one another without impinging the passage of an actuating cable in central channels 1010. While the provision of a central channel is advantageous for the above reasons, it will be appreciated that links can also be provided without such channels, and that control of a tool or instrument associated with the link system or articulating mechanism of the invention can also be accomplished by routing actuating cables and other like elements along channels located at or near the periphery of the link system or articulating mechanism.

As also noted, links 1000 further include cable channels 1012 and 1014 that are offset from the central axis of the link and that allow the passage or anchoring of cable sets (not shown), such that when a tension force is applied to one or more cables, ball section 1002 can pivot within socket 1004 of an adjacent link 1000. Pivoting motion of adjacent links 1000 with respect to each either can cause link system 1001 as a whole to bend.

Pivoting motion between adjacent links is more clearly illustrated with reference to FIGS. 18A-18C and 19A-19C. Specifically, each pin 1006, 1007, when engaging its respective slot 1008, 1009, is free to both translate and rotate within the slot and does not interfere with the full range of pivoting movement, allowing the two links 1000 to pivot freely about link 1006. This freedom of pivoting motion results in a bending of the link system, while retaining torque transmission between the links. Depending on the overall depth of the slot and the degree of a bend in the link system, either one or both of the pins remains engaged in its respective slot. Further, the degree of pivoting motion can be limited by depth of each slot relative to its corresponding pin.

Figure 20A:
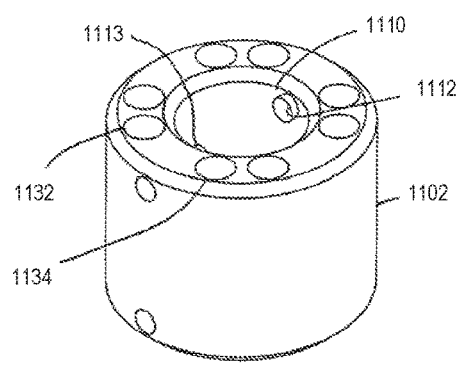
FIGS. 20A and 20B show perspective views of a link according to yet another embodiment of the invention.
Figure 21A:
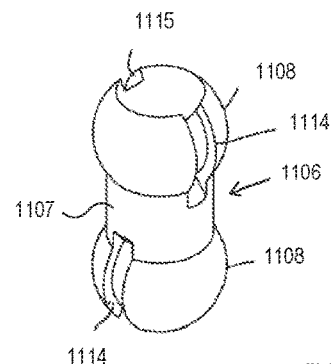
FIGS. 21A and 21B show perspective views of a bushing configured to engage the link of FIG. 20A.
Figure 20B:
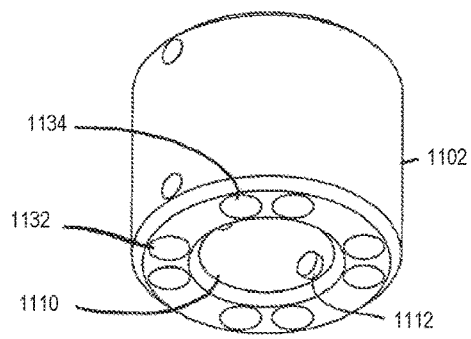
Figure 21B:
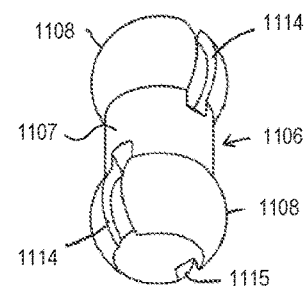
Figure 23B:
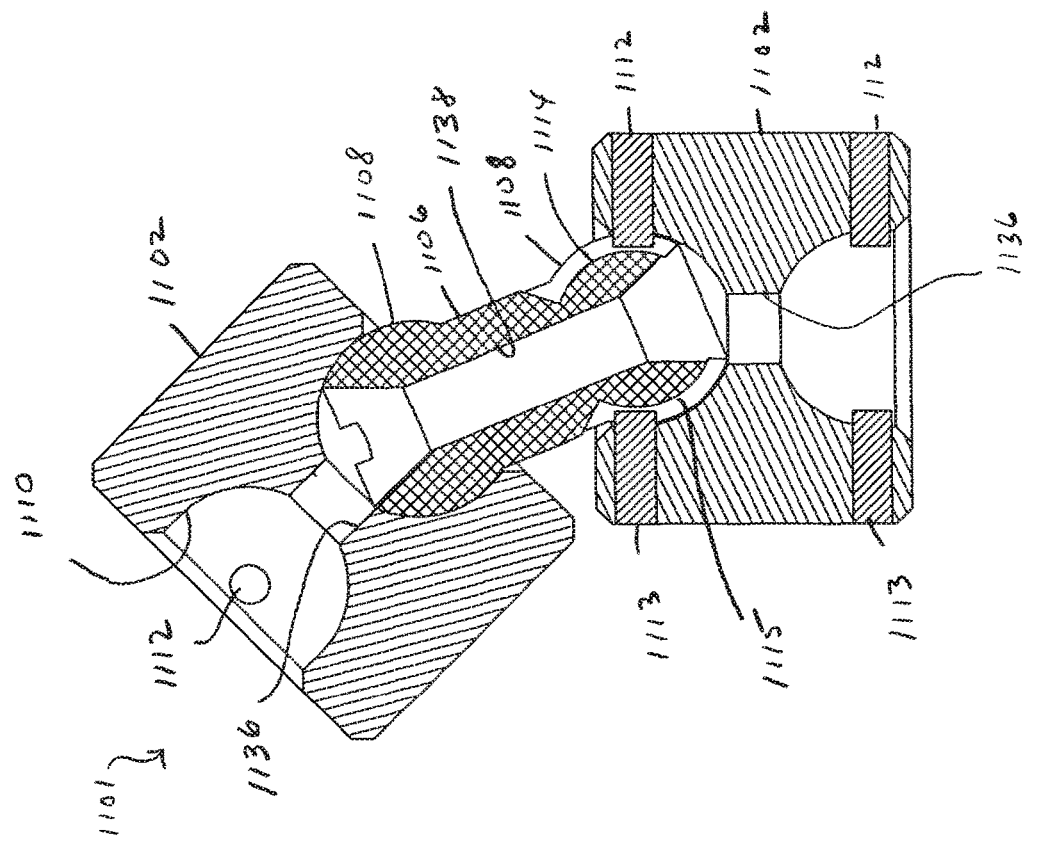
FIGS. 23A and 23B show side, and cross-sectional views, respectively, of a link assembly of FIG. 22A, in a bent conformation.
Figure 23A:
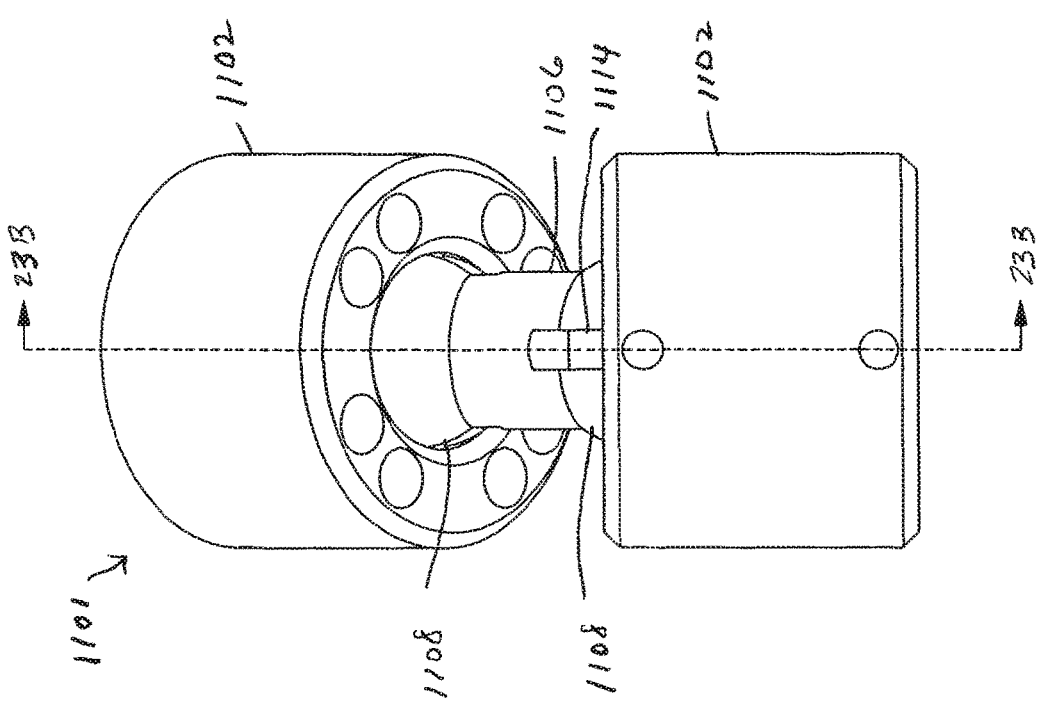

An alternative variation of links and link systems that employ engaging pins and receiving slots is depicted in FIGS. 20-24. In this variation, a bushing is deployed between adjacent links. Turning to FIGS. 20-21, components of the link system include links 1102 and bushing 1106. Link 1102 includes sockets 1110 on opposing ends of the central axis of the link. Sockets 1110 include pins 1112 and 1113 that extend in a direction normal to the central axis the link. Bushing 1106 includes ball sections 1108 on opposing ends of the central axis of an elongate member 1107 of the bushing. Each ball section includes slots 1114 and 1115 that are recessed in the ball section and that are aligned with the central axis of the bushing.

FIGS. 22A-C show the assembled link system 1101 in an unbent conformation in which the central axes of links 1102 and bushing 1106 are aligned. The bushing 1106 is operably connected to links 1102. The ball sections 1108 of bushing 1106 are engaged with sockets 1110 of links 1102. In particular, slots 1114, 1115 of each ball section 1108 receive pins 1112, 113 that are disposed in sockets 1110 of links 1102. Thus, when a link 1102 is rotated about its central axis, the rotational force is transmitted via bushing 1106 to the adjacent link 1102 through the engaged pins and slots of the link sockets and bushing ball sections, providing for transfer of torque between the links, in both the unbent conformation, as shown in FIGS. 22A-22C, and in bent conformations, as shown in FIGS. 23A-23B and 24A-24B.

Links 1102 likewise includes a central channel 1136 aligned with the link central axis as does bushing 1106 which similarly includes central channel 1138 aligned with its central axis. When assembled, these central channels 1136 and 1138 form a central lumen through which actuating cables (not shown) are passed for controlling and/or actuating a tool. As with other embodiments, the central lumen generally also provides passage for additional cables, wires, fiber optics, or other like elements associated with any desired tool or instrument used in conjunction with the link system or articulating mechanism of the invention. This allows the links and bushings to pivot relative to one another without impinging the passage of an actuating cable in central channels 1136, 1138. Again, while the provision of a central channel is advantageous for the above reasons, it will be appreciated that links and bushings can also be provided without such channels, and that control of a tool or instrument associated with the link system or articulating mechanism of the invention can also be accomplished by routing actuating cables and other like elements along channels at or near the periphery of the link system or articulating mechanism.

Also similar to other embodiments, links 1102 further include cable channels 1132 and 1134 that allow the passage or anchoring of cable sets (not shown). Cable channels 1132 and 1134 are offset from the central axis of link 1102 such that when a tension force is applied to one or more cables, adjacent links 1102 can pivot about bushing 1106. Pivoting motion of links 1102 with respect to one another or bushing 1106 causes link system 1101 as a whole to bend. Pivoting motion is more clearly illustrated with reference to FIGS. 23A-23B and 24A-24B. Again, the degree of pivoting motion of the links relative to bushings can be limited by depth of each slot relative to its corresponding pin.

It will be understood that sockets and ball sections can be disposed on either end of bushings or links in any combination, and that that such sockets and ball sections can include pins or slots or both. It will further be recognized that the links and bushings can have many configurations, provided that a link (or a bushing) contains either a pin or corresponding slot that engages a corresponding slot or a pin, respectively, of another link (or bushing). In the variations shown, slots and pins of a link or a bushing can be offset from one another. Further, by way of example and not limitation, the pins can extend from the socket or ball section of a link (or a bushing). It is not necessary that the pin be perpendicular to the central axis of the link (or bushing), provided that it engages its respective slot on another link (or bushing). Also, while particular embodiments of links have been described as having a pin extending in a direction normal to the central axis of the link (or bushing), it will be recognized that a pin can extend at any angle away from a ball section or a socket, provided that the pin extends along a radial line that intersects the center of the ball section or socket of the link (or bushing) and otherwise engages a corresponding slot in another link (or bushing).

Consistent with the configurations and parameters presented above, link systems according to the invention may be of any size and shape, as the purpose dictates. For surgical applications, their form usually depends on such factors as patient age, anatomy of the region of interest, intended application, and surgeon preference. As noted, the outer circumferences of links and bushings are generally cylindrical, and may include channels for passage of the cables that connect links to other links or components of a device, as well as additional cables, wires, fiber optics or other like elements associated with a desired tool or instrument used in conjunction with the link system. The channel diameters are usually slightly larger than the cable diameters, creating a slip fit. Further, the links may also include one or more channels for receiving elements of attachable surgical instruments or diagnostic tools or for passage of cables that actuate them. As noted, such channels can be located along the center or the periphery of the links or bushings. The links may typically have a diameter from about 0.5 mm to about 15 mm or more depending on the application. Bushings tend to have relatively comparable sizes to links and frequently have a smaller diameter. For endoscopic and laparoscopic applications, representative link diameters may range from about 2 mm to about 3 mm for small endoscopic and laparoscopic instruments, about 5 mm to about 7 mm for mid-sized endoscopic and laparoscopic instruments, and about 10 mm to about 15 mm for large endoscopic and laparoscopic instruments. For catheter applications, the diameter may range from about 1 mm to about 5 mm. The overall length of the links and bushings will vary, usually depending on the bend radius desired between links.

For surgical applications, the links or bushings or other components of the mechanism or device into which the links or bushings are incorporated may be made from any biocompatible material, including, but not limited to: stainless steel; titanium; tantalum; and any of their alloys; and polymers, e.g., polyethylene or copolymers thereof, polyethylene terephthalate or copolymers thereof, nylon, silicone, polyurethanes, fluoropolymers, poly (vinyl chloride), acrylonitrile-butadiene-styrene (ABS) terpolymer, polycarbonate, Delrin and Delrin substitutes (i.e. acetal homopolymers), combinations thereof, and other suitable materials known in the art. A lubricious coating may be placed on the links or bushings or other components if desired to facilitate advancement of the link system. The lubricious coating may include hydrophilic polymers such as polyvinylpyrrolidone, fluoropolymers such as tetrafluoroethylene, or silicones. A radio opaque marker may also be included on one or more links or bushings to indicate the location of the articulating mechanism or device upon radiographic imaging. Usually, the marker will be detected by fluoroscopy.

Although the many link systems that have been illustrated in the accompanying figures have a certain number of links and bushings, this is solely for the illustrative purpose of indicating the relationship of the individual mechanism or link and bushing components to one another. Any number of links and bushings may be employed, depending on such factors as the intended use and desired length and range of movement of the articulating mechanism.

As noted, cables may be used to actuate the link systems of the invention. In such embodiments, one or more links are connected to their corresponding link or segment at the distal end by two or more cables. Each cable set may be made up of at least two cables. As noted, movement of one link is controlled by its corresponding cable set and is independent of any other link. In certain variations, for example, a cable set will include three cables. By using a set of three cables to connect to a link, the link can be manipulated or moved in three degrees of freedom (i.e., up/down motion, left/right motion, and rotational or "rolling" motion), independently of any other links. By combining a plurality of links, multiple degrees of freedom are achieved, allowing the link system to be shaped into various complex configurations.

Cable diameters vary according to the application and may range from about 0.15 mm to about 3 mm. For catheter applications, a representative diameter may range from about 0.15 mm to about 0.75 mm. For endoscopic and laparoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including, but not limited to, biocompatible materials such as nickel-titanium alloy; stainless steel or any of its alloys; super elastic alloys; carbon fibers; polymers, e.g., poly (vinyl chloride), polyoxyethylene, polyethylene terephthalate and other polyesters, polyolefin, polypropylene, •and copolymers thereof; nylon; silk; and combinations thereof, or other suitable materials known in the art.

The cables may be affixed to the links according to ways known in the art, such as by using an adhesive or by brazing, gluing, soldering, welding, ultra-sonically welding, screwing, and the like, including methods described in pending and commonly U.S. application Ser. Nos. 10/444,769, 10/948,911, and 10/928,479, each of which is incorporated herein by reference in its entirety.

Spacer links, i.e., links not connected by discrete sets of cables, may also be included in the link systems and articulating mechanisms of the invention. These links act as passive links that are not independently actuatable, but do allow for pass through of cable sets to neighboring active links. Spacer links can be desirable for providing additional length in a link system or articulating mechanism. In addition, the inclusion of spacer links at one end of the mechanism allows for the proportional scaling of movement or motion of the corresponding other end. For example, the inclusion of spacer links at the proximal end of an articulating mechanism in which distal and proximal pairs of links are connected would require a more exaggerated movement by the user at the proximal end to achieve the desired motion at the distal end. This is advantageous in situations where fine, delicate controlled movements were desired, such as, for example, situations where there is a risk that a user may not possess the necessary dexterity to perform the desired procedure absent such proportional scaling of the distal end movement or motion. Alternatively, spacer links can be provided on the distal end, in which case the degree of distal end movements would be proportionally greater than those of the proximal end, which may also be desirable for particular applications. In addition to the above, proportional scaling of movement or motion can also be accomplished by increasing or decreasing the radius or distance that the cable channels are located from the central axis, as further described. For example, a movement of one link set can be configured such that an amplified movement in a proximal link set can result in an amplified movement in a distal link set, as described in U.S. patent application Ser. Nos. 10/928,479, 10/444,769, and 10/948,911.

The links and/or bushings described herein also may be configured to have positive, negative, or neutral cable bias, as described in U.S. patent application Ser. Nos. 10/444,769, 10/948,911, and 10/928,479, each of which is incorporated herein by reference in its entirety.

The linking systems, articulating mechanisms, and devices incorporating such systems or mechanisms may also include a locking mechanism. When activated, the locking mechanism prevents one or more links or pairs of links from moving as described in U.S. patent application Ser. Nos. 10/444,769, 10/948,911, and 10/928,479, each of which is incorporated herein by reference in its entirety. The linking systems, articulation mechanisms, and devices disclosed herein can incorporate any aspects of any other devices disclosed in U.S. patent application Ser. Nos. 10/444,769, 10/948,911, and 10/928,479, including but not limited to steerable catheters, endoscopes, and hand-actuated devices.

The invention also contemplates kits for providing various linking systems, articulating mechanisms, locking mechanisms, and associated accessories. For example, kits containing linking systems and articulating mechanisms having different lengths, different segment diameters, and/or different types of tools or instruments may be provided. The kits may optionally include different types of pre-assembled locking mechanisms. The kits may be further tailored for specific applications. For example, kits for surgical applications can be configured for, e.g., endoscopy, retraction, or catheter placement, and/or for particular patient populations, e.g., pediatric or adult.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the appended claims. Applicants have not abandoned or dedicated to the public any unclaimed subject matter.

I claim:

1. An articulating mechanism capable of transmitting torque for remote manipulation of a surgical or diagnostic tool comprising:
    at least two adjacent links, wherein a first adjacent link of the adjacent links has a ball and a second adjacent link of the adjacent links has a socket for receiving the ball to form a ball and socket joint, wherein the ball and socket joint includes an engaging pin configured to engage with a reciprocal slot when the adjacent links are in a first configuration, the slot including an open proximal end, wherein the engaging pin is configured to disengage from the slot when the adjacent links are in a second configuration, the engaging pin and slot providing for torque transmission between the adjacent links while also allowing for pivoting movement of the first adjacent link relative to the second adjacent link, wherein the first adjacent link is pivoted relative to the second adjacent link when the adjacent links are in the second configuration, and wherein the ball remains within the socket both when the adjacent links are in the first configuration and when the adjacent links are in the second configuration; and
    at least one set of cables connecting the first adjacent link and the second adjacent link to one another such that movement of the first adjacent link causes corresponding relative movement of the second adjacent link.

2. The articulating mechanism of claim 1, wherein the pin extends from the ball and wherein the slot is recessed in the socket.

3. The articulating mechanism of claim 1, wherein the pin extends from the socket and wherein the slot is recessed in the ball.

4. The articulating mechanism of claim 1, wherein at least the first adjacent link includes both a first ball and a first socket for receiving the second adjacent link.

5. The articulating mechanism of claim 1, wherein the pin of the ball and socket joint extends in a direction generally perpendicular to a central longitudinal axis through the adjacent links.

6. The articulating mechanism of claim 1, wherein the first adjacent link includes a first central channel, and wherein the second adjacent link includes a second central channel.

7. The articulating mechanism of claim 6, wherein the first central channel is in communication with the second central channel to form a central lumen.

8. The articulating mechanism of claim 1, wherein a depth of the slot limits a degree of the pivoting movement relative to the pin.

9. The articulating mechanism of claim 1, wherein when the pin is mated with the slot, the pin is configured to translate and rotate with the slot.

10. The articulating mechanism of claim 1, wherein the ball and socket joint further includes a pair of slots, the pair of slots including the slot and a second slot, and wherein the slot and the second slot extend in opposite directions from a central longitudinal axis through the adjacent links.

11. The articulating mechanism of claim 10, wherein the second slot includes an open proximal end.

12. The articulating mechanism of claim 1, wherein the slot further includes a longitudinal opening perpendicular to the open proximal end.

13. An articulating link system capable of transmitting torque comprising:
at least two adjacent links, wherein a first adjacent link of the adjacent links has a ball and a second adjacent link of the adjacent links has a socket for receiving the ball to form a ball and socket joint, wherein the ball and socket joint includes an engaging pin configured to engage with a reciprocal slot when the adjacent links are in a first configuration, the slot including an open proximal end, wherein the engaging pin is configured to disengage from the slot when the adjacent links are in a second configuration, the engaging pin and slot providing for torque transmission between the adjacent links while also allowing for pivoting movement of the first adjacent link relative to the second adjacent link, wherein the first adjacent link is pivoted relative to the second adjacent link when the adjacent links are in the second configuration, and wherein the ball remains within the socket both when the adjacent links are in the first configuration and when the adjacent links are in the second configuration.

14. The articulating link system of claim 13, wherein the pin extends from the ball and wherein the slot is recessed in the socket.

15. The articulating link system of claim 13, wherein the pin extends from the socket and wherein the slot is recessed in the ball.

16. The articulating link system of claim 13, wherein at least the first adjacent link includes both a first ball and a first socket for receiving the second adjacent link.

17. The articulating link system of claim 13, wherein the first adjacent link includes a first central channel, and wherein the second adjacent link includes a second central channel.

18. The articulating link system of claim 17, wherein the first central channel is in communication with the second central channel to form a central lumen.

19. The articulating link system of claim 18, further comprising an elongated member configured to extend through the central lumen.

20. The articulating link system of claim 13, wherein the ball and socket joint further includes a pair of slots, the pair of slots including the slot and a second slot, and wherein the slot and the second slot extend in opposite directions from a central longitudinal axis through the adjacent links.

* * * * *